US009216981B2

(12) United States Patent
Shim et al.

(10) Patent No.: US 9,216,981 B2
(45) Date of Patent: Dec. 22, 2015

(54) PURINYLPYRIDINYLAMINO-2,4-DIFLUOROPHENYL SULFONAMIDE DERIVATIVE, PHARMACEUTICALLY ACCEPTABLE SALT THEREOF, PREPARATION METHOD THEREOF, AND PHARMACEUTICAL COMPOSITION WITH INHIBITORY ACTIVITY AGAINST RAF KINASE, CONTAINING SAME AS ACTIVE INGREDIENT

(75) Inventors: Eun Kyong Shim, Gyeonggi-do (KR); Nam Doo Kim, Incheon (KR); Tae Bo Shim, Seoul (KR); Seung Yong Kim, Gyeonggi-do (KR)

(73) Assignee: Medpacto, Inc. (KR)

( * ) Notice: Subject to any disclaimer, the term of this patent is extended or adjusted under 35 U.S.C. 154(b) by 38 days.

(21) Appl. No.: 13/990,910

(22) PCT Filed: Nov. 25, 2011

(86) PCT No.: PCT/KR2011/009091
§ 371 (c)(1),
(2), (4) Date: Aug. 9, 2013

(87) PCT Pub. No.: WO2012/074249
PCT Pub. Date: Jun. 7, 2012

(65) Prior Publication Data
US 2013/0317023 A1 Nov. 28, 2013

(30) Foreign Application Priority Data

Dec. 2, 2010 (KR) .................. 10-2010-0122047
Nov. 25, 2011 (KR) .................. 10-2011-0124360

(51) Int. Cl.
*C07D 473/00* (2006.01)
*C07D 401/04* (2006.01)

(52) U.S. Cl.
CPC ............ *C07D 473/00* (2013.01); *C07D 401/04* (2013.01)

(58) Field of Classification Search
CPC .................................................. C07D 473/00
See application file for complete search history.

(56) References Cited

U.S. PATENT DOCUMENTS

2006/0009453 A1* 1/2006 Geuns-Meyer et al. ...... 514/241
2010/0273764 A1 10/2010 Andrews et al.

FOREIGN PATENT DOCUMENTS

| CA | 2855950 | 5/2013 |
|---|---|---|
| JP | 2009/525978 | 7/2009 |
| WO | WO 2007/092531 | 8/2007 |
| WO | WO 2008-153947 A2 | 12/2008 |
| WO | WO 2010/126895 | 11/2010 |
| WO | WO 2013/071865 | 5/2013 |

OTHER PUBLICATIONS

Roberts, PJ.Oncogene (2007) 26, 3291-3310.*
Sridhar, Srikala. Mol Cancer ther (2005) 4:4 677-685.*
MedicineNet.com. <http://www.medterms.com> 2004.*
Lappert, M., Protchenko, A., Power, P. and Seeber, A. (2008) Metal Amide Chemistry, John Wiley & Sons, Ltd, Chichester, UK.*
Official Action for Canadian Patent Application No. 2,820,550, dated Sep. 15, 2014, 3 pages.
Official Action (with English translation) for Japanese Patent Application No. 2013-541920, dated Sep. 30, 2014, 6 pages.
Ahn et al., "The role of autophagy in cytotoxicity induced by new oncogenic B-Raf inhibitor UI 152 in v Ha-ras transformed fibroblasts," Biochem. Biophys. Res. Comm., 2012, vol. 417, pp. 857-863.
Extended Search and Examination Report for European Patent Application No. 11844745.7, mailed Oct. 22, 2013, 6 pages.
International Search Report prepared by the Korean Intellectual Property Office on Jun. 18, 2012, for International Application No. PCT/KR2011/009091.
Peyssonnaux et al. "The Raf/MEK/ERK pathway: new concepts of activation"; Biology of the Cell, vol. 93 (2001), pp. 53-62.
Wellbrock et al. "The Raf Proteins take Center Stage"; Molecular Cell Biology, vol. 5, Nov. 2004, pp. 875-885.
Mercer et al. "Raf proteins and cancer: B-Raf is identified as a mutational target"; Biochimica et Biophysica Acta, vol. 1653 (2003), pp. 25-40.
Davies et al. "Mutations of the BRAF gene in human cancer"; Nature, vol. 417, Jun. 27, 2002, pp. 949-954.
Hingorani et al. "Suppression of BRAF$^{V599E}$ in Human Melanoma Abrogates Transformation"; Cancer Research, vol. 63 (2003), pp. 5198-5202.
Wellbrock et al. "$^{V599E}$B-RAF is an Oncogene in Melanocytes"; Cancer Research, vol. 64 (2004), pp. 2338-2342.
Official Action with English Translation for China Patent Application No. 201180066781.9, dated Nov. 3, 2014, 13 pages.
Hagemann et al. "Isotype-Specific Functions of Raf Kinases"; Experimental Cell Research, vol. 253 (1999), pp. 34-46.

* cited by examiner

*Primary Examiner* — Golam M M Shameem
*Assistant Examiner* — Laura Daniel
(74) *Attorney, Agent, or Firm* — Sheridan Ross P.C.

(57) ABSTRACT

A novel purinylpyridinylamino-2,4-difluorophenyl sulfonamide derivative, a pharmaceutically acceptable salt thereof, a preparation method thereof, and a pharmaceutical composition with an inhibitory activity against Raf kinase, containing the same as an active ingredient are provided. The purinylpyridinylamino-2,4-difluorophenyl sulfonamide derivative of the present invention effectively regulates the activity of B-Raf kinase, and thus may be useful for preventing or treating cancers induced by the over-activation of Raf kinase, especially various melanoma, colorectal cancer, prostate cancer, thyroid cancer, ovarian cancer and the like.

12 Claims, No Drawings

PURINYLPYRIDINYLAMINO-2,4-DIFLUOROPHENYL SULFONAMIDE DERIVATIVE, PHARMACEUTICALLY ACCEPTABLE SALT THEREOF, PREPARATION METHOD THEREOF, AND PHARMACEUTICAL COMPOSITION WITH INHIBITORY ACTIVITY AGAINST RAF KINASE, CONTAINING SAME AS ACTIVE INGREDIENT

CROSS REFERENCE TO RELATED APPLICATIONS

This application is a national stage application under 35 U.S.C. 371 and claims the benefit of PCT Application No. PCT/KR2011/009091 having an international filing date of 25 Nov. 2011, which designated the United States, and which PCT application claimed the benefit of Korean Patent Application No. 10-2010-0122047 filed 2 Dec. 2010, and Korean Patent Application No. 10-2010-0124360 filed 25 Nov. 2011, the disclosure of each of which is incorporated herein by reference.

BACKGROUND

1. Field of the Invention

The present invention relates to a novel purinylpyridinylamino-2,4-difluorophenyl sulfonamide derivative, a pharmaceutically acceptable salt thereof, a preparation method thereof, and a pharmaceutical composition with an inhibitory activity against Raf kinase, containing the same as an active ingredient.

2. Description of the Related Art

Cancer, as one of the most common diseases people can contract, has becoming a major cause of death. Many research groups have invested a large sum of research funds over recent decades into development of effective treatments for cancer. However, only a few anticancer treatments are proved to be effective, but there is rarely an effective treatment for most of cancers.

Most of the compounds commonly used for chemotherapy up to the present have a risk of side effects and tolerance. One of the side effects is that currently used anticancer treatments cannot act on cancer cells selectively and exclusively from healthy cells, causing toxicity to normal cells. As an alternative to developing an anticancer drug or treatment with less side effects yet higher curative value, there needs an anticancer drug or treatment that can act on metabolic pathway or the constituents of the pathway, i.e. the targets which are expressed in cancer cells but not or hardly expressed in healthy cells. Protein kinase is an enzyme catalyzing the phosphorylation of a hydroxyl group of a particular protein residue, e.g., tyrosine, serine, or threonine residue. The phosphorylation can activate the function of protein, and protein kinase plays a key role in regulating a multiple cellular processes including particular metabolism, cell proliferation, cell differentiation, cell migration, or cell survival. Among the various cellular actions involving the activity of protein kinase, particular pathways are considered a suitable target for the treatment of cancer-related diseases and other diseases. In this regard, one of the objectives of the present invention is to provide a composition that has anticancer activity and functions particularly in connection with the kinase.

Ras/Raf/MEK/ERK protein kinase signaling pathway plays a very important role in regulating the cellular functions and is involved, specifically, in cell proliferation, cell differentiation, cell survival, and angiogenesis [Biology of the Cell, 2001, 93, 53~62]. In the signaling pathway, if guanosine triphosphate (GTP) is conjugated with Ras protein, the Raf protein in the plasma membrane is phosphorylated and activated. The activated Raf protein phosphorylates and activates MEK protein and the MEK protein phosphorylates and activates ERK protein. Accordingly, translocation of the activated ERK from cytoplasm to nucleus results in phosphorylating and regulating the activities of the transcription factors such as Elk-1 and Myc.

Raf protooncogene is serine/threonine (Ser/Thr) protein kinase, which is a substance transmitting the signals sent from the growth factor receptor activated in cell membrane to the transcription factor in nucleus. The activation of the Raf protein is accompanied by the phosphorylation of tyrosine, serine, and threonine residues of the Raf protein. The direct phosphorylation by the receptor tyrosine kinase or the phosphorylation by the protein phosphorylation enzymes regulated by the receptors is believed to be the mechanism of the Raf activation. In the case of the regulation by the receptors, Ras is involved in the activation of Raf. The signals arrived at Raf are transmitted back to the nucleus through the signaling pathway connected to the Raf/MEK/ERK protein kinase. In the signaling pathway, a series of kinases are arranged lengthwise to transmit signals, which performs an essential role in growth and differentiation of cells [Nature Rev. Mol. Cell. Biol., 2004, 5, 875~885].

In this way, Raf functions as a major propagator of the Ras function. Therefore, a theoretical background for anticancer treatments can be established for the cancers that have mutated or activated Ras mutations, to inhibit the actions of the protein. The Raf protein has isoforms of A-Raf, B-Raf, and C-Raf that play three different functions [Biochim. Biophys. Acta., 2003, 1653, 25~40]. Among these, B-Raf plays a key role in connecting the signaling from Ras to MEK. All these three Raf genes are expressed in most of the tissues. B-Raf and A-Raf are highly expressed in neural tissue and urogenital tissue, respectively. Each in the Raf family has a very similar amino acid sequence, but can be identified by biochemical activity and biological function [Exp. Cell. Res. 1999, 253, 34~46]. According to the research results achieved so far, B-Raf is an important isoform protein related to cell proliferation and an important target of the oncogenic Ras. Abnormal mutations in the body have been confirmed only in the case of B-Raf, which are believed to occur in malignant cutaneous melanoma at an incidence rate of 30~60% [Nature, 2002, 417, 949~954], thyroid cancer at 30~50%, colorectal cancer at 5~20%, and ovarian cancer at 30% or less [Nature Rev. Mol. Cell Biology, 2004, 5, 875~885]. Until now, 45 or more B-Raf mutations have been known. And among these mutations, the mutation from valine 600 into glutamic acid is most frequently observed in more than 90% of human cancers. This mutation is considered to increase the activity of B-Raf kinase and transmit the Raf/MEK/ERK signals to a downstream signaling pathway including the structural activity of ERK as a result of the activities of the Ras and growth factor receptors. The mutated B-Raf protein is transformed in NIH3T3 cells [Nature, 2002, 417, 949~954] and melanophores [Cancer Res., 2004, 64, 2338~2342], and is essential for the survival and transformation of melanoma [Cancer Res., 2003, 63, 5198~5202]. Therefore, the B-Raf at the core of the serial signal transduction of Raf/MEK/ERK plays a vital role in the survival of tumors.

Accordingly, the inventors of the present invention completed the present invention as a result of the long-time researches on the inhibitor that can regulate the activity of B-Raf kinase, after synthesizing a novel purinylpyridinylamino-2,4-difluorophenyl sulfonamide derivative represented by Formula 1, which has a desirable activity against Raf kinase, and discovering that the derivative has a desirable effect on the diseases induced by the over-activity of Raf kinase.

SUMMARY OF THE INVENTION

The objective of the present invention is to provide a purinylpyridinylamino-2,4-difluorophenyl sulfonamide derivative or a pharmaceutically acceptable salt thereof.

Another objective of the present invention is to provide a method for preparing the purinylpyridinylamino-2,4-difluorophenyl sulfonamide derivatives or the pharmaceutically acceptable salts thereof.

Further, the other objective of the present invention is to provide a pharmaceutical composition for prevention or treatment of diseases induced by over-activation of Raf kinase, containing the purinylpyridinylamino-2,4-difluorophenyl sulfonamide derivatives or the pharmaceutically acceptable salts thereof as an active ingredient.

In order to achieve the aforementioned objectives, the present invention provides a purinylpyridinylamino-2,4-difluorophenyl sulfonamide derivative represented by the following Formula 1 or a pharmaceutically acceptable salt thereof.

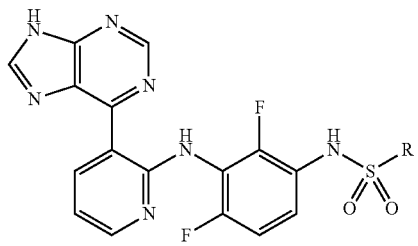

[Formula 1]

(The substituent shown above is the same as described in the present disclosure.)

Further, the present invention provides a method for preparing the purinylpyridinylamino-2,4-difluorophenyl sulfonamide derivatives or pharmaceutically acceptable salts thereof.

Furthermore, the present invention provides a pharmaceutical composition, which contains the purinylpyridinylamino-2,4-difluorophenyl sulfonamide derivatives or pharmaceutically acceptable salts thereof as an active ingredient, for the prevention and treatment of the diseases caused by over-activity of Raf kinase.

According to the present invention, the purinylpyridinylamino-2,4-difluorophenyl sulfonamide derivatives can regulate B-Raf kinase activity effectively and thus can be useful for preventing or treating such diseases that can be induced by over-activity of Raf kinase as cancers, in particular, including melanoma, colorectal cancer, prostate cancer, thyroid cancer, and ovarian cancer.

DESCRIPTION OF THE PREFERRED EMBODIMENTS

Hereinafter, the present invention is described in detail.

The present invention provides a purinylpyridinylamino-2,4-difluorophenyl sulfonamide derivative represented by the following Formula 1 or a pharmaceutically acceptable salt thereof.

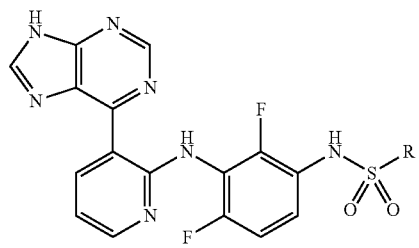

[Formula 1]

(In the Formula 1 above,

R is $C_1$-$C_6$ straight or branched alkyl; $C_3$-$C_6$ cycloalkyl non-substitutable or substituted with one or more selected from the group consisting of halogen and $C_1$-$C_6$ straight or branched alkyl; $C_5$-$C_6$ aryl substituted with one or more selected from the group consisting of halogen, $C_1$-$C_6$ straight or branched alkyl, and $C_1$-$C_6$ straight or branched alkoxy substituted with $C_1$-$C_6$ straight or branched alkoxy and halogen; $C_5$-$C_{12}$ single or double ring heteroaryl non-substitutable or substituted with one or more selected from the group consisting of $C_1$-$C_6$ straight or branched alkyl substituted with halogen, $C_1$-$C_6$ straight or branched alkyl, $C_1$-$C_6$ straight or branched alkyloxycarbonyl, and $C_5$-$C_6$ heterocycloalkyl containing one or more oxygen (O) in the ring; $C_5$-$C_6$ heterocycloalkyl non-substitutable or substituted with one or more selected from the group consisting of halogen and $C_1$-$C_6$ straight or branched alkyl; or $C_5$-$C_6$ aryl $C_1$-$C_6$ straight or branched alkyl non-substitutable or substituted with halogen, nitro, and $C_1$-$C_6$ straight or branched alkyl. At this time, the heteroaryl and heterocycloalkyl contain one or more heteroatom selected from the group consisting of N, O, and S in the ring.

More preferably, the R is methyl; ethyl; propyl; isopropyl; butyl; isobutyl; cyclopropyl; cyclobutyl; cyclopentyl; cyclohexyl; $C_5$-$C_6$ aryl non-substitutable or substituted with one or more selected from the group consisting of chloro, fluoro, bromo, methyl, ethyl, propyl, isopropyl, butyl, isobutyl, methoxy, ethoxy, propoxy, butoxy, trifluoromethoxy, fluoromethoxy, difluoromethoxy, and trifluoroethoxy; $C_5$-$C_{12}$ single or double ring heteroaryl non-substitutable or substituted with one or more selected from the group consisting of chloro, fluoro, bromo, methyl, ethyl, propyl, isopropyl, butyl, isobutyl, methyloxycarbonyl, ethyloxycarbonyl, propyloxycarbonyl, butyloxycarbonyl, t-butyloxycarbonyl, and dioxolanyl; $C_5$-$C_6$ heterocycloalkyl non-substitutable or substituted with one or more selected from the group consisting of chloro, fluoro, bromo, methyl, ethyl, propyl, isopropyl, butyl, and isobutyl; or $C_5$-$C_6$ aryl $C_1$-$C_6$ straight or branched alkyl non-substitutable or substituted with one or more selected from the group consisting of chloro, fluoro, bromo, nitro, methyl, ethyl, propyl, isopropyl, butyl, and isobutyl. At this time, the heteroaryl and heterocycloalkyl contain one or more heteroatom selected from the group consisting of N, O, and S in the ring.

Most preferably, the R is methyl; ethyl; propyl; isopropyl; cyclopropyl; cyclohexyl; phenyl non-substitutable or substituted with one or more selected from the group consisting of chloro, fluoro, methyl, methoxy, and trifluoromethoxy; thiophene, thiazole, furan, imidazole, pyridine, dihydrobenzofuran, benzofuran, chroman, benzothiazole, indole, or pyrazole non-substitutable or substituted with one or more selected from the group consisting of methyl, methyloxycarbonyl(methylester), and dioxolanyl; morpholine; or phenylmethyl substituted with nitro.

Further, novel purinylpyridinylamino-2,4-difluorophenyl sulfonamide derivatives represented by Formula 1 are more specifically exemplified as follows:

(1) N-(3-(3-(9H-purin-6-yl)pyridin-2-ylamino)-2,4-difluorophenyl)propane-2-sulfonamide;
(2) N-(3-(3-(9H-purin-6-yl)pyridin-2-yl amino)-2,4-difluorophenyl)-3-(trifluoromethyl)benzene sulfonamide;
(3) N-(3-(3-(9H-purin-6-yl)pyridin-2-yl amino)-2,4-difluorophenyl)-4-(trifluoromethyl)benzene sulfonamide;
(4) N-(3-(3-(9H-purin-6-yl)pyridin-2-yl amino)-2,4-difluorophenyl) thiophene-2-sulfonamide;
(5) N-(3-(3-(9H-purin-6-yl)pyridin-2-yl amino)-2,4-difluorophenyl) propane-1-sulfonamide;
(6) N-(3-(3-(9H-purin-6-yl)pyridin-2-yl amino)-2,4-difluorophenyl)-3,4-dichloro benzene sulfonamide;
(7) N-(3-(3-(9H-purin-6-yl)pyridin-2-yl amino)-2,4-difluorophenyl)benzofuran-2-sulfonamide;
(8) N-(3-(3-(9H-purin-6-yl)pyridin-2-yl amino)-2,4-difluorophenyl)-4-chloro-2-fluoro benzene sulfonamide;
(9) N-(3-(3-(9H-purin-6-yl)pyridin-2-yl amino)-2,4-difluorophenyl)-1-(2-nitrophenyl)methane sulfonamide;
(10) N-(3-(3-(9H-purin-6-yl)pyridin-2-yl amino)-2,4-difluorophenyl)-3,4-dimethoxy benzene sulfonamide;
(11) N-(3-(3-(9H-purin-6-yl)pyridin-2-yl amino)-2,4-difluorophenyl)cyclohexane sulfonamide;
(12) N-(3-(3-(9H-purin-6-yl)pyridin-2-yl amino)-2,4-difluorophenyl)-4-(trifluoromethoxy)benzene sulfonamide;
(13) N-(3-(3-(9H-purin-6-yl)pyridin-2-yl amino)-2,4-difluorophenyl)-4-fluoro-2-(trifluoromethyl)benzene sulfonamide;
(14) N-(3-(3-(9H-purin-6-yl)pyridin-2-yl amino)-2,4-difluorophenyl)-3-chloro-2-methyl benzene sulfonamide;
(15) N-(3-(3-(9H-purin-6-yl)pyridin-2-yl amino)-2,4-difluorophenyl)furan-2-sulfonamide;
(16) methyl-3-(N-(3-(3-(9H-purin-6-yl)pyridin-2-yl amino)-2,4-difluorophenyl)sulfamoyl)thiophene-2-carboxylate;
(17) N-(3-(3-(9H-purin-6-yl)pyridin-2-yl amino)-2,4-difluorophenyl)thiophene-3-sulfonamide;
(18) N-(3-(3-(9H-purin-6-yl)pyridin-2-yl amino)-2,4-difluorophenyl)furan-3-sulfonamide;
(19) N-(3-(3-(9H-purin-6-yl)pyridin-2-yl amino)-2,4-difluorophenyl)cyclopropane sulfonamide;
(20) N-(3-(3-(9H-purin-6-yl)pyridin-2-yl amino)-2,4-difluorophenyl)-2,4-dimethylthiazole-5-sulfonamide;
(21) N-(3-(3-(9H-purin-6-yl)pyridin-2-yl amino)-2,4-difluorophenyl)morpholine-4-sulfonamide;
(22) N-(3-(3-(9H-purin-6-yl)pyridin-2-yl amino)-2,4-difluorophenyl)-1-methyl-1H-imidazole-4-sulfonamide;
(23) N-(3-(3-(9H-purin-6-yl)pyridin-2-yl amino)-2,4-difluorophenyl)-5-methylfuran-2-sulfonamide;
(24) N-(3-(3-(9H-purin-6-yl)pyridin-2-yl amino)-2,4-difluorophenyl)-5-(1,3-dioxolane-2-yl)furan-2-sulfonamide;
(25) N-(3-(3-(9H-purin-6-yl)pyridin-2-yl amino)-2,4-difluorophenyl)-2,5-dimethylfuran-3-sulfonamide;
(26) N-(3-(3-(9H-purin-6-yl)pyridin-2-yl amino)-2,4-difluorophenyl)-5-methyl-2-(trifluoromethyl)furan-3-sulfonamide;
(27) N-(3-(3-(9H-purin-6-yl)pyridin-2-yl amino)-2,4-difluorophenyl)-2-chloro-6-methyl benzene sulfonamide;
(28) N-(3-(3-(9H-purin-6-yl)pyridin-2-yl amino)-2,4-difluorophenyl)-3-chloro-4-fluoro benzene sulfonamide;
(29) N-(3-(3-(9H-purin-6-yl)pyridin-2-yl amino)-2,4-difluorophenyl)-3-chloro-2-fluoro benzene sulfonamide;
(30) N-(3-(3-(9H-purin-6-yl)pyridin-2-yl amino)-2,4-difluorophenyl)pyridin-3-sulfonamide;
(31) N-(3-(3-(9H-purin-6-yl)pyridin-2-yl amino)-2,4-difluorophenyl)-2-methyl benzene sulfonamide;
(32) N-(3-(3-(9H-purin-6-yl)pyridin-2-yl amino)-2,4-difluorophenyl)-2-chloro benzene sulfonamide;
(33) N-(3-(3-(9H-purin-6-yl)pyridin-2-yl amino)-2,4-difluorophenyl)-3-chloro benzene sulfonamide;
(34) N-(3-(3-(9H-purin-6-yl)pyridin-2-yl amino)-2,4-difluorophenyl)-2,3-chloro benzene sulfonamide;
(35) N-(3-(3-(9H-purin-6-yl)pyridin-2-yl amino)-2,4-difluorophenyl)benzene sulfonamide;
(36) N-(3-(3-(9H-purin-6-yl)pyridin-2-yl amino)-2,4-difluorophenyl)-2,3-dihydrobenzofuran-7-sulfonamide;
(37) N-(3-(3-(9H-purin-6-yl)pyridin-2-yl amino)-2,4-difluorophenyl)benzofuran-7-sulfonamide;
(38) N-(3-(3-(9H-purin-6-yl)pyridin-2-yl amino)-2,4-difluorophenyl)chroman-8-sulfonamide;
(39) N-(3-(3-(9H-purin-6-yl)pyridin-2-yl amino)-2,4-difluorophenyl)-2-methylbenzo[d]thiazole-6-sulfonamide;
(40) N-(3-(3-(9H-purin-6-yl)pyridin-2-yl amino)-2,4-difluorophenyl)-1-methyl-1H-indole-5-sulfonamide;
(41) N-(3-(3-(9H-purin-6-yl)pyridin-2-yl amino)-2,4-difluorophenyl)-1-methyl-1H-indole-4-sulfonamide;
(42) N-(3-(3-(9H-purin-6-yl)pyridin-2-yl amino)-2,4-difluorophenyl)-1-methyl-1H-indole-7-sulfonamide;
(43) N-(3-(3-(9H-purin-6-yl)pyridin-2-yl amino)-2,4-difluorophenyl)-1-methyl-1H-pyrazole-4-sulfonamide; or
(44) N-(3-(3-(9H-purin-6-yl)pyridin-2-yl amino)-2,4-difluorophenyl)-5-chlorothiophene-4-sulfonamide.

TABLE 1
| Formula | Structure |
|---|---|
| 1 | 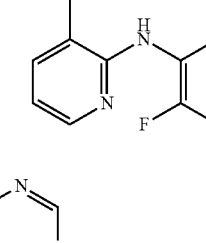 |
| 2 | 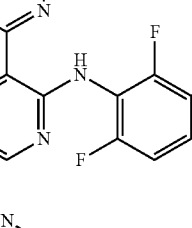 |
| 3 | 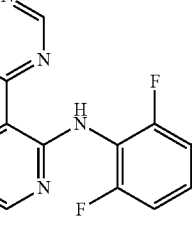 |
| 4 | 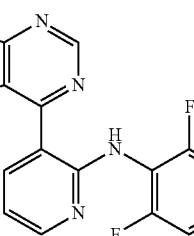 |
| 5 | 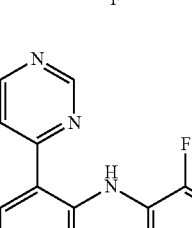 |
| 6 | 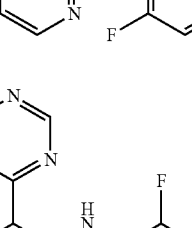 |

TABLE 1-continued

| Formula | Structure |
| --- | --- |
| 7 | (9H-purin-6-yl)pyridin-3-yl substituted 2,4-difluorophenyl benzofuran-2-sulfonamide |
| 8 | (9H-purin-6-yl)pyridin-3-yl substituted 2,4-difluorophenyl 4-chloro-2-fluorobenzenesulfonamide |
| 9 | (9H-purin-6-yl)pyridin-3-yl substituted 2,4-difluorophenyl (2-nitrophenyl)methanesulfonamide |
| 10 | (9H-purin-6-yl)pyridin-3-yl substituted 2,4-difluorophenyl 3,4-dimethoxybenzenesulfonamide |
| 11 | (9H-purin-6-yl)pyridin-3-yl substituted 2,4-difluorophenyl cyclohexanesulfonamide |
| 12 | (9H-purin-6-yl)pyridin-3-yl substituted 2,4-difluorophenyl 4-(trifluoromethoxy)benzenesulfonamide |

TABLE 1-continued
| Formula | Structure |
|---|---|
| 13 | 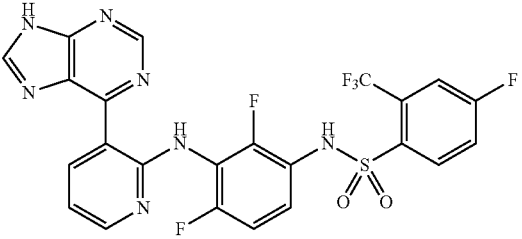 [SMILES: O=S(=O)(Nc1ccc(F)c(Nc2ncccc2-c2ncnc3[nH]cnc23)c1F)c1ccc(F)cc1C(F)(F)F] |
| 14 | 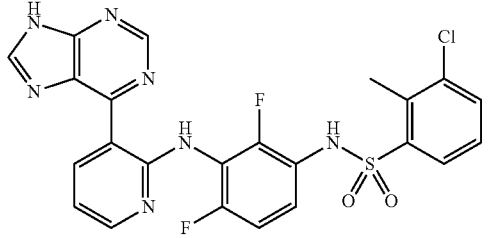 [SMILES: Cc1c(Cl)cccc1S(=O)(=O)Nc1ccc(F)c(Nc2ncccc2-c2ncnc3[nH]cnc23)c1F] |
| 15 | 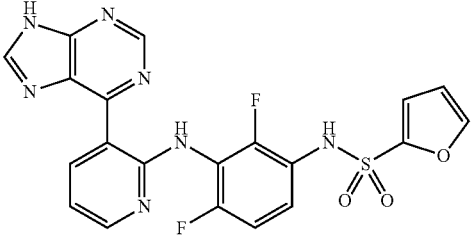 [SMILES: O=S(=O)(Nc1ccc(F)c(Nc2ncccc2-c2ncnc3[nH]cnc23)c1F)c1ccco1] |
| 16 | 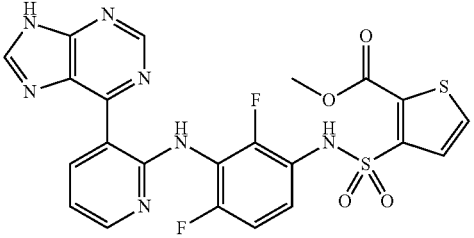 [SMILES: COC(=O)c1sccc1S(=O)(=O)Nc1ccc(F)c(Nc2ncccc2-c2ncnc3[nH]cnc23)c1F] |
| 17 | 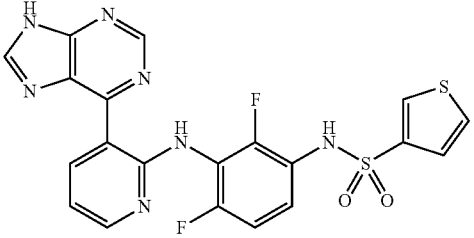 |
| 18 | 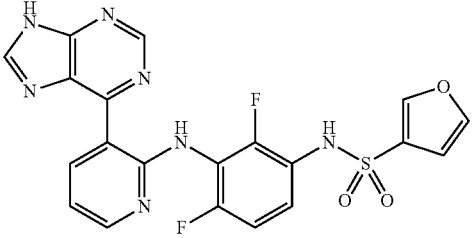 [SMILES: O=S(=O)(Nc1ccc(F)c(Nc2ncccc2-c2ncnc3[nH]cnc23)c1F)c1ccsc1] |

TABLE 1-continued
| Formula | Structure |
|---|---|
| 19 | 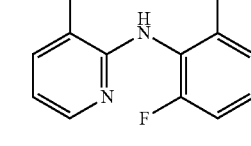 |
| 20 | 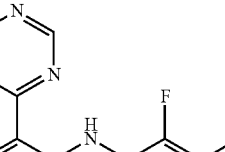 |
| 21 | 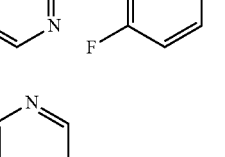 |
| 22 | 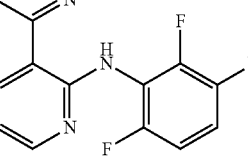 |
| 23 | 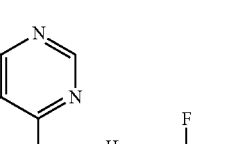 |
| 24 | 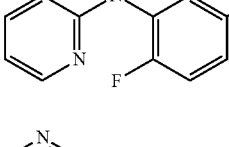 |

TABLE 1-continued

| Formula | Structure |
|---|---|
| 25 | 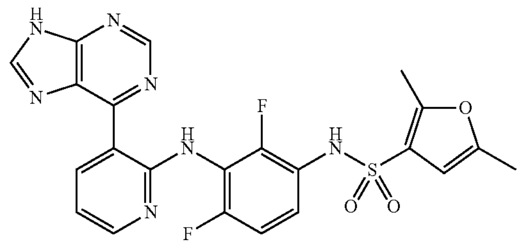 [SMILES: Cc1cc(S(=O)(=O)Nc2ccc(F)c(Nc3ncccc3-c3ncnc4[nH]cnc34)c2F)c(C)o1] |
| 26 | 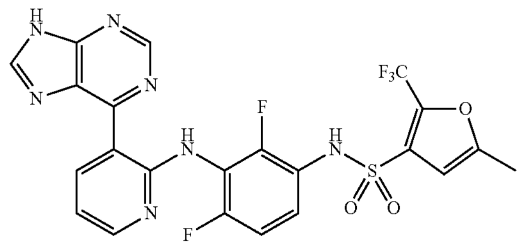 [SMILES: Cc1cc(S(=O)(=O)Nc2ccc(F)c(Nc3ncccc3-c3ncnc4[nH]cnc34)c2F)c(C(F)(F)F)o1] |
| 27 | 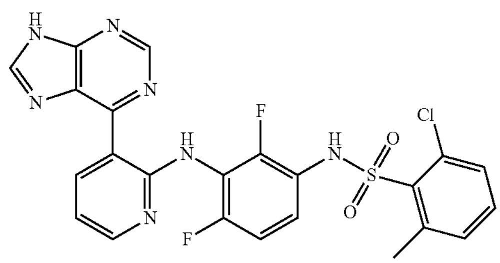 [SMILES: Cc1cccc(Cl)c1S(=O)(=O)Nc1ccc(F)c(Nc2ncccc2-c2ncnc3[nH]cnc23)c1F] |
| 28 | 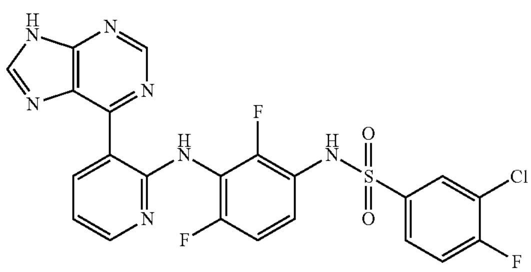 [SMILES: O=S(=O)(Nc1ccc(F)c(Nc2ncccc2-c2ncnc3[nH]cnc23)c1F)c1ccc(F)c(Cl)c1] |
| 29 | 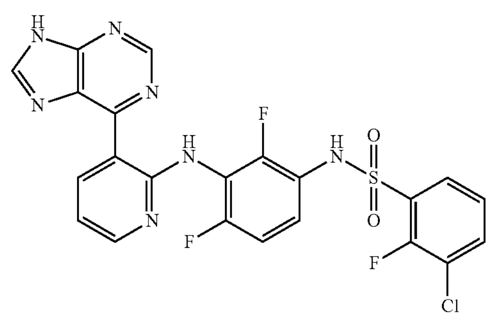 [SMILES: O=S(=O)(Nc1ccc(F)c(Nc2ncccc2-c2ncnc3[nH]cnc23)c1F)c1cccc(Cl)c1F] |
| 30 | 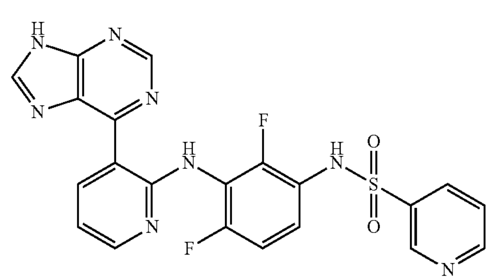 [SMILES: O=S(=O)(Nc1ccc(F)c(Nc2ncccc2-c2ncnc3[nH]cnc23)c1F)c1cccnc1] |

TABLE 1-continued
| Formula | Structure |
|---|---|
| 31 | 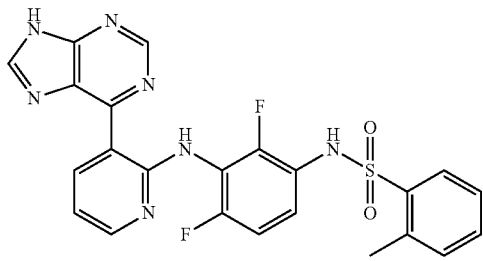 [SMILES: Cc1ccccc1S(=O)(=O)Nc1ccc(F)c(Nc2ncccc2-c2ncnc3[nH]cnc23)c1F] |
| 32 | 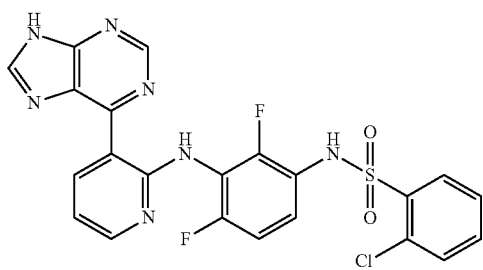 [SMILES: O=S(=O)(Nc1ccc(F)c(Nc2ncccc2-c2ncnc3[nH]cnc23)c1F)c1ccccc1Cl] |
| 33 | 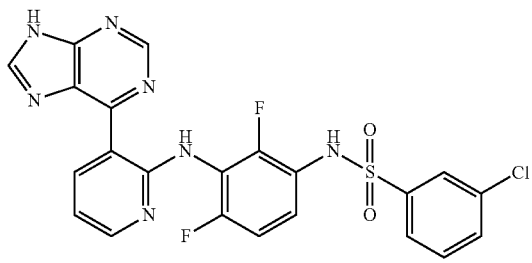 [SMILES: O=S(=O)(Nc1ccc(F)c(Nc2ncccc2-c2ncnc3[nH]cnc23)c1F)c1cccc(Cl)c1] |
| 34 | 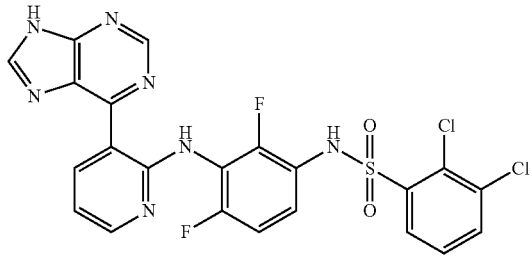 [SMILES: O=S(=O)(Nc1ccc(F)c(Nc2ncccc2-c2ncnc3[nH]cnc23)c1F)c1cccc(Cl)c1Cl] |
| 35 | 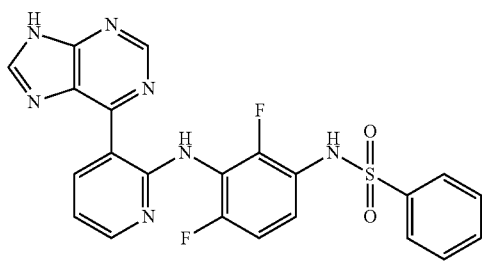 [SMILES: O=S(=O)(Nc1ccc(F)c(Nc2ncccc2-c2ncnc3[nH]cnc23)c1F)c1ccccc1] |

TABLE 1-continued

| Formula | Structure |
|---|---|
| 36 | 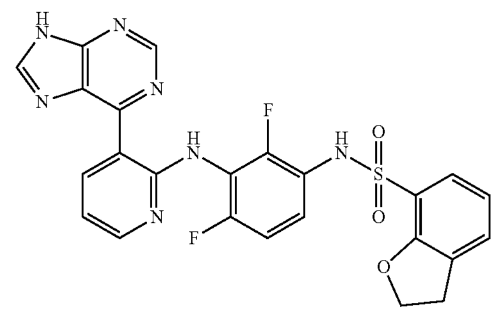 [SMILES: O=S(=O)(Nc1ccc(F)c(Nc2ncccc2-c2ncnc3[nH]cnc23)c1F)c1cccc2c1OCC2] |
| 37 | 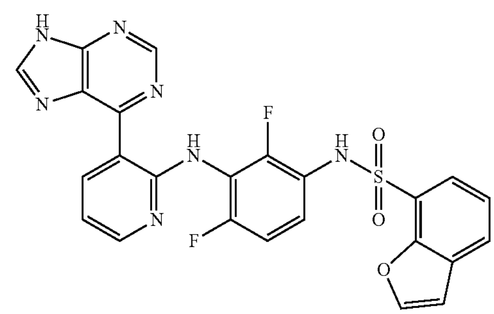 [SMILES: O=S(=O)(Nc1ccc(F)c(Nc2ncccc2-c2ncnc3[nH]cnc23)c1F)c1cccc2ccoc12] |
| 38 | 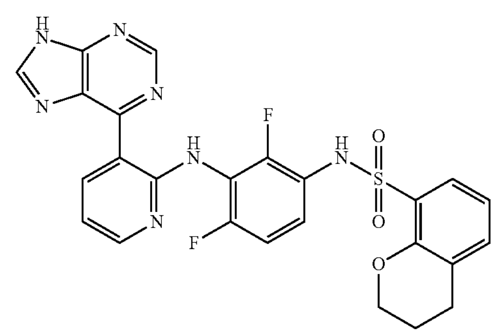 [SMILES: O=S(=O)(Nc1ccc(F)c(Nc2ncccc2-c2ncnc3[nH]cnc23)c1F)c1cccc2c1OCCC2] |
| 39 | 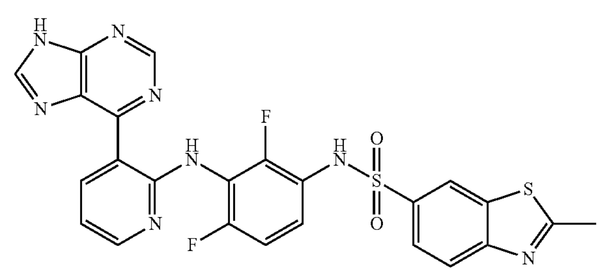 [SMILES: Cc1nc2ccc(S(=O)(=O)Nc3ccc(F)c(Nc4ncccc4-c4ncnc5[nH]cnc45)c3F)cc2s1] |
| 40 | 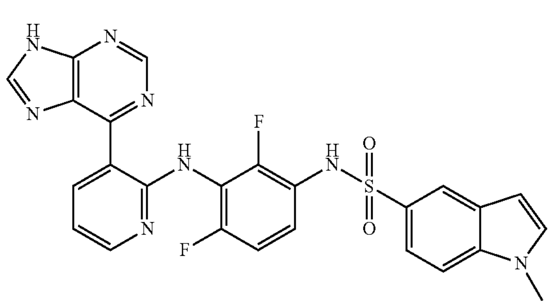 [SMILES: Cn1ccc2cc(S(=O)(=O)Nc3ccc(F)c(Nc4ncccc4-c4ncnc5[nH]cnc45)c3F)ccc21] |

TABLE 1-continued

| Formula | Structure |
|---|---|
| 41 | 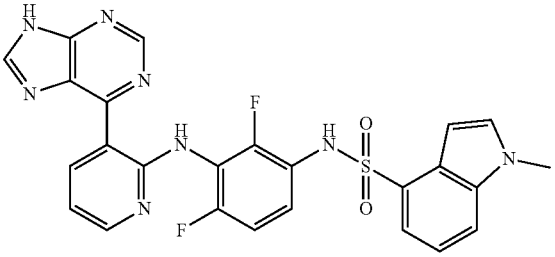 [SMILES: Cn1ccc2c(S(=O)(=O)Nc3ccc(F)c(Nc4ncccc4-c4ncnc5[nH]cnc45)c3F)cccc21] |
| 42 | 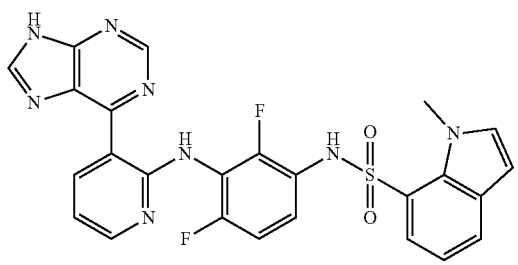 [SMILES: Cn1ccc2cccc(S(=O)(=O)Nc3ccc(F)c(Nc4ncccc4-c4ncnc5[nH]cnc45)c3F)c21] |
| 43 | 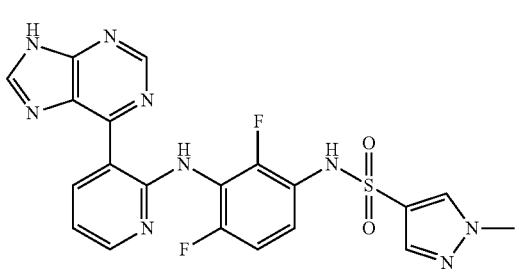 [SMILES: Cn1cc(S(=O)(=O)Nc2ccc(F)c(Nc3ncccc3-c3ncnc4[nH]cnc34)c2F)cn1] |
| 44 | 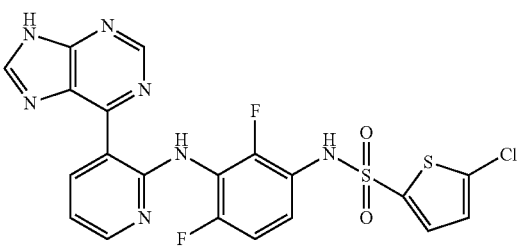 [SMILES: O=S(=O)(Nc1ccc(F)c(Nc2ncccc2-c2ncnc3[nH]cnc23)c1F)c1ccc(Cl)s1] |

The purinylpyridinylamino-2,4-difluorophenyl sulfonamide derivatives represented by Formula 1 of the present invention can be used in a form of pharmaceutically acceptable salts, and acid addition salts, which are formed by pharmaceutically acceptable free acid, may be useful for the salts. The pharmaceutically acceptable salts means organic or inorganic addition salts of the base compound of Formula 1, whose concentration is relatively non-toxic and harmless to a patient and activates effectively and whose side effects do not weaken the efficiency of the base compound of Formula 1. Inorganic and organic acids can be used as free acid for the salts. As the inorganic acid, the following acids can be used—hydrochloric acid, bromic acid, nitric acid, sulfuric acid, perchloric acid, phosphoric acid, etc. As the organic acid, the following acids can be used—citric acid, acetic acid, lactic acid, maleic acid, fumaric acid, gluconic acid, methane sulfonic acid, glycolic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, or malonic acid. In addition, the salts contain alkali metal salts (sodium salts, potassium salts, etc.) and alkaline earth metal salts (calcium salts, magnesium salts, etc.). For example, the following can be included as the acid addition salts: acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 2-napsylate, nicotinate, nitrate, orotate, oxalate, palmitate, pamoate, phosphate/hydrogen, phosphate/dihydrogen, phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc. Among these mentioned above, hydrochloride or trifluoroacetate is preferable.

Further, the purinylpyridinylamino-2,4-difluorophenyl sulfonamide derivatives represented by Formula 1 of the present invention contain all the salts, isomers, hydrates, and solvates that can be prepared by a conventional method, as well as the pharmaceutically acceptable salts.

The addition salts according to the present invention can be prepared by a conventional method. For example, the salts can be prepared by dissolving the compound of Formula 1 in water-miscible organic solvents such as acetone, methanol, ethanol, or acetonitrile, and applying a large amount of organic acid or applying acid solution of inorganic acid, precipitating or crystallizing, and evaporating the solvent of the mixture above or the large amount of acid, and then drying, or absorbing and filtering the precipitated salts.

As shown in Reaction Formula 1 below, the present invention provides a method for preparing the purinylpyridinylamino-2,4-difluorophenyl sulfonamide derivative presented in Claim 1, which includes the step of reacting the compound of Formula 2 with the compound of Formula 3 in a base and solvent to obtain the compound of Formula 1.

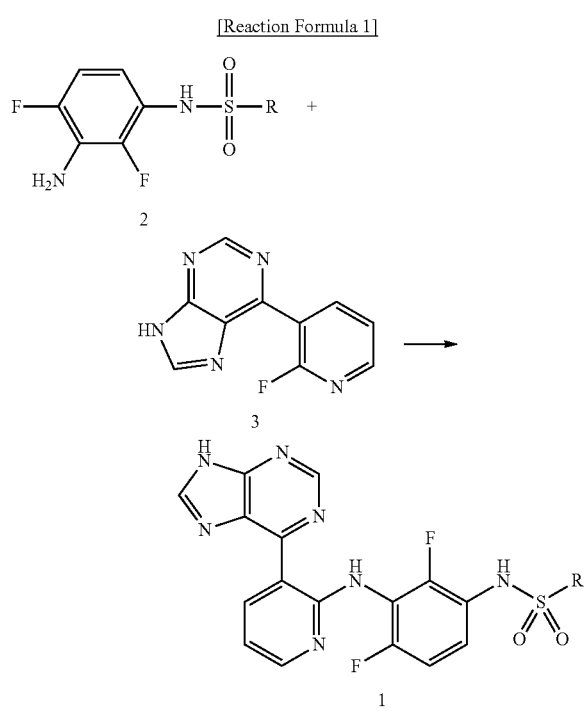

(In the Reaction Formula 1 above, R is the same as defined in Formula 1.)

For the preparation method of the present invention, the base is lithium (bistrimethylsilyl) amide and tetrahydrofuran can be used as the solvent.

To be specific, the purinylpyridinylamino-2,4-difluorophenyl sulfonamide derivative of Formula 1 can be prepared by adding and dissolving the compound of Formula 2 and the compound of Formula 3 into tetrahydrofuran as the solvent and applying lithium (bistrimethylsilyl) amide as the base slowly at 0° C., and then stirring at room temperature for 1 hour.

As shown in Reaction Formula 2 below, the present invention provides a method for preparing the purinylpyridinylamino-2,4-difluorophenyl sulfonamide derivative presented in Claim 1, which includes the step of reacting the compound of Formula 4 with the sulfonyl compound of Formula 5 in a base and solvent to obtain the compound of Formula 1.

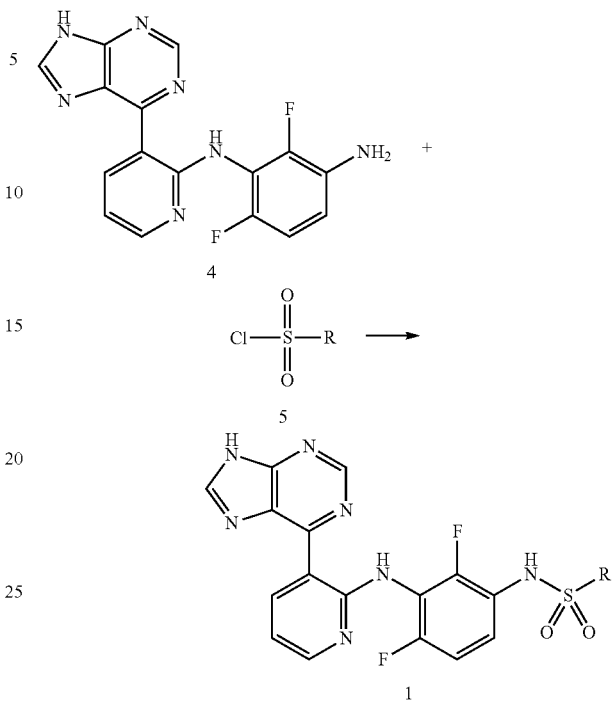

(In the Reaction Formula 2 above, R is the same as defined in Formula 1.)

For the preparation method, the base is pyridine and dichloromethane can be used as the solvent.

To be specific, the compound of Formula 1 can be prepared by adding the compound of Formula 4, the sulfonyl compound of Formula 5, and pyridine as the base into dichloromethane as the solvent and stirring at 50° C. for 2 hours.

Furthermore, the present invention provides a pharmaceutical composition, which contains the purinylpyridinylamino-2,4-difluorophenyl sulfonamide derivative represented by Formula 1 or pharmaceutically acceptable salt thereof as an active ingredient, for the prevention or treatment of the diseases caused by over-activity of Raf kinase.

Disease caused by the over-activity of the Raf kinase include cancers—melanoma, colorectal cancer, prostate cancer, thyroid cancer, and ovarian cancer.

As the Raf protein, there are three differently functioning isoforms—A-Raf, B-Raf, and C-Raf (Biochim. Biophys. Acta., 2003, 1653, 25~40). Among these, B-Raf plays a key role in connecting the signal transduction from Ras to MEK. According to the research results revealed so far, B-Raf is an important isoform protein related to cell proliferation and an important target of the oncogenic Ras. Abnormal mutations in the body have been found only in B-Raf. The mutations have been found in malignant cutaneous melanoma at an incidence of 30~60% (Nature, 2002, 417, 949~954), thyroid cancer at 30~50%, colorectal cancer at 5~20%, and ovarian cancer at 30% or less (Nature Rev. Mol. Cell Biology, 2004, 5, 875~885). The mutated B-Raf protein is transformed in NIH3T3 cells (Nature, 2002, 417, 949~954) and melanophores (Cancer Res., 2004, 64, 2338~2342), and is vital in survival and transformation of melanoma (Cancer Res., 2003, 63, 5198~5202). The mutations are considered to increase the kinase activity of B-Raf and transmit Raf/MEK/ERK signals to a downstream signaling pathway including the structural activity of ERK as a result of the activation of Ras and growth factor receptors.

As a result of measuring B-Raf kinase activity and B-Raf cell activity of the purinylpyridinylamino-2,4-difluorophenyl sulfonamide derivative represented by Formula 1 according to the present invention, it was found that the derivative had a desirable inhibitory activity against B-Raf kinase (refer to Experimental Example 1), and showed a desirable inhibitory activity against B-Raf cell activity in the in vitro experiment (refer to Experimental Example 2).

Therefore, the purinylpyridinylamino-2,4-difluorophenyl sulfonamide derivative according to the present invention can be useful for prevention and treatment of the diseases that can be induced by over-activity of Raf kinase as the derivative has been found to have a desirable inhibitory activity against B-Raf kinase and B-Raf cell activity that can cause the over-activation of Raf kinase.

In the case of using the composition of the present invention as a medicine, a pharmaceutical composition containing the purinylpyridinylamino-2,4-difluorophenyl sulfonamide derivative represented by Formula 1 or pharmaceutically acceptable salts thereof as an active ingredient can be formulated and administered clinically in various oral or parenteral forms described below, but not limited thereto.

Formulations for oral administration are tablets, pills, hard/soft capsules, liquids, suspensions, emulsifiers, syrups, granules, elixirs, etc. These formulations contain diluents (e.g. lactose, dextrose, sucrose, mannitol, sorbitol, cellulose, and/or glycine) and slip modifiers (e.g. silica, talc, stearic acid, and magnesium or calcium salts thereof, and/or polyethylene glycol) as well as the active ingredients. The tablets can contain such binders as magnesium aluminum silicate, starch paste, gelatin, methyl cellulose, sodium carboxy methyl cellulose, and/or polyvinyl pyrrolidine, and in some cases, can contain disintegrants or boiling mixtures and/or absorbents, colorants, flavoring agent, and sweeteners such as starch, agar, alginic acid, or sodium salts thereof.

The pharmaceutical composition containing the derivative represented by Formula 1 as an active ingredient can be administered parenterally. The parenteral administration can be performed by means of subcutaneous injection, intravenous injection, intramuscular injection, or intrathoracic injection.

Formulations for the parenteral administration can be prepared by mixing the purinylpyridinylamino-2,4-difluorophenyl sulfonamide derivative of Formula 1 or pharmaceutically acceptable salts thereof with stabilizer or buffer in water to formulate solution or suspension, in an ampoule or vial unit. The composition can be sterilized and/or can contain aids such as antiseptic, stabilizer, wettable powder or emulsifier, salts for osmoregulation, and/or buffer, and other therapeutically useful substances. And the formulations can be made through a conventional method of mixing, granulating, or coating.

The compounds of the present invention can be administered to the human body with different doses according to age, weight, and sex of a patient, administration pathway, physical condition of a patient, and severity of disease. For example, based on an adult patient weighed in at 70 kg, a general dose is 0.1~1,000 mg per day and a desirable dose is 1~500 mg per day. The compounds can also be administered once or several times a day at regular intervals, according to prescription by doctors or pharmacists.

Further, the present invention provides a health food composition for prevention or improvement of the diseases that can be induced by over-activity of Raf kinase, which contains the purinylpyridinylamino-2,4-difluorophenyl sulfonamide derivative represented by Formula 1 and pharmaceutically acceptable salts thereof as an active ingredient.

The disease caused by the over-activity of the Raf kinase may include cancers—melanoma, colorectal cancer, prostate cancer, thyroid cancer, and ovarian cancer.

The purinylpyridinylamino-2,4-difluorophenyl sulfonamide derivatives can be added to make various kinds of health supplement food and beverage for the purpose of preventing or improving the diseases induced by over-activity of Raf kinase as the compositions according to the present invention can function as an inhibitor against the over-activity of the Raf kinase.

There is no limit as to the kinds of the food and beverage. The foods to which the substance can be added include drinks, meat, sausage, bread, biscuit, rice cake, chocolate, candies, snacks, confectionery, pizza, instant noodles, other noodles, gums, dairy products including ice creams, soups, beverages, alcoholic beverages, vitamin complex, milk products, processed dairy products, etc. In general, the foods encompass all the health functional foods.

The purinylpyridinylamino-2,4-difluorophenyl sulfonamide derivatives of the present invention can be added to foods as it is or used together with other foods and food ingredients, and also used properly according to conventional methods. The amount of the active ingredients to be mixed can be properly determined based on the purpose of use (prevention or improvement). Generally, the compounds can be added into a health food with 01.~90 PBW of the total weight of the food. In the case of long-term intake for the purpose of health, hygiene, and health care, the amount can be reduced to less than the PBW range. However, the active ingredients can be used with the amount higher than the range as there is no problem in terms of safety.

For the composition of the health functional beverages of the present invention, the compounds can be used as an essential constituent at the ratio instructed herein, but other constituents can also be used with no specific limitations. As in other conventional beverages, various flavoring agents or natural carbohydrate can be added. Examples of the natural carbohydrate are saccharides including monosaccharide (e.g. glucose, fructose, etc.), disaccharide (e.g. maltose, sucrose, etc.), and polysaccharide (e.g. dextrin, cyclodextrin, etc.), and sugar alcohols including xylitol, sorbitol, and erythritol. Other flavoring agents including natural flavoring agents (thaumatin, stevia extract [e.g. rebaudioside A, glycyrrhizin, etc.]) and synthetic flavoring agents (saccharin, aspartame, etc.) can also be used preferably. The ratio of the natural carbohydrate to the composition of the present invention is approximately 1~20 g per 100 of the composition, and more desirably is approximately 5~12 g.

Other than these mentioned above, the purinylpyridinylamino-2,4-difluorophenyl sulfonamide derivatives of the present invention can contain carbonation agents used for various nutritional supplements, vitamins, minerals (electrolyte), synthetic and natural flavoring agents, colorants and extenders (cheese, chocolate, etc.), pectic acid and the salts thereof, alginic acid and the salts thereof, organic acid, protective colloid thickening agents, pH controlling agents, stabilizers, antiseptic, glycerin, alcohol, and carbonated drinks. Besides, the purinylpyridinylamino-2,4-difluorophenyl sulfonamide derivatives of the present invention can contain pulp to make natural fruit juice, fruit juice and beverage, and vegetable beverage.

These constituents can be used independently or mixed together. The ratio of the additives is not significantly important, but is generally determined within the range of 0.1~20

PBW per 100 PBW of the purinylpyridinylamino-2,4-difluorophenyl sulfonamide derivatives of the present invention.

In addition, the present invention provides a method for preventing or treating the diseases induced by over-activity of Raf kinase, which includes the step of administrating the purinylpyridinylamino-2,4-difluorophenyl sulfonamide derivatives or pharmaceutically acceptable salts thereof represented by Formula 1 of the present invention to patients in need of the same.

Furthermore, the present invention provides the purinylpyridinylamino-2,4-difluorophenyl sulfonamide derivatives or pharmaceutically acceptable salts thereof represented by Formula 1, which are used for prevention or treatment of the diseases induced by over-activity of Raf kinase.

DETAILED DESCRIPTION OF EXEMPLARY EMBODIMENTS

Hereinafter, the present invention will be described in greater detail with reference to Preparation Examples, Examples, and Experimental Examples. However, the following Examples are intended only to be illustrative, and not to limit the disclosure of the present invention.

Example 1

Preparation of N-(3-(3-(9H-purin-6-yl)pyridin-2-ylamino)-2,4-difluorophenyl)propane-2-sulfonamide

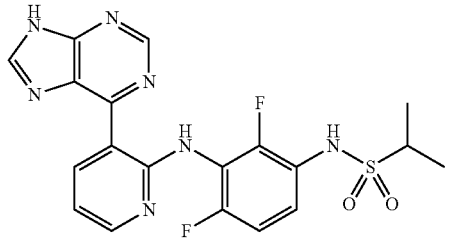 [SMILES: CC(C)S(=O)(=O)Nc1ccc(F)c(Nc2ncccc2-c2ncnc3[nH]cnc23)c1F]

Step 1: Preparation of 2,6-difluoro-3-nitro benzoic acid

Concentrated sulfuric acid (5 mL) was added into 2,6-difluoro benzoic acid (1.4 g, 9 mmol) and potassium nitrate (1 g, 9.9 mmol) was added gradually at 0° C. After the temperature of the reactant was elevated to a room temperature, the reactant was stirred for 24 hours. After pouring ice water into the reaction solution, extracting with ethylacetate, drying with sulfuric anhydride magnesium, and vacuum concentrating, the filtrate solid was washed with diethyl ether, and dried, so that 1.3 g of the target compound, 2,6-difluoro-3-nitro benzoic acid (percentage yield: 71%), was obtained.

$^1$H NMR (400 MHz, DMSO-d$_6$): δ 8.37 (td, J=9.2, 5.6 Hz, 1H), 7.46 (t, J=9.2 Hz, 1H).

Step 2: Preparation of tert-butyl-2,6-difluoro-3-nitrophenylcarbamate

The 2,6-difluoro-3-nitro benzoic acid (16 g, 79 mmol) prepared at Step 1 was added into a mixed solvent of dichloromethane and N,N-dimethylformamide and oxalyl chloride (14 mL, 158 mmol) was applied slowly. After stirring the reactant at room temperature for 18 hours and concentrating the solvent, the residuals were diluted with dichloromethane and N,N-dimethylformamide and the temperature was lowered to 0° C. Sodium azide (5.6 g, 87 mmol) was added gradually and slowly. After stirring at room temperature for 30 minutes, tert-butanol (40 mL) was applied. The reactant was refluxed and stirred for 3 hours. After the reaction, the solvent was vacuum concentrated. After the concentration, the residuals were washed with an aqueous solution of sodium hydrogen carbonate and salt water and extracted with ethylacetate, and the organic matter was concentrated and dried with sulfuric anhydride magnesium, and then refined by means of column chromatography, so that 20 g of the target compound, tert-butyl-2,6-difluoro-3-nitrophenylcarbamate (percentage yield: 93%), was obtained $^1$H NMR (400 MHz, CDCl$_3$): δ 8.00 (m, 1H), 7.08 (m, 1H), 6.46 (bs, 1H), 1.51 (s, 9H).

Step 3: Preparation of tert-butyl-3-amino-2,6-difluorophenylcarbamate

After dissolving the tert-butyl-2,6-difluoro-3-nitrophenylcarbamate (1 g, 3.6 mmol) prepared at Step 2 in methanol solvent, palladium carbon (100 mg) was added and stirred under hydrogen pressure for 15 hours. After completing the reaction, filtering through celite, vacuum concentrating, and refining by means of column chromatography, 0.76 mg of the target compound, tert-butyl-3-amino-2,6-difluorophenylcarbamate (percentage yield: 86%), was obtained.

$^1$H NMR (400 MHz, CDCl$_3$): δ 6.74 (m, 1H), 6.59 (m, 1H), 5.95 (bs, 1H), 3.62 (bs, 2H), 1.51 (s, 9H).

Step 4: Preparation of tert-butyl-2,6-difluoro-3-(1-methylethylsulfonamido)phenylcarbamate The tert-butyl-3-amino-2,6-difluorophenylcarbamate (100 mg, 0.41 mmol) prepared at Step 3 was added and dissolved into dichloromethane solvent. 2-propane sulfonyl chloride (50 uL, 0.45 mmol) and pyridine (36 uL, 0.045 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 94 mg of the target compound, tert-butyl-2,6-difluoro-3-(1-methylethylsulfonamido)phenylcarbamate (percentage yield: 65%), was obtained.

$^1$H NMR (400 MHz, CDCl$_3$): δ 7.43 (td, J=8.8, 5.6 Hz, 1H), 6.97 (bs, 1H), 6.90 (td, J=8.8, 1.6 Hz, 1H) 6.33 (bs, 1H), 3.25 (m, 1H), 1.49 (s, 9H), 1.39 (d, J=6.8 Hz, 6H).

Step 5: Preparation of N-(3-amino-2,4-difluorophenyl)propan-2-sulfonamide

The tert-butyl-2,6-difluoro-3-(1-methylethylsulfonamido) phenylcarbamate (100 mg, 0.3 mmol) prepared at Step 4 was added into ethylacetate solvent and, hydrogen chloride (4M solution in 1,4-dioxane) was applied and stirred at room temperature for 5 hours. After the reaction, the solvent was concentrated and vacuum filtrated, and the remaining solid was washed with diethyl ether and hexane and dried, so that 65 mg of the target compound, N-(3-amino-2,4-difluorophenyl)propane-2-sulfonamide (percentage yield: 91%), was obtained.

$^1$H NMR (400 MHz, CDCl$_3$): δ 6.93 (m, 1H), 6.81 (m, 1H), 6.25 (bs, 1H), 3.83 (bs, 2H), 3.28 (m, 1H), 1.42 (d, J=6.8 Hz, 6H).

Step 6: Preparation of 6-chloro-9-(tetrahydro-2H-pyran-2-yl)-9H-purine 6-chloro-9H-purine (500 mg, 3.2 mmol), 4-methyl benzene sulfonic acid (12 mg, 0.07 mmol), and 3,4-dehydro-2H-pyran (0.9 mL, 9.7 mmol) were added into ethylacetate solvent and stirred. The reactant was stirred at 90° C. for approximately 1 hour until the solid is dissolved completely. After concentrating the solvent, the residuals were refined by means of column chromatography, so that 749 mg of the target compound, 6-chloro-9-(tetrahydro-2H-pyran-2-yl)-9H-purine (percentage yield: 97%), was obtained.

$^1$H NMR (400 MHz, CDCl$_3$): δ 8.77 (s, 1H), 8.36 (s, 1H), 5.80 (dd, J=10.4, 2.8 Hz, 1H), 4.21 (m, 1H), 3.80 (m, 1H), 2.21-1.67 (m, 6H).

Step 7: Preparation 6-(2-fluoropyridin-3-yl)-9-(tetrahydro-2H-pyran-2-yl)-9H-purine The 6-chloro-9-(tetrahydro-2H-pyran-2-yl)-9H-purine (239 mg, 1 mmol) prepared at Step 6, 2-fluoropyridin-3-yl boronic acid (189 mg, 1.3 mmol), potassium acetate (216 mg, 2.2 mmol), and bis(di-tert-butyl-(4-dimethyl amino phenyl)phosphine)dichloropalladium (14 mg, 0.02 mmol) were added into a mixed solvent of ethanol and water (5/1). The reactant was refluxed and stirred under nitrogen pressure at 80° C. for 2 hours. After the reaction, the solution was concentrated and washed with water and salt water, and then extracted with ethylacetate. After drying the organic layer with sulfuric anhydride magnesium and vacuum concentrating, the residuals were refined by means of column chromatography, so that 279 mg of the target compound, 6-(2-fluoropyridin-3-yl)-9-(tetrahydro-2H-pyran-2-yl)-9H-purine (percentage yield: 93%), was obtained.

$^1$H NMR (400 MHz, CDCl$_3$): δ 9.09 (s, 1H), 8.91 (s, 1H), 8.56 (m, 1H), 8.47 (m, 1H), 7.62 (m, 1H), 5.84 (dd, J=10.8, 2.0 Hz, 1H), 4.04 (m, 1H), 3.76 (m, 1H), 2.38 (m, 1H), 2.03 (dd, J=12.8, 2.6 Hz, 2H), 1.79-1.60 (m, 3H).

Step 8: Preparation N-(2,4-difluoro-3-(3-(9-(tetrahydro-2H-pyran-2-yl)-9H-purin-6-yl)pyridin-2-yl amino)phenyl)propan-2-sulfonamide The N-(3-amino-2,4-difluorophenyl)propane-2-sulfonamide (20 mg, 0.07 mmol) prepared at Step 5 and the 6-(2-fluoropyridin-3-yl)-9-(tetrahydro-2H-pyran-2-yl)-9H-purine (19 mg, 0.063 mmol) prepared at Step 7 were added and dissolved, and lithium (bistrimethylsilyl) amide (1.0M solution in THF) was applied slowly at 0° C. After stirring the reactant at room temperature for 1 hour, completing the reaction, pouring water, and extracting with ethylacetate, the organic layer was dried with sulfuric anhydride magnesium and vacuum concentrated, and then refined by means of column chromatography, so that 25 mg of the target compound, N-(2,4-difluoro-3-(3-9-(tetrahydro-2H-pyran-2-yl)-9H-purin-6-yl)pyridin-2-yl amino)phenyl)propane-2-sulfonamide (percentage yield: 75%), was obtained.

$^1$H NMR (400 MHz, CDCl$_3$): δ 11.63 (bs, 1H), 9.67 (dd, J=8.0, 2.0 Hz, 1H), 9.03 (s, 1H), 8.38 (s, 1H), 8.26 (dd, J=4.8, 2.0 Hz, 1H), 7.46 (m, 1H), 7.01 (m, 2H), 6.41 (bs, 1H), 5.91 (dd, J=10.8, 2.4 Hz, 1H), 4.24 (m, 1H), 3.85 (m, 1H), 3.32 (m, 1H), 2.24-1.71 (m, 6H), 1.44 (d, J=6.8 Hz, 6H).

Step 9: Preparation N-(3-(3-(9H-purin-6-yl)pyridin-2-ylamino)-2,4-difluorophenyl)propane-2-sulfonamide 1M aqueous hydrochloric acid solution was added into the N-(2,4-difluoro-3-(3-9-(tetrahydro-2H-pyran-2-yl)-9H-purin-6-yl)pyridin-2-ylamino)phenyl)propane-2-sulfonamide (20 mg, 0.038 mmol) prepared at Step 8 and stirred for hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)propane-2-sulfonamide (percentage yield: 92%), was obtained.

$^1$H NMR (400 MHz, DMSO-d6): δ 11.54 (bs, 1H), 9.03 (s, 1H), 8.55 (s, 1H), 8.16 (dd, J=4.8, 1.6 Hz, 1H), 7.45 (td, J=8.8, 5.6 Hz, 1H), 7.05 (m, 2H), 3.31 (m, 1H), 1.44 (d, J=6.8 Hz, 6H).

Example 2

Preparation of N-(3-(3-(9H-purin-6-yl)pyridin-2-ylamino)-2,4-difluorophenyl)-3-(trifluoromethyl)benzenesulfonamide

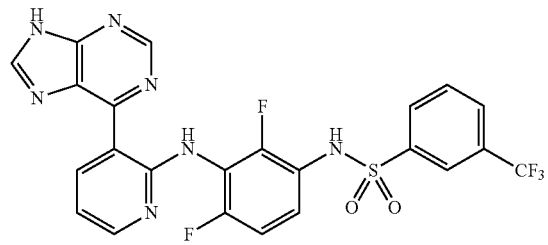 [SMILES: O=S(=O)(Nc1ccc(F)c(Nc2ncccc2-c2ncnc3[nH]cnc23)c1F)c1cccc(C(F)(F)F)c1]

Step 1 to Step 3: Preparation of tert-butyl-3-amino-2,6-difluorophenylcarbamate The same method as stated at Steps 1 to 3 of Example 1 was performed and the target compound, tert-butyl-3-amino-2,6-difluorophenylcarbamate, was obtained.

Step 4: Preparation of Benzyl tert-butyl(2,4-difluoro-1,3-phenylene)dicarbamate The tert-butyl-2,6-difluoro-3-nitrophenylcarbamate (305 mg, 1.25 mmol) prepared at Step 3, diisopropylethylamine (371 uL, 2.13 mmol), and benzyl chloroformate (194 uL, 1.38 mmol) were added into dichloromethane solvent and stirred at room temperature for 5 hours. After the reaction, the reactant was washed with water and salt water. After extraction with ethylacetate, the organic layer was dried with sulfuric anhydride magnesium and concentrated through vacuum filtration, and the residuals were refined by means of column chromatography, so that 402 mg of the target compound, benzyl tert-butyl(2,4-difluoro-1,3-phenylene)dicarbamate (percentage yield: 85%), was obtained.

$^1$H NMR (400 MHz, CDCl$_3$): δ 7.94 (bs, 1H), 7.39 (m, 5H), 6.93 (td, J=9.2, 1.6 Hz, 1H), 6.82 (bs, 1H), 5.98 (bs, 1H), 5.23 (s, 2H), 1.52 (s, 9H).

Step 5: Preparation of Benzyl 3-amino-2,4-difluorophenylcarbamate

The benzyl tert-butyl(2,4-difluoro-1,3-phenylene)dicarbamate (400 mg, 1.06 mmol) prepared at Step 4 was added into ethylacetate solvent and, hydrogen chloride (4M solution in 1,4-dioxane) was applied and stirred at room temperature for 5 hours. After the reaction, the solvent was concentrated and vacuum filtrated, and the remaining solid was washed with diethyl ether and hexane and dried, so that 276 mg of the target compound, 3-amino-2,4-difluorophenylcarbamate (percentage yield: 94%), was obtained.

$^1$H NMR (400 MHz, CDCl$_3$): δ 7.40 (m, 6H), 6.80 (dd, J=9.6, 2.0 Hz, 1H), 6.74 (bs, 1H), 5.23 (s, 2H), 3.76 (bs, 2H).

Step 6 and Step 7: Preparation of 6-(2-fluoropyridin-3-yl)-9-(tetrahydro-2H-pyran-2-yl)-9H-purine The same method as stated at Steps 6 and 7 of Example 1 was performed and the target compound, 6-(2-fluoropyridin-3-yl)-9-(tetrahydro-2H-pyran-2-yl)-9H-purine, was obtained.

Step 8: Preparation of Benzyl-2,4-difluoro-3-(3-(9-(tetrahydro-2H-pyran-2-yl)-9H-purin-6-yl)pyridin-2-ylamino)phenyl carbamate The benzyl 3-amino-2,4-difluorophenylcarbamate (100 mg, 0.32 mmol) prepared at Step 5 and the 6-(2-fluoropyridin-3-yl)-9-(tetrahydro-2H-pyran-2-yl)-9H-purine (86 mg, 0.29 mmol) prepared at Step 7 were added and dissolved, and lithium (bistrimethylsilyl) amide (1.0M solution in THF) was applied slowly at 0° C. After stirring the reactant at room temperature for 1 hour, completing the reaction, pouring water, and extracting with ethylacetate, the organic layer was dried with sulfuric anhydride magnesium and vacuum concentrated, and then refined by means of column chromatography, so that 128 mg of the target compound, benzyl-2,4-difluoro-3-(3-(9-(tetrahydro-2H-pyran-2-yl)-9H-purin-6-yl)pyridin-2-yl amino)phenyl carbamate (percentage yield: 80%), was obtained.

$^1$H NMR (400 MHz, CDCl$_3$): δ 11.57 (s, 1H), 9.66 (dd, J=8.0, 2.0 Hz, 1H), 9.02 (s, 1H), 8.39 (s, 1H), 8.28 (dd, J=4.4, 1.6 Hz, 1H), 7.92 (bs, 1H), 7.40 (m, 5H), 6.98 (m, 3H), 5.89 (dd, J=10.4, 2.4 Hz, 1H), 5.24 (s, 2H), 4.22 (m, 1H), 3.84 (m, 1H), 2.23-1.68 (m, 6H).

Step 9: Preparation of 2,6-difluoro-N$^1$-(3-(9-(tetrahydro-2H-pyran-2-yl)-9H-purin-6-yl)pyridin-2-yl)benzene-1,3-diamine After dissolving the benzyl-2,4-difluoro-3-(3-(9-(tetrahydro-2H-pyran-2-yl)-9H-purin-6-yl)pyridin-2-ylamino)phenyl carbamate (100 mg, 0.18 mmol) prepared at Step 2 in methanol solvent, palladium carbon (100 mg, 0.18 mmol) was added and stirred under hydrogen pressure for 1 hours. After completing the reaction, filtering through celite, vacuum concentrating, and refining by means of column chromatography, 51 mg of the target compound, 2,6-difluoro-N$^1$-(3-(9-(tetrahydro-2H-pyran-2-yl)-9H-purin-6-yl)pyridin-2-yl)benzene-1,3-diamine (percentage yield: 67%), was obtained.

$^1$H NMR (400 MHz, CDCl$_3$): δ 11.49 (s, 1H), 9.63 (dd, J=7.6, 1.6 Hz, 1H), 9.01 (s, 1H), 8.37 (s, 1H), 8.30 (dd, J=4.8, 1.6 Hz, 1H), 6.92 (m, 1H), 6.82 (td, J=9.2, 2.0 Hz, 1H), 6.60 (td, J=9.2, 5.2 Hz, 1H), 5.88 (dd, J=10.4, 2.4 Hz, 1H), 4.23 (m, 1H), 3.83 (m, 1H), 3.49 (bs, 2H), 2.22-1.69 (m, 6H).

Step 10: Preparation of N-(2,4-difluoro-3-(3-(9-(tetrahydro-2H-pyran-2-yl)-9H-purin-6-yl)pyridin-2-ylamino)phenyl)-3-(trifluoromethyl)benzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-(trifluoromethyl)benzene sulfonyl chloride (8 uL, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 16 mg of the target compound, N-(2,4-difluoro-3-(3-(9-(tetrahydro-2H-pyran-2-yl)-9H-purin-6-yl)pyridin-2-ylamino)phenyl)-3-(trifluoromethyl)benzenesulfonamide (percentage yield: 54%), was obtained.

$^1$H NMR (400 MHz, CDCl$_3$): δ 11.53 (s, 1H), 9.63 (d, J=7.6 Hz, 1H), 8.98 (s, 1H), 8.39 (s, 1H), 8.16 (d, J=4.8 Hz, 1H), 8.04 (s, 1H), 7.95 (d, J=8.0 Hz, 1H), 7.82 (d, J=8.0 Hz, 1H), 7.62 (d, J=8.0 Hz, 1H), 7.37 (m, 1H), 7.10 (bs, 1H), 7.01 (t, J=9.2 Hz, 1H), 7.95 (dd, J=6.8, 4.8 Hz, 1H), 5.89 (d, J=10.4 Hz, 1H), 4.24 (d, J=10.4 Hz, 1H), 3.85 (m, 1H), 2.23-1.71 (m, 6H).

Step 11: Preparation of N-(3-(3-(9H-purin-6-yl)pyridin-2-ylamino)-2,4-difluorophenyl)-3-(trifluoromethyl)benzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-3-(trifluoromethyl)benzenesulfonamide (26 mg, 0.040 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 21 mg of the target compound, N-(3-(3-(9H-purin-6-yl)pyridin-2-ylamino)-2,4-difluorophenyl)-3-(trifluoromethyl)benzenesulfonamide (percentage yield: 95%), was obtained.

$^1$H NMR (400 MHz, DMSO-d$_6$): δ 11.49 (s, 1H), 9.60 (bs, 1H), 8.50 (s, 1H), 8.06 (dd, J=4.8, 1.6 Hz, 1H), 7.97 (m, 4H), 7.21 (t, J=8.0 Hz, 1H), 7.32 (m, 1H), 7.10-7.00 (m, 2H).

Example 3

Preparation of N-(3-(3-(9H-purin-6-yl)pyridin-2-ylamino)-2,4-difluorophenyl)-4-(trifluoromethyl)benzenesulfonamide

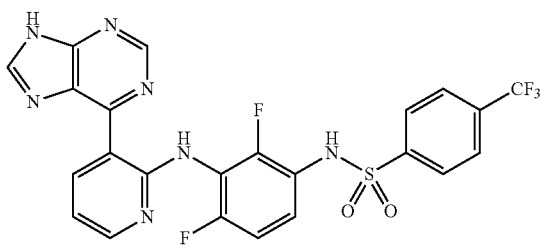 [SMILES: O=S(=O)(Nc1ccc(F)c(Nc2ncccc2-c2ncnc3[nH]cnc23)c1F)c1ccc(C(F)(F)F)cc1]

Step 1 to Step 9: Preparation of 2,6-difluoro-N$^1$-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-4-(trifluoromethyl)benzenesulfonamide The 2,6-difluoro-$N^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 4-(trifluoromethyl)benzene sulfonyl chloride (13 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 29 mg of the target compound, N-(2,4-difluoro-3-(3-(9-(tetrahydro-2H-pyran-2-yl)-9H-purin-6-yl)pyridin-2-ylamino)phenyl)-4-(trifluoromethyl)benzenesulfonamide (percentage yield: 97%), was obtained.

$^1$H NMR (400 MHz, CDCl$_3$): δ 11.50 (s, 1H), 8.97 (s, 1H), 8.39 (s, 1H), 8.15 (dd, J=4.8, 2.0 Hz, 1H), 7.93 (d, J=8.4 Hz, 2H), 7.75 (d, J=8.4 Hz, 2H), 7.43 (m, 1H), 7.02 (m, 1H), 6.95 (dd, J=8.0, 4.8 Hz, 1H), 6.80 (s, 1H), 5.89 (dd, J=10.8, 2.4 Hz, 1H), 4.24 (m, 1H), 3.85 (m, 1H), 2.23-1.71 (m, 6H).

Step 11: Preparation of N-(3-(3-(9H-purin-6-yl)pyridin-2-ylamino)-2,4-difluorophenyl)-4-(trifluoromethyl)benzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-4-(trifluoromethyl)benzenesulfonamide (26 mg, 0.040 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 19 mg of the target compound, N-(3-(3-(9H-purin-6-yl)pyridin-2-ylamino)-2,4-difluorophenyl)-4-(trifluoromethyl)benzenesulfonamide (percentage yield: 88%), was obtained.

$^1$H NMR (400 MHz, DMSO-d$_6$): δ 11.92 (bs, 1H), 11.03 (s, 1H), 9.76 (d, J=8.0 Hz, 1H), 9.26 (bs, 1H), 9.11 (s, 1H), 8.36 (s, 1H), 8.28 (dd, J=4.8, 2.0 Hz, 1H), 7.99 (d, J=8.4 Hz, 2H), 7.73 (d, J=8.4 Hz, 2H), 7.50 (m, 1H), 7.02 (m, 2H).

Example 4

Preparation of N-(3-(3-(9H-purin-6-yl)pyridin-2-ylamino)-2,4-difluorophenyl)thiophene-2-sulfonamide

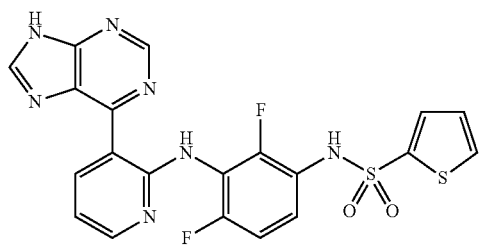 [SMILES: O=S(=O)(Nc1ccc(F)c(Nc2ncccc2-c2ncnc3[nH]cnc23)c1F)c1cccs1]

Step 1 to Step 9: Preparation of 2,6-difluoro-$N^1$-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-$N^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)thiophene-2-sulfonamide The 2,6-difluoro-$N^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-thiophenesulfonyl chloride (13 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 25 mg of the target compound, N-(2,4-difluoro-3-(3-(9-(tetrahydro-2H-pyran-2-yl)-9H-purin-6-yl)pyridin-2-ylamino)phenyl)thiophene-2-sulfonamide (percentage yield: 92%), was obtained.

$^1$H NMR (400 MHz, CDCl$_3$): δ 11.53 (s, 1H), 9.63 (dd, J=8.0, 1.6 Hz, 1H), 9.00 (s, 1H), 8.39 (s, 1H), 8.22 (dd, J=4.8, 2.0 Hz, 1H), 7.59 (dd, J=4.8, 2.0 Hz, 1H), 7.55 (dd, J=3.6, 1.2 Hz, 1H), 7.46 (m, 1H), 7.00 (m, 3H), 6.77 (s, 1H), 5.90 (dd, J=10.8, 2.4 Hz, 1H), 4.25 (m, 1H), 3.85 (m, 1H), 2.23-1.71 (m, 6H).

Step 11: Preparation of N-(3-(3-(9H-purin-6-yl)pyridin-2-ylamino)-2,4-difluorophenyl)thiophene-2-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-4-(trifluoromethyl)benzenesulfonamide (20 mg, 0.035 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 14 mg of the target compound, N-(3-(3-(9H-purin-6-yl)pyridin-2-ylamino)-2,4-difluorophenyl)thiophene-2-sulfonamide (percentage yield: 81%), was obtained.

$^1$H NMR (400 MHz, DMSO-d$_6$): δ 11.68 (bs, 1H), 9.62 (bs, 1H), 8.99 (s, 1H), 8.53 (s, 1H), 8.14 (m, 1H), 7.77 (dd, J=5.2, 1.2 Hz, 1H), 7.53 (dd, J=3.6, 1.2 Hz, 1H), 7.36 (m, 1H), 7.08 (m, 3H).

Example 5

Preparation of N-(3-(3-(9H-purin-6-yl)pyridin-2-ylamino)-2,4-difluorophenyl)propan-1-sulfonamide

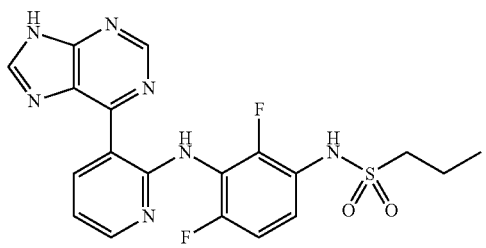 [SMILES: CCCS(=O)(=O)Nc1ccc(F)c(Nc2ncccc2-c2ncnc3[nH]cnc23)c1F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N1-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)propan-1-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 1-propansulfonyl chloride (6 uL, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 23 mg of the target compound, N-(2,4-difluoro-3-(3-(9-(tetrahydro-2H-pyran-2-yl)-9H-purin-6-yl)pyridin-2-ylamino)phenyl)propan-1-sulfonamide (percentage yield: 94%), was obtained.

$^1$H NMR (400 MHz, CDCl$_3$): δ 11.65 (s, 1H), 9.67 (dd, J=8.0, 1.6 Hz, 1H), 9.04 (s, 1H), 8.41 (s, 1H), 8.27 (dd, J=4.8, 1.6 Hz, 1H), 7.43 (m, 1H), 7.01 (m, 2H), 6.46 (s, 1H), 5.91 (dd, J=10.8, 2.0 Hz, 1H), 4.24 (m, 1H), 3.85 (m, 1H), 3.11 (m, 2H), 2.41-1.71 (m, 8H), 1.07 (t, J=7.2 Hz, 3H).

Step 11: Preparation of N-(3-(3-(9H-purin-6-yl)pyridin-2-ylamino)-2,4-difluorophenyl)propan-1-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)propan-1-sulfonamide (20 mg, 0.038 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)propan-1-sulfonamide (percentage yield: 88%), was obtained.

$^1$H NMR (400 MHz, DMSO-d$_6$): δ 11.48 (bs, 1H), 9.67 (bs, 1H), 9.03 (s, 1H), 8.55 (s, 1H), 8.17 (dd, J=4.8, 1.6 Hz, 1H), 7.42 (td, J=8.8, 5.6 Hz, 1H), 7.07 (m, 2H), 3.12 (m, 2H), 1.89 (m, 2H), 1.07 (t, J=7.2 Hz, 3H).

Example 6

Preparation of N-(3-(3-(9H-purin-6-yl)pyridin-2-ylamino)-2,4-difluorophenyl)-3,4-dichlorobenzenesulfonamide

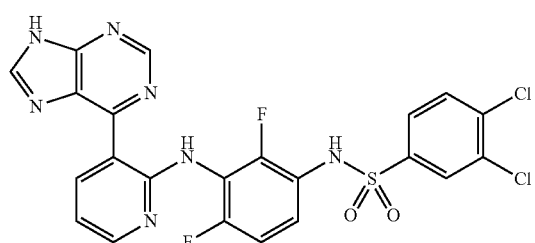

Step 1 to Step 9: Preparation of 2,6-difluoro-N$^1$-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 3,4-dichloro-N-(2,4-difluoro-3-(3-(9-(tetrahydro-2H-pyran-2-yl)-9H-purin-6-yl)pyridin-2-ylamino)phenyl)benzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3,4-dichlorobenzenesulfonyl chloride (17 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 26 mg of the target compound, 3,4-dichloro-N-(2,4-difluoro-3-(3-(9-(tetrahydro-2H-pyran-2-yl)-9H-purin-6-yl)pyridin-2-ylamino)phenyl)benzenesulfonamide (percentage yield: 89%), was obtained.

$^1$H NMR (400 MHz, CDCl$_3$): δ 11.55 (bs, 1H), 9.65 (m, 1H), 9.00 (s, 1H), 8.39 (s, 1H), 8.18 (dd, J=4.8, 1.6 Hz, 1H), 7.89 (d, J=2.0 Hz, 1H), 7.59 (m, 2H), 7.39 (m, 1H), 7.00 (m, 2H), 6.91 (s, 1H), 5.90 (dd, J=10.4, 2.4 Hz, 1H), 4.23 (m, 1H), 3.86 (m, 1H), 2.23-1.61 (m, 6H).

Step 11: Preparation of N-(3-(3-(9H-purin-6-yl)pyridin-2-ylamino)-2,4-difluorophenyl)-3,4-dichlorobenzenesulfonamide 1M aqueous hydrochloric acid solution was added into the 3,4-dichloro-N-(2,4-difluoro-3-(3-(9-(tetrahydro-2H-pyran-2-yl)-9H-purin-6-yl)pyridin-2-ylamino)phenyl)benzenesulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 14 mg of the target compound, N-(3-(3-(9H-purin-6-yl)pyridin-2-ylamino)-2,4-difluorophenyl)-3,4-dichlorobenzenesulfonamide (percentage yield: 81%), was obtained.

$^1$H NMR (400 MHz, DMSO-$d_6$): δ 11.97 (bs, 1H), 11.14 (bs, 1H), 9.78 (d, J=7.6 Hz, 1H), 9.47 (s, 1H), 9.14 (s, 1H), 8.37 (s, 1H), 8.31 (m, 1H), 7.97 (s, 1H), 7.67 (dd, J=8.4, 2.0 Hz, 1H), 7.48 (m, 2H), 7.05 (m, 2H).

Example 7

Preparation of N-(3-(3-(9H-purin-6-yl)pyridin-2-ylamino)-2,4-difluorophenyl)benzofuran-2-sulfonamide

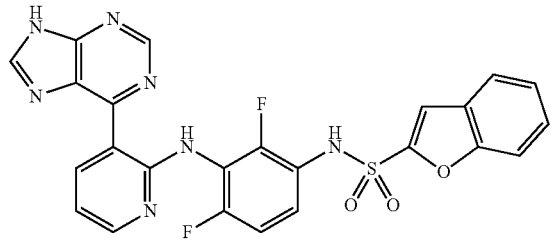 [SMILES: O=S(=O)(Nc1ccc(F)c(Nc2ncccc2-c2ncnc3[nH]cnc23)c1F)c1cc2ccccc2o1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamine)phenyl)benzofuran-2-sulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2-benzofuransulfonyl chloride (15 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 26 mg of the target compound, N-(2,4-difluoro-3-(3-(9-(tetrahydro-2H-pyran-2-yl)-9H-purin-6-yl)pyridin-2-ylamine)phenyl)benzofuran-2-sulfonamide (percentage yield: 90%), was obtained.

$^1$H NMR (400 MHz, CDCl$_3$): δ 11.51 (bs, 1H), 9.61 (dd, J=7.6, 2.0 Hz, 1H), 8.91 (s, 1H), 8.39 (s, 1H), 8.03 (dd, J=4.8, 2.0 Hz, 1H), 7.68-7.33 (m, 7H), 6.94 (m, 2H), 5.88 (dd, J=10.8, 2.4 Hz, 1H), 4.25 (m, 1H), 3.84 (m, 1H), 2.23-1.61 (m, 6H).

Step 11: Preparation of N-(3-(3-(9H-purin-6-yl)pyridin-2-ylamino)-2,4-difluorophenyl)benzofuran-2-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamine)phenyl)benzofuran-2-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 14 mg of the target compound, N-(3-(3-(9H-purin-6-yl)pyridin-2-ylamino)-2,4-difluorophenyl)benzofuran-2-sulfonamide (percentage yield: 81%), was obtained.

$^1$H NMR (400 MHz, DMSO-$d_6$): δ 11.45 (bs, 1H), 9.55 (s, 1H), 8.87 (s, 1H), 8.50 (s, 1H), 7.89 (dd, J=5.2, 2.0 Hz, 1H), 7.74 (d, J=8.4 Hz, 1H), 7.58 (d, J=8.4 Hz, 1H), 7.51-7.31 (m, 4H), 7.05 (td, J=9.2, 2.0 Hz, 1H), 6.93 (dd, J=7.6, 4.8 Hz, 1H).

Example 8

Preparation of N-(3-(3-(9H-purin-6-yl)pyridin-2-ylamino)-2,4-difluorophenyl)-4-chloro-2-fluorobenzenesulfonamide

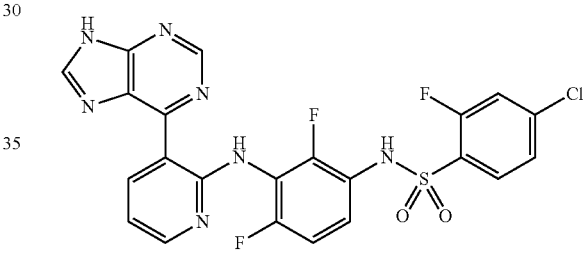

Step 1 to Step 9: Preparation of 2,6-difluoro-N$^1$-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 4-Chloro-N-(2,4-difluoro-3-(3-(9-(tetrahydro-2H-pyran-2-yl)-9H-purin-6-yl)pyridin-2-ylamino)phenyl)-2-fluorobenzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 4-chloro-2-fluorobenzenesulfonyl chloride (16 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 26 mg of the target compound, 4-chloro-N-(2, 4-difluoro-3-(3-(9-(tetrahydro-2H-pyran-2-yl)-9H-purin-6-yl)pyridin-2-ylamino)phenyl)-2-fluorobenzenesulfonamide (percentage yield: 91%), was obtained.

¹H NMR (400 MHz, CDCl₃): δ 11.52 (bs, 1H), 9.62 (dd, J=8.0, 1.6 Hz, 1H), 8.99 (s, 1H), 8.40 (s, 1H), 8.17 (dd, J=4.8, 1.6 Hz, 1H), 7.74 (m, 1H), 7.34 (m, 1H), 7.22 (m, 3H), 6.95 (m, 2H), 5.90 (dd, J=10.4, 2.0 Hz, 1H), 4.23 (m, 1H), 3.85 (m, 1H), 2.23-1.67 (m, 6H).

Step 11: Preparation of N-(3-(3-(9H-purin-6-yl)pyridin-2-ylamino)-2,4-difluorophenyl)-4-chloro-2-fluorobenzenesulfonamide 1M aqueous hydrochloric acid solution was added into the 4-chloro-N-(2,4-difluoro-3-(3-(9-(tetrahydro-2H-pyran-2-yl)-9H-purin-6-yl)pyridin-2-ylamino)phenyl)-2-fluorobenzenesulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)-4-chloro-2-fluorobenzenesulfonamide (percentage yield: 88%), was obtained.

¹H NMR (400 MHz, DMSO-d₆): δ 11.49 (bs, 1H), 9.65 (s, 1H), 8.99 (s, 1H), 8.68 (s, 1H), 8.10 (d, J=4.0 Hz, 1H), 7.71 (t, J=8.0 Hz, 1H), 7.44 (d, J=8.8 Hz, 1H), 7.13 (m, 2H), 7.01 (m, 1H).

Example 9

Preparation of N-(3-(3-(9H-purin-6-yl)pyridin-2-ylamino)-2,4-difluorophenyl)-1-(2-nitrophenyl)methansulfonamide

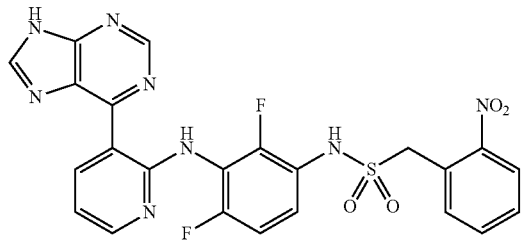 [SMILES: O=[N+]([O-])c1ccccc1CS(=O)(=O)Nc1ccc(F)c(Nc2ncccc2-c2ncnc3[nH]cnc23)c1F]

Step 1 to Step 9: Preparation of 2,6-difluoro-N¹-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-1-(2-nitrophenyl)methansulfonamide The 2,6-difluoro-N¹-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. (2-nitrophenyl)methansulfonyl chloride (12 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 25 mg of the target compound, N-(2,4-difluoro-3-(3-(9-(tetrahydro-2H-pyran-2-yl)-9H-purin-6-yl)pyridin-2-ylamino)phenyl)-1-(2-nitrophenyl)methansulfonamide (percentage yield: 87%), was obtained.

¹H NMR (400 MHz, CDCl₃): δ 11.64 (bs, 1H), 9.65 (dd, J=7.6, 1.6 Hz, 1H), 9.03 (s, 1H), 8.39 (s, 1H), 8.24 (m, 1H), 8.05 (m, 1H), 7.54 (m, 3H), 7.48 (m, 1H), 6.95 (m, 2H), 6.86 (s, 1H), 5.89 (dd, J=10.4, 2.0 Hz, 1H), 4.99 (s, 2H), 4.22 (d, J=10.4 Hz, 1H), 3.84 (m, 1H), 2.22-1.66 (m, 6H).

Step 11: Preparation of N-(3-(3-(9H-purin-6-yl)pyridin-2-ylamino)-2,4-difluorophenyl)-1-(2-nitrophenyl)methansulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-(2-nitrophenyl)methansulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 17 mg of the target compound, N-(3-(3-(9H-purin-6-yl)pyridin-2-ylamino)-2,4-difluorophenyl)-1-(2-nitrophenyl)methansulfonamide (percentage yield: 87%), was obtained.

¹H NMR (400 MHz, DMSO-d₆): δ 11.50 (bs, 1H), 9.64 (s, 1H), 9.03 (s, 1H), 8.65 (s, 1H), 8.20 (m, 1H), 8.00 (d, J=8.0 Hz, 1H), 7.70 (m, 1H), 7.62 (t, J=7.4 Hz, 2H), 7.24 (m, 1H), 7.11 (t, J=9.2 Hz, 1H), 7.01 (m, 1H), 4.85 (s, 2H).

Example 10

Preparation of N-(3-(3-(9H-purin-6-yl)pyridin-2-ylamino)-2,4-difluorophenyl)-3,4-dimethoxybenzenesulfonamide

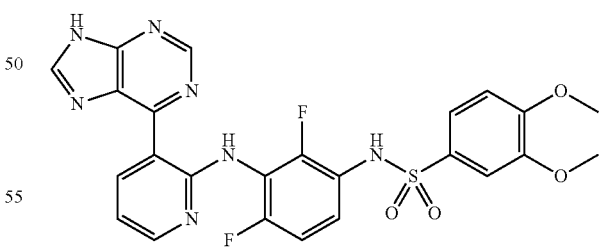

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-3,4-dimethoxybenzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3,4-dimethoxybenzenesulfonyl chloride (12 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 28 mg of the target compound, N-(2,4-difluoro-3-(3-(9-(tetrahydro-2H-pyran-2-yl)-9H-purin-6-yl)pyridin-2-ylamino)phenyl)-3,4-dimethoxybenzenesulfonamide (percentage yield: 96%), was obtained.
$^1$H NMR (400 MHz, CDCl$_3$): δ 11.45 (s, 1H), 9.59 (dd, J=8.0, 2.0 Hz, 1H), 8.95 (s, 1H), 8.35 (s, 1H), 8.16 (dd, J=4.8, 2.0 Hz, 1H), 7.40 (m, 2H), 7.16 (d, J=2.0 Hz, 1H), 6.96 (m, 2H), 6.85 (d, J=8.8 Hz, 1H), 6.76 (s, 1H), 3.90 (s, 3H), 3.84 (m, 1H), 3.81 (s, 3H), 2.21-1.63 (m, 6H).

Step 11: Preparation of N-(3-(3-(9H-purin-6-yl)pyridin-2-ylamino)-2,4-difluorophenyl)-3,4-dimethoxybenzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-3,4-dimethoxybenzenesulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 16 mg of the target compound, N-(3-(3-(9H-purin-6-yl)pyridin-2-ylamino)-2,4-difluorophenyl)-3,4-dimethoxybenzenesulfonamide (percentage yield: 16 mg), was obtained.
$^1$H NMR (400 MHz, DMSO-d$_6$): δ 11.50 (bs, 1H), 9.59 (s, 1H), 8.95 (s, 1H), 8.62 (s, 1H), 8.11 (dd, J=4.8, 2.0 Hz, 1H), 7.30 (dd, J=8.4, 2.0 Hz, 1H), 7.20 (d, J=2.0 Hz, 1H), 7.10 (m, 3H), 6.98 (m, 1H), 3.79 (s, 3H), 3.72 (s, 3H).

Example 11

Preparation of N-(3-(3-(9H-purin-6-yl)pyridin-2-ylamino)-2,4-difluorophenyl)cyclohexanesulfonamide

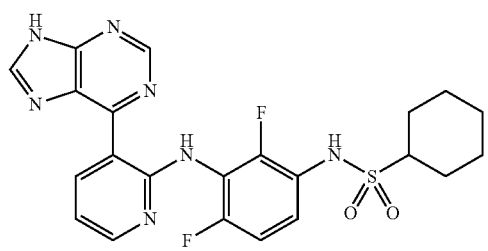 [SMILES: O=S(=O)(Nc1ccc(F)c(Nc2ncccc2-c2ncnc3[nH]cnc23)c1F)C1CCCCC1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)9H-purin-6-yl)pyridin-2-ylamino)phenyl)cyclohexanesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. cyclohexanesulfonyl chloride (10 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 24 mg of the target compound, N-(2,4-difluoro-3-(3-(9-(tetrahydro-2H-pyran-2-yl)9H-purin-6-yl)pyridin-2-ylamino)phenyl)cyclohexanesulfonamide (percentage yield: 91%), was obtained.
$^1$H NMR (400 MHz, CDCl$_3$): δ 11.63 (s, 1H), 9.67 (dd, J=8.0, 2.0 Hz, 1H), 9.04 (s, 1H), 8.40 (s, 1H), 8.26 (dd, J=4.8, 2.0 Hz, 1H), 7.45 (m, 1H), 6.99 (m, 2H), 6.46 (s, 1H), 5.90 (dd, J=10.4, 2.4 Hz, 1H), 4.24 (m, 1H), 3.85 (m, 1H), 3.02 (m, 1H), 2.23-1.23 (m, 16H).

Step 11: Preparation of N-(3-(3-(9H-purin-6-yl)pyridin-2-ylamino)-2,4-difluorophenyl)cyclohexanesulfonamide 1M aqueous hydrochloric acid solution was added into the N-(2,4-difluoro-3-(3-(9-(tetrahydro-2H-pyran-2-yl)9H-purin-6-yl)pyridin-2-ylamino)phenyl)cyclohexanesulfonamide (20 mg, 0.035 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)cyclohexanesulfonamide (percentage yield: 90%), was obtained.
$^1$H NMR (400 MHz, MeOD): δ 11.50 (bs, 1H), 9.60 (s, 1H), 9.03 (s, 1H), 8.55 (s, 1H), 8.18 (dd, J=4.8, 2.0 Hz, 1H), 7.43 (m, 1H), 7.05 (m, 2H), 3.05 (m, 1H), 2.23 (m, 2H), 1.89 (m, 2H), 1.77-1.18 (m, 6H).

Example 12

Preparation of N-(3-(3-(9H-purin-6-yl)pyridin-2-ylamino)-2,4-difluorophenyl)-4-(trifluoromethoxy)benzenesulfonamide

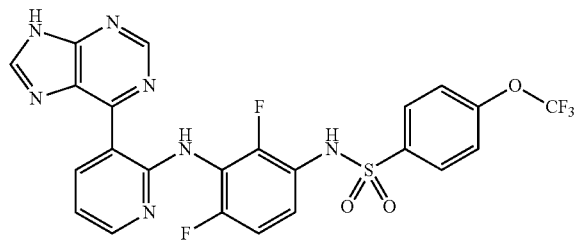 [SMILES: O=S(=O)(Nc1ccc(F)c(Nc2ncccc2-c2ncnc3[nH]cnc23)c1F)c1ccc(OC(F)(F)F)cc1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-$N^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-4-(trifluoromethoxy)benzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 4-(trifluoromethoxy)benzenesulfonyl chloride (18 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 26 mg of the target compound, N-(2,4-difluoro-3-(3-(9-(tetrahydro-2H-pyran-2-yl)-9H-purin-6-yl)pyridin-2-ylamino)phenyl)-4-(trifluoromethoxy)benzenesulfonamide (percentage yield: 87%), was obtained.

$^1$H NMR (400 MHz, CDCl$_3$): δ 11.51 (s, 1H), 9.62 (dd, J=8.0, 1.6 Hz, 1H), 8.98 (s, 1H), 8.39 (s, 1H), 8.17 (dd, J=4.8, 2.0 Hz, 1H), 7.84 (m, 2H), 7.40 (m, 1H), 7.29 (m, 2H), 6.97 (m, 3H), 5.89 (dd, J=10.4, 2.0 Hz, 1H), 4.23 (m, 1H), 3.85 (m, 1H), 2.23-1.71 (m, 6H).

Step 11: Preparation of N-(3-(3-(9H-purin-6-yl)pyridin-2-ylamino)-2,4-difluorophenyl)-4-(trifluoromethoxy)benzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-4-(trifluoromethoxy)benzenesulfonamide (20 mg, 0.031 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 16 mg of the target compound, N-(3-(3-(9H-purin-6-yl)pyridin-2-ylamino)-2,4-difluorophenyl)-4-(trifluoromethoxy)benzenesulfonamide (percentage yield: 89%), was obtained.

$^1$H NMR (400 MHz, DMSO-d$_6$): δ 11.43 (bs, 1H), 9.63 (m, 1H), 8.98 (s, 1H), 8.71 (s, 1H), 8.13 (dd, J=4.8, 2.0 Hz, 1H), 7.85 (d, J=8.4 Hz, 2H), 7.57 (d, J=8.4 Hz, 2H), 7.13 (m, 2H), 7.02 (m, 1H).

Example 13

Preparation of N-(3-(3-(9H-purin-6-yl)pyridin-2-ylamino)-2,4-difluorophenyl)-4-fluoro-2-(trifluoromethyl)benzenesulfonamide

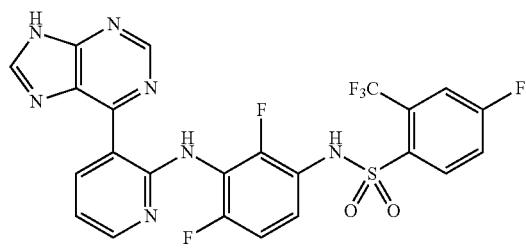 [SMILES: O=S(=O)(Nc1ccc(F)c(Nc2ncccc2-c2ncnc3[nH]cnc23)c1F)c1ccc(F)cc1C(F)(F)F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-$N^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-4-fluoro-2-(trifluoromethyl)benzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 4-fluoro-2-(trifluoromethyl)benzenesulfonyl chloride (18 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 27 mg of the target compound, N-(2,4-difluoro-3-(3-(9-(tetrahydro-2H-pyran-2-yl)-9H-purin-6-yl)pyridin-2-ylamino)phenyl)-4-fluoro-2-(trifluoromethyl)benzenesulfonamide (percentage yield: 89%), was obtained.

$^1$H NMR (400 MHz, CDCl$_3$): δ 11.45 (s, 1H), 9.59 (dd, J=7.6, 1.6 Hz, 1H), 8.96 (s, 1H), 8.37 (s, 1H), 8.12 (dd, J=4.8, 1.6 Hz, 1H), 8.00 (dd, J=9.2, 5.6 Hz, 1H), 7.56 (dd, J=9.2, 2.8 Hz, 1H), 7.39 (m, 1H), 7.40 (m, 1H), 7.26 (m, 2H), 6.87 (s, 1H), 5.87 (dd, J=10.4, 2.0 Hz, 1H), 4.20 (m, 1H), 3.82 (m, 1H), 2.21-1.62 (m, 6H).

Step 11: Preparation of N-(3-(3-(9H-purin-6-yl)pyridin-2-ylamino)-2,4-difluorophenyl)-4-fluoro-2-(trifluoromethyl)benzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-4-fluoro-2-(trifluoromethyl)benzenesulfonamide (20 mg, 0.031 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 16 mg of the target compound, N-(3-(3-(9H-purin-6-yl)pyridin-2-ylamino)-2,4-difluorophenyl)-4-fluoro-2-(trifluoromethyl)benzenesulfonamide (percentage yield: 90%), was obtained.

$^1$H NMR (400 MHz, DMSO-$d_6$): δ 11.45 (bs, 1H), 9.64 (s, 1H), 8.99 (s, 1H), 8.71 (s, 1H), 8.14 (m, 1H), 8.06 (m, 1H), 7.89 (m, 1H), 7.71 (m, 1H), 7.02 (m, 3H).

Example 14

Preparation of N-(3-(3-(9H-purin-6-yl)pyridin-2-ylamino)-2,4-difluorophenyl)-3-chloro-2-methyl benzenesulfonamide

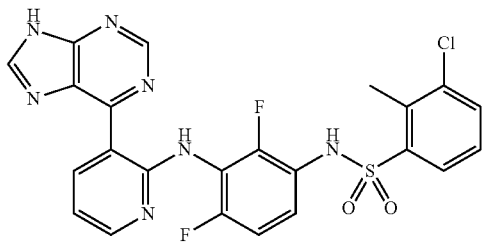 [SMILES: Cc1c(Cl)cccc1S(=O)(=O)Nc1ccc(F)c(Nc2ncccc2-c2ncnc3[nH]cnc23)c1F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 3-Chloro-N-(2,4-difluoro-3-(3-(9-(tetrahydro-2H-pyran-2-yl)-9H-purin-6-yl)pyridin-2-ylamino)phenyl)-2-methyl benzenesulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-chloro-2-methyl benzene-1-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 26 mg of the target compound, 3-chloro-N-(2,4-difluoro-3-(3-(9-(tetrahydro-2H-pyran-2-yl)-9H-purin-6-yl)pyridin-2-ylamino)phenyl)-2-methylbenzenesulfonamide (percentage yield: 90%), was obtained.

$^1$H NMR (400 MHz, CDCl$_3$): δ 11.53 (s, 1H), 9.61 (dd, J=7.6, 1.6 Hz, 1H), 8.98 (s, 1H), 8.37 (s, 1H), 8.20 (dd, J=4.8, 2.0 Hz, 1H), 7.88 (d, J=8.0 Hz, 1H), 7.56 (d, J=8.0 Hz, 1H), 7.21 (m, 2H), 7.04 (s, 1H), 6.90 (m, 2H), 5.88 (dd, J=10.4, 2.4 Hz, 1H), 4.20 (m, 1H), 3.83 (m, 1H), 2.73 (s, 3H), 2.21-1.66 (m, 6H).

Step 11: Preparation of N-(3-(3-(9H-purin-6-yl)pyridin-2-ylamino)-2,4-difluorophenyl)-3-chloro-2-methylbenzenesulfonamide 1M aqueous hydrochloric acid solution was added into the 3-chloro-N-(2,4-difluoro-3-(3-(9-(tetrahydro-2H-pyran-2-yl)-9H-purin-6-yl)pyridin-2-ylamino)phenyl)-2-methylbenzenesulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)-3-chloro-2-methylbenzenesulfonamide (percentage yield: 86%), was obtained.

$^1$H NMR (400 MHz, DMSO-$d_6$): δ 11.44 (bs, 1H), 9.63 (s, 1H), 8.99 (s, 1H), 8.71 (s, 1H), 8.13 (dd, J=4.4, 1.6 Hz, 1H), 7.76 (d, J=8.0 Hz, 1H), 7.72 (d, J=8.0 Hz, 1H), 7.37 (t, J=8.0 Hz, 1H), 7.10 (m, 2H), 7.01 (m, 1H), 2.65 (s, 3H).

Example 15

Preparation of N-(3-(3-(9H-purin-6-yl)pyridin-2-ylamino)-2,4-difluorophenyl)furan-2-sulfonamide

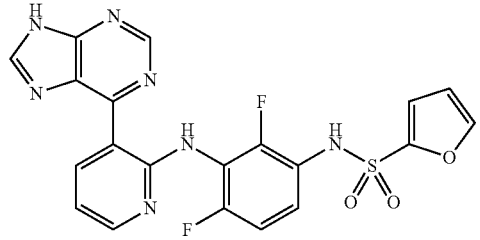

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)furan-2-sulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. furan-2-sulfonyl chloride (12 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 24 mg of the target compound, N-(2,4-difluoro-3-(3-(9-(tetrahydro-2H-pyran-2-yl)-9H-purin-6-yl)pyridin-2-ylamino)phenyl)furan-2-sulfonamide (percentage yield: 94%), was obtained.

$^1$H NMR (400 MHz, CDCl$_3$): δ 11.54 (s, 1H), 9.63 (dd, J=7.6, 1.6 Hz, 1H), 8.98 (s, 1H), 8.38 (s, 1H), 8.23 (dd, J=4.8, 2.0 Hz, 1H), 7.54 (m, 1H), 7.34 (m, 1H), 7.17 (s, 1H), 6.96 (m, 3H), 6.45 (dd, J=3.6, 2.0 Hz, 1H), 5.88 (dd, J=10.4, 2.0 Hz, 1H), 4.21 (m, 1H), 3.83 (m, 1H), 2.21-1.71 (m, 6H).

Step 11: Preparation of N-(3-(3-(9H-purin-6-yl)pyridin-2-ylamino)-2,4-difluorophenyl)furan-2-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)furan-2-sulfonamide (20 mg, 0.036 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)furan-2-sulfonamide (percentage yield: 88%), was obtained.

$^1$H NMR (400 MHz, DMSO-d$_6$): δ 11.51 (bs, 1H), 10.55 (s, 1H), 9.67 (s, 1H), 9.05 (s, 1H), 8.72 (s, 1H), 8.19 (dd, J=4.8, 1.6 Hz, 1H), 7.07 (m, 4H), 6.65 (s, 1H).

Example 16

Preparation of Methyl-3-(N-(3-(3-(9H-purin-6-yl)pyridin-2-ylamino)-2,4-difluorophenyl)sulfamoyl)thiophene-2-carboxylate

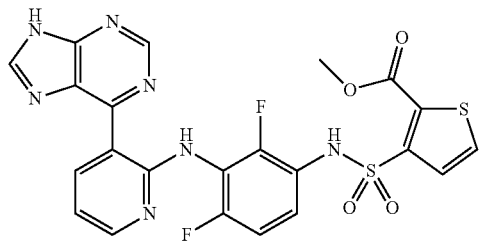 [SMILES: COC(=O)c1sccc1S(=O)(=O)Nc1ccc(F)c(Nc2ncccc2-c2ncnc3[nH]cnc23)c1F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of Methyl-3-(N-(2,4-difluoro-3-(3-(9-(tetrahydro-2H-pyran-2-yl)-9H-purin-6-yl)pyridin-2-ylamino)phenyl)sulfamoyl)thiophene-2-carboxylate The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. methyl-3-(chlorosulfonyl)thiophene-2-carboxylate (17 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 25 mg of the target compound, methyl-3-(N-(2,4-difluoro-3-(3-(9-(tetrahydro-2H-pyran-2-yl)-9H-purin-6-yl)pyridin-2-ylamino)phenyl)sulfamoyl)thiophene-2-carboxylate (percentage yield: 86%), was obtained.

$^1$H NMR (400 MHz, CDCl$_3$): δ 11.47 (s, 1H), 9.61 (dd, J=7.6, 1.6 Hz, 1H), 8.99 (s, 1H), 8.57 (s, 1H), 8.38 (s, 1H), 8.19 (dd, J=4.8, 2.0 Hz, 1H), 7.46 (m, 3H), 6.97 (m, 2H), 5.89 (dd, J=10.4, 2.4 Hz, 1H), 4.23 (m, 1H), 3.93 (s, 3H), 3.85 (m, 1H), 2.23-1.61 (m, 6H).

Step 11: Preparation of Methyl-3-(N-(3-(3-(9H-purin-6-yl)pyridin-2-ylamino)-2,4-difluorophenyl)sulfamoyl)thiophene-2-carboxylate 1M aqueous hydrochloric acid solution was added into the methyl-3-(N-(2,4-difluoro-3-(3-(9-(tetrahydro-2H-pyran-2-yl)-9H-purin-6-yl)pyridin-2-ylamino)phenyl)sulfamoyl)thiophene-2-carboxylate (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, methyl-3-(N-(3-(3-(9H-purin-6-yl)pyridin-2-ylamino)-2,4-difluorophenyl)sulfamoyl)thiophene-2-carboxylate (percentage yield: 87%), was obtained.

$^1$H NMR (400 MHz, DMSO-d$_6$): δ 11.47 (bs, 1H), 9.64 (s, 1H), 9.00 (s, 1H), 8.71 (s, 1H), 8.15 (dd, J=4.8, 1.6 Hz, 1H), 7.96 (d, J=5.2 Hz, 1H), 7.39 (d, J=5.2 Hz, 1H), 7.15 (m, 2H), 7.02 (m, 1H), 3.84 (s, 3H).

Example 17

Preparation of N-(3-(3-(9H-purin-6-yl)pyridin-2-ylamino)-2,4-difluorophenyl)thiophene-3-sulfonamide

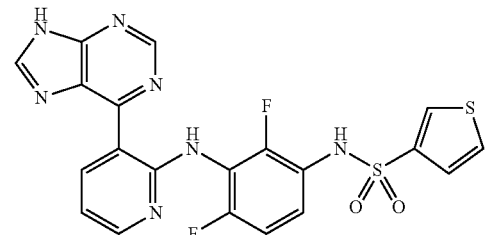

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)thiophene-3-sulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. thiophene-3-sulfonyl chloride (13 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 25 mg of the target compound, N-(2,4-difluoro-3-(3-(9-(tetrahydro-2H-pyran-2-yl)-9H-purin-6-yl)pyridin-2-ylamino)phenyl)thiophene-3-sulfonamide (percentage yield: 94%), was obtained.

¹H NMR (400 MHz, CDCl$_3$): δ 11.51 (s, 1H), 9.61 (dd, J=8.0, 2.0 Hz, 1H), 8.98 (s, 1H), 8.37 (s, 1H), 8.21 (dd, J=4.8, 2.0 Hz, 1H), 7.90 (dd, J=3.2, 1.2 Hz, 1H), 7.38 (m, 2H), 7.26 (m, 2H), 6.95 (m, 2H), 6.75 (s, 1H), 5.88 (dd, J=10.4, 2.4 Hz, 1H), 4.22 (m, 1H), 3.83 (m, 1H), 2.21-1.71 (m, 6H).

Step 11: Preparation of N-(3-(3-(9H-purin-6-yl)pyridin-2-ylamino)-2,4-difluorophenyl)thiophene-3-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)thiophene-3-sulfonamide (20 mg, 0.035 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 14 mg of the target compound, N-(3-(3-(9H-purin-6-yl)pyridin-2-ylamino)-2,4-difluorophenyl) thiophene-3-sulfonamide (percentage yield: 85%), was obtained.

¹H NMR (400 MHz, DMSO-d$_6$): δ 11.45 (bs, 1H), 9.61 (bs, 1H), 9.00 (s, 1H), 8.70 (s, 1H), 8.17 (d, J=4.4 Hz, 1H), 8.09 (m, 1H), 7.74 (m, 1H), 7.29 (d, J=5.2 Hz, 1H), 7.14 (m, 2H), 7.03 (m, 1H).

Example 18

Preparation of N-(3-(3-(9H-purin-6-yl)pyridin-2-ylamino)-2,4-difluorophenyl)furan-3-sulfonamide

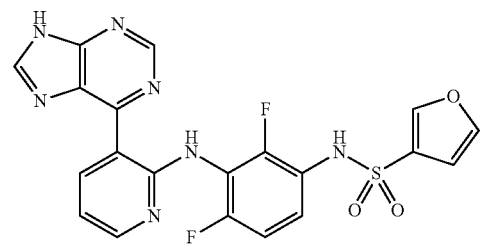

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)furan-3-sulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. furan-3-sulfonyl chloride (12 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 23 mg of the target compound, N-(2,4-difluoro-3-(3-(9-(tetrahydro-2H-pyran-2-yl)-9H-purin-6-yl)pyridin-2-ylamino)phenyl) furan-3-sulfonamide (percentage yield: 89%), was obtained.

¹H NMR (400 MHz, CDCl$_3$): δ 11.53 (s, 1H), 9.62 (dd, J=8.0, 1.6 Hz, 1H), 8.99 (s, 1H), 8.38 (s, 1H), 8.22 (dd, J=4.8, 2.0 Hz, 1H), 7.86 (s, 1H), 7.40 (m, 2H), 6.97 (m, 2H), 6.77 (s, 1H), 6.57 (s, 1H), 5.88 (dd, J=10.4, 2.4 Hz, 1H), 4.21 (m, 1H), 3.83 (m, 1H), 2.21-1.66 (m, 6H).

Step 11: Preparation of N-(3-(3-(9H-purin-6-yl)pyridin-2-ylamino)-2,4-difluorophenyl)furan-3-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)furan-3-sulfonamide (20 mg, 0.036 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 16 mg of the target compound, N-(3-(3-(9H-purin-6-yl)pyridin- 2-ylamino)-2,4-difluorophenyl)furan-3-sulfonamide (percentage yield: 92%), was obtained.

$^1$H NMR (400 MHz, DMSO-$d_6$): δ 11.49 (bs, 1H), 9.61 (m, 1H), 8.98 (s, 1H), 8.66 (s, 1H), 8.17 (m, 2H), 7.79 (m, 1H), 7.08 (s, 4H), 6.64 (s, 1H).

Example 19

Preparation of N-(3-(3-(9H-purin-6-yl)pyridin-2-ylamino)-2,4-difluorophenyl)cyclopropansulfonamide

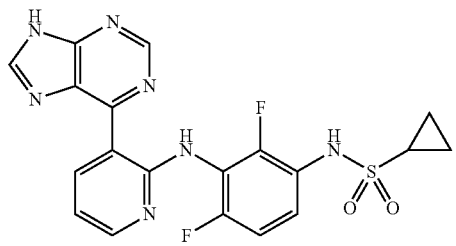 [SMILES: O=S(=O)(Nc1ccc(F)c(Nc2ncccc2-c2ncnc3[nH]cnc23)c1F)C1CC1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)9H-purin-6-yl)pyridin-2-ylamino)phenyl)cyclopropansulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. cyclopropansulfonyl chloride (10 mg, 0.052 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 24 mg of the target compound, N-(2,4-difluoro-3-(3-(9-(tetrahydro-2H-pyran-2-yl)9H-purin-6-yl)pyridin-2-ylamino)phenyl)cyclopropansulfonamide (percentage yield: 96%), was obtained.

$^1$H NMR (400 MHz, CDCl$_3$): δ 11.63 (bs, 1H), 9.67 (dd, J=7.6, 1.6 Hz, 1H), 9.04 (s, 1H), 8.41 (s, 1H), 8.25 (dd, J=4.8, 1.6 Hz, 1H), 7.43 (m, 1H), 7.02 (m, 2H), 6.47 (s, 1H), 5.91 (dd, J=10.4, 2.0 Hz, 1H), 4.23 (m, 1H), 3.85 (m, 1H), 2.53 (m, 1H) 2.24-1.71 (m, 6H), 1.20 (m, 2H), 1.17 (m, 2H).

Step 11: Preparation of N-(3-(3-(9H-purin-6-yl)pyridin-2-ylamino)-2,4-difluorophenyl)cyclopropansulfonamide 1M aqueous hydrochloric acid solution was added into the N-(2,4-difluoro-3-(3-(9-(tetrahydro-2H-pyran-2-yl)9H-purin-6-yl)pyridin-2-ylamino)phenyl)cyclopropansulfonamide (20 mg, 0.038 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 13 mg of the target compound, N-(3-(3-(9H-purin-6-yl)pyridin-2-ylamino)-2,4-difluorophenyl)cyclopropansulfonamide (percentage yield: 79%), was obtained.

$^1$H NMR (400 MHz, DMSO-$d_6$): δ 11.7 (bs, 1H), 9.66 (m, 1H), 9.03 (s, 1H), 8.71 (s, 1H), 8.20 (m, 1H), 7.30 (m, 1H), 7.03 (dd, J=8.0, 4.8 Hz, 1H), 2.64 (m, 1H), 0.90 (m, 1H).

Example 20

Preparation of N-(3-(3-(9H-purin-6-yl)pyridin-2-ylamino)-2,4-difluorophenyl)-2,4-dimethylthiazole-5-sulfonamide

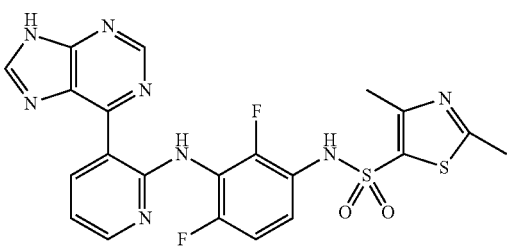 [SMILES: Cc1nc(C)c(S(=O)(=O)Nc2ccc(F)c(Nc3ncccc3-c3ncnc4[nH]cnc34)c2F)s1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-2,4-dimethylthiazole-5-sulfonamide The 2,6-difluoro-N1-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2,4-dimethylthiazole-5-sulfonyl chloride (12 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 25 mg of the target compound, N-(2,4-difluoro-3-(3-(9-(tetrahydro-2H-pyran-2-yl)-9H-purin-6-yl)pyridin-2-ylamino)phenyl)-2,4-dimethylthiazole-5-sulfonamide (percentage yield: 87%), was obtained.

$^1$H NMR (400 MHz, CDCl$_3$): δ 11.53 (s, 1H), 9.63 (dd, J=8.0, 1.6 Hz, 1H), 9.02 (s, 1H), 8.39 (s, 1H), 8.25 (dd, J=4.4, 1.6 Hz, 1H), 7.43 (m, 1H), 7.00 (m, 3H), 5.90 (dd, J=10.4, 2.4 Hz, 1H), 4.24 (m, 1H), 3.85 (m, 1H), 2.64 (s, 3H), 2.49 (s, 3H), 2.24-1.73 (m, 6H).

Step 11: Preparation of N-(3-(3-(9H-purin-6-yl)pyridin-2-ylamino)-2,4-difluorophenyl)-2,4-dimethylthiazole-5-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-2,4-dimethylthiazole-5-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 15 mg of the target compound, N-(3-(3-(9H-purin-6-yl)pyridin-2-ylamino)-2,4-difluorophenyl)-2,4-dimethylthiazole-5-sulfonamide (percentage yield: 91%), was obtained.

$^1$H NMR (400 MHz, DMSO-$d_6$): δ 13.86 (s, 1H), 11.49 (s, 1H), 10.50 (s, 1H), 9.66 (d, J=6.4 Hz, 1H), 9.02 (s, 1H), 8.72 (s, 1H), 8.19 (dd, J=4.8, 2.0 Hz, 1H), 7.19 (m, 2H), 7.04 (dd, J=8.0, 4.8 Hz, 1H), 2.60 (s, 3H), 2.34 (s, 3H).

Example 21

Preparation of N-(3-(3-(9H-purin-6-yl)pyridin-2-ylamino)-2,4-difluorophenyl)morpholine-4-sulfonamide

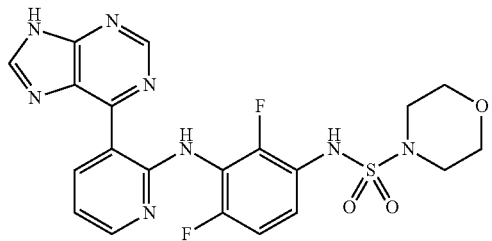 [SMILES: O=S(=O)(Nc1ccc(F)c(Nc2ncccc2-c2ncnc3[nH]cnc23)c1F)N1CCOCC1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)morpholine-4-sulfonamide The 2,6-difluoro-N$^1$-(3-(9-(tetrahydro-2H-pyran-2-yl)-9H-purin-6-yl)pyridin-2-yl)benzene-1,3-diamine (50 mg, 0.120 mmol) prepared at Step 9 was added and dissolved into dichloromethane solvent. morpholine-4-sulfonyl chloride (24 mg, 0.130 mmol) and pyridine (11 uL, 0.130 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 59 mg of the target compound, N-(2,4-difluoro-3-(3- (9-(tetrahydro-2H-pyran-2-yl)-9H-purin-6-yl)pyridin-2-ylamino)phenyl)morpholine-4-sulfonamide (percentage yield: 86%), was obtained.

$^1$H NMR (400 MHz, CDCl$_3$): δ 11.62 (s, 1H), 9.66 (dd, J=8.0, 1.6 Hz, 1H), 9.05 (s, 1H), 8.40 (s, 1H), 8.30 (dd, J=4.4, 1.6 Hz, 1H), 7.43 (m, 1H), 7.02 (m, 2H), 6.58 (bs, 1H), 5.91 (dd, J=10.4, 2.4 Hz, 1H), 4.24 (m, 1H), 3.85 (m, 1H), 3.71 (m, 2H), 3.28 (m, 2H), 2.23-1.73 (m, 6H).

Step 11: Preparation of N-(3-(3-(9H-purin-6-yl)pyridin-2-ylamino)-2,4-difluorophenyl)morpholine-4-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)morpholine-4-sulfonamide (12 mg, 0.020 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 9 mg of the target compound, N-(3-(3-(9H-purin-6-yl)pyridin-2-ylamino)-2,4-difluorophenyl)morpholine-4-sulfonamide (percentage yield: 94%), was obtained.

$^1$H NMR (400 MHz, DMSO-$d_6$): δ 13.86 (s, 1H), 11.55 (s, 1H), 9.65 (s, 1H), 9.02 (s, 1H), 8.71 (s, 1H), 8.20 (dd, J=4.8, 2.0 Hz, 1H), 7.33 (m, 1H), 7.18 (m, 1H), 7.04 (m, 1H), 3.65 (m, 2H), 3.12 (m, 2H).

Example 22

Preparation of N-(3-(3-(9H-purin-6-yl)pyridin-2-ylamino)-2,4-difluorophenyl)-1-methyl-1-imidazole-4-sulfonamide

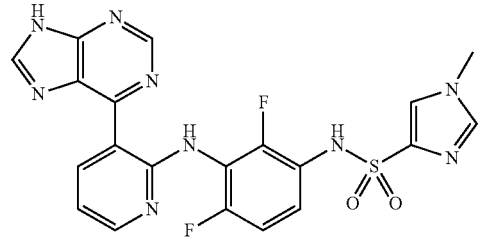

Step 1 to Step 3: Preparation of tert-butyl-3-amino-2,6-difluorophenylcarbamate

The same method as stated at Steps 1 to 3 of Example 1 was performed and the target compound, tert-butyl-3-amino-2,6-difluorophenylcarbamate, was obtained.

Step 4: Preparation of tert-butyl-2,6-difluoro-3-(1-methyl-1H-imidazole-4-sulfonamido)phenylcarbamate The tert-butyl-3-amino-2,6-difluorophenylcarbamate (50 mg, 0.20 mmol) prepared at Step 3 was added and dissolved into dichloromethane solvent. 1-methyl-1H-imidazole-4-sulfonyl chloride (44 uL, 0.25 mmol) and pyridine (50 uL, 0.61 mmol) were added into the reaction solution and stirred at 50° C. for 2 hours. After the reaction, the reactant was washed with 1N aqueous hydrochloric acid solution and salt water.

After extraction with dichloromethane, the organic layer was dried with sulfuric anhydride magnesium and vacuum concentrated, and then refined by means of column chromatography, so that 74 mg of the target compound, tert-butyl-2,6-difluoro-3-(1-methyl-1H-imidazole-4-sulfonamido)phenylcarbamate (percentage yield: 95%), was obtained.

$^1$H NMR (400 MHz, DMSO-$d_6$): δ 9.96 (bs, 1H), 8.82 (s, 1H), 7.78 (s, 1H), 7.68 (s, 1H), 7.17 (m, 1H), 7.03 (m, 1H), 3.25 (s, 3H), 1.40 (s, 9H).

Step 5: Preparation of N-(3-amino-2,4-difluorophenyl)-1-methyl-1H-imidazole-4-sulfonamide The tert-butyl-2,6-difluoro-3-(1-methyl-1H-imidazole-4-sulfonamido)phenylcarbamate (67 mg, 0.17 mmol) prepared at Step 4 was added into ethylacetate solvent and, hydrogen chloride (4M solution in 1,4-dioxane) was applied and stirred at room temperature for 5 hours. After the reaction, the solvent was concentrated and vacuum filtrated, and the remaining solid was washed with diethyl ether and hexane and dried, so that 55 mg of the target compound, N-(3-amino-2,4-difluorophenyl)-1-methyl-1H-imidazole-4-sulfonamide (percentage yield: 99%), was obtained.

$^1$H NMR (400 MHz, CDCl$_3$): δ 7.49 (s, 1H), 7.40 (s, 1H), 6.96 (bs, 1H), 6.90 (m, 1H), 6.74 (m, 1H), 3.72 (s, 3H).

Step 6 and Step 7: Preparation of 6-(2-fluoropyridin-3-yl)-9-(tetrahydro-2H-pyran-2-yl)-9H-purine The same method as stated at Steps 6 to 7 of Example 1 was performed and the target compound, 6-(2-fluoropyridin-3-yl)-9-(tetrahydro-2H-pyran-2-yl)-9H-purine, was obtained.

Step 8: Preparation of N-(2,4-difluoro-3-(3-(9-(tetrahydro-2H-pyran-2-yl)-9H-purin-6-yl)pyridin-2-ylamino)phenyl)-1-methyl-1H-imidazole-4-sulfonamide The N-(3-amino-2,4-difluorophenyl)-1-methyl-1H-imidazole-4-sulfonamide (45 mg, 0.16 mmol) prepared at Step 5 and the 6-(2-fluoropyridin-3-yl)-9-(tetrahydro-2H-pyran-2-yl)-9H-purine (43 mg, 0.14 mmol) prepared at Step 7 were added and dissolved, and lithium (bistrimethylsilyl) amide (1.0M solution in THF) was applied slowly at 0° C. After stirring the reactant at room temperature for 1 hour, completing the reaction, pouring water, and extracting with ethylacetate, the organic layer was dried with sulfuric anhydride magnesium and vacuum concentrated, and then refined by means of column chromatography, so that 65 mg of the target compound, N-(2,4-difluoro-3-(3-(9-(tetrahydro-2H-pyran-2-yl)-9H-purin-6-yl)pyridin-2-ylamino)phenyl)-1-methyl-1H-imidazole-4-sulfonamide (percentage yield: 82%), was obtained.

$^1$H NMR (400 MHz, DMSO-$d_6$): δ 11.37 (d, J=7.6 Hz, 1H), 9.97 (s, 1H), 9.60 (s, 1H), 9.09 (d, J=7.2 Hz, 1H), 8.97 (d, J=7.6 Hz, 1H), 8.20 (s, 1H), 7.77 (dd, J=21.2, 6.4 Hz, 2H), 7.21 (m, 1H), 7.06 (m, 2H), 5.88 (m, 1H), 4.15 (m, 1H), 3.91 (m, 1H), 3.67 (s, 1H), 2.35-1.12 (m, 6H).

Step 9: Preparation of N-(3-(3-(9H-purin-6-yl)pyridin-2-ylamino)-2,4-difluorophenyl)-1-methyl-1H-imidazole-4-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-methyl-1H-imidazole-4-sulfonamide (15 mg, 0.026 mmol) prepared at Step 8 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 11 mg of the target compound, N-(3-(3-(9H-purin-6-yl)pyridin-2-ylamino)-2,4-difluorophenyl)-1-methyl-1H-imidazole-4-sulfonamide (percentage yield: 88%), was obtained.

$^1$H NMR (400 MHz, DMSO-$d_6$): δ 11.52 (bs, 1H), 9.71 (bs, 1H), 9.03 (s, 1H), 8.72 (s, 1H), 8.18 (d, J=4.0 Hz, 1H), 7.80 (s, 1H), 7.66 (s, 1H), 7.22 (m, 1H), 7.10 (m, 1H), 7.03 (m, 1H), 3.68 (s, 3H).

Example 23

Preparation of N-(3-(3-(9H-purin-6-yl)pyridin-2-ylamino)-2,4-difluorophenyl)-5-methylfuran-2-sulfonamide

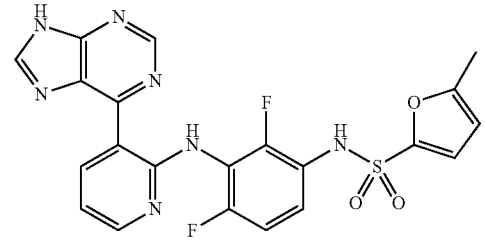 [SMILES: Cc1ccc(S(=O)(=O)Nc2ccc(F)c(Nc3ncccc3-c3ncnc4[nH]cnc34)c2F)o1]

Step 1 to step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-5-methylfuran-2-sulfonamide The 2,6-difluoro-N$^1$-(3-(9-(tetrahydro-2H-pyran-2-yl)-9H-purin-6-yl)pyridin-2-yl)benzene-1,3-diamine (50 mg, 0.120 mmol) prepared at Step 9 was added and dissolved into dichloromethane solvent. 5-methylfuran-2-sulfonyl chloride (24 mg, 0.130 mmol) and pyridine (11 uL, 0.130 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 58 mg of the target compound, N-(2,4-difluoro-3-(3-(9-(tetrahydro-2H-pyran-2-yl)-9H-purin-6-yl)pyridin-2-ylamino)phenyl)-5-methylfuran-2-sulfonamide (percentage yield: 85%), was obtained.

$^1$H NMR (400 MHz, CDCl$_3$): δ 11.56 (s, 1H), 9.65 (dd, J=7.6, 1.6 Hz, 1H), 9.01 (s, 1H), 8.39 (s, 1H), 8.25 (dd, J=4.8, 2.0 Hz, 1H), 7.38 (m, 1H), 7.13 (s, 1H), 7.00 (m, 3H), 6.47 (dd, J=3.6, 2.0 Hz, 1H), 5.90 (dd, J=10.4, 2.0 Hz, 1H), 4.23 (m, 1H), 3.85 (m, 1H), 2.41 (s, 3H), 2.24-1.84 (m, 6H).

Step 11: Preparation of N-(3-(3-(9H-purin-6-yl)pyridin-2-ylamino)-2,4-difluorophenyl)-5-methylfuran-2-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-5-methylfuran-2-sulfonamide (12 mg, 0.020 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 8 mg of the target compound, N-(3-(3-(9H-purin-6-yl)pyridin-2-ylamino)-2,4-difluorophenyl)-5-methylfuran-2-sulfonamide (percentage yield: 81%), was obtained.

$^1$H NMR (400 MHz, DMSO-$d_6$): δ 13.88 (bs, 1H), 11.53 (bs, 1H), 10.52 (s, 1H), 9.68 (d, J=7.2 Hz, 1H), 9.03 (s, 1H), 8.73 (s, 1H), 8.01 (s, 1H), 7.07 (m, 4H), 6.67 (m, 1H), 2.63 (s, 3H).

Example 24

Preparation of N-(3-(3-(9H-purin-6-yl)pyridin-2-ylamino)-2,4-difluorophenyl)-5-(1,3-dioxolane-2-yl)furan-2-sulfonamide

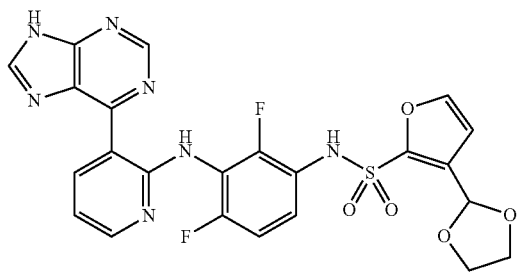 [SMILES: O=S(=O)(Nc1ccc(F)c(Nc2ncccc2-c2ncnc3[nH]cnc23)c1F)c1occc1C1OCCO1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-5-(1,3-dioxolane-2-yl)furan-2-sulfonamide The 2,6-difluoro-N$^1$-(3-(9-(tetrahydro-2H-pyran-2-yl)-9H-purin-6-yl)pyridin-2-yl)benzene-1,3-diamine (50 mg, 0.120 mmol) prepared at Step 9 was added and dissolved into dichloromethane solvent. 5-(1,3-dioxolane-2-yl)furan-2-sulfonyl chloride (24 mg, 0.130 mmol) and pyridine (11 uL, 0.130 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 71 mg of the target compound, N-(2,4-difluoro-3-(3-(9-(tetrahydro-2H-pyran-2-yl)-9H-purin-6-yl)pyridin-2-ylamino)phenyl)-5-(1,3-dioxolane-2-yl)furan-2-sulfonamide (percentage yield: 94%), was obtained.

$^1$H NMR (400 MHz, CDCl$_3$): δ 11.54 (s, 1H), 9.64 (dd, J=7.6, 1.6 Hz, 1H), 9.02 (s, 1H), 8.40 (s, 1H), 8.24 (dd, J=4.8, 2.0 Hz, 1H), 7.56 (m, 1H), 7.42 (m, 1H), 7.15 (s, 1H), 6.98 (m, 3H), 5.86 (dd, J=10.4, 2.0 Hz, 1H), 4.25 (m, 1H), 4.05 (m, 4H), 3.84 (m, 1H), 2.21-1.71 (m, 6H).

Step 11: Preparation of N-(3-(3-(9H-purin-6-yl)pyridin-2-ylamino)-2,4-difluorophenyl)-5-(1,3-dioxolane-2-yl)furan-2-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-5-(1,3-dioxolane-2-yl)furan-2-sulfonamide (12 mg, 0.020 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 9 mg of the target compound, N-(3-(3-(9H-purin-6-yl)pyridin-2-ylamino)-2,4-difluorophenyl)-5-(1,3-dioxolane-2-yl)furan-2-sulfonamide (percentage yield: 81%), was obtained.

$^1$H NMR (400 MHz, DMSO-$d_6$): δ 11.51 (bs, 1H), 10.54 (s, 1H), 9.68 (s, 1H), 9.07 (s, 1H), 8.76 (s, 1H), 8.19 (dd, J=4.8, 1.6 Hz, 1H), 8.03 (s, 1H), 7.09 (m, 4H), 4.12 (m, 4H).

Example 25

Preparation of N-(3-(3-(9H-purin-6-yl)pyridin-2-ylamino)-2,4-difluorophenyl)-2,5-dimethylfuran-3-sulfonamide

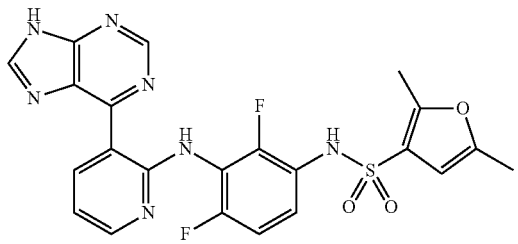 [SMILES: Cc1cc(S(=O)(=O)Nc2ccc(F)c(Nc3ncccc3-c3ncnc4[nH]cnc34)c2F)c(C)o1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-2,5-dimethylfuran-3-sulfonamide The 2,6-difluoro-N$^1$-(3-(9-(tetrahydro-2H-pyran-2-yl)-9H-purin-6-yl)pyridin-2-yl)benzene-1,3-diamine (50 mg, 0.120 mmol) prepared at Step 9 was added and dissolved into dichloromethane solvent. 2,5-다이 methylfuran-3-sulfonyl chloride (24 mg, 0.130 mmol) and pyridine (11 uL, 0.130 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 64 mg of the target compound, N-(2,4-difluoro-3-(3-(9-(tetrahydro-2H-pyran-2-yl)-9H-purin-6-yl)pyridin-2-ylamino)phenyl)-2,5-다이 methylfuran-3-sulfonamide (percentage yield: 91%), was obtained.

$^1$H NMR (400 MHz, CDCl$_3$): δ 11.57 (s, 1H), 9.65 (dd, J=8.0, 1.6 Hz, 1H), 9.02 (s, 1H), 8.40 (s, 1H), 8.25 (dd, J=4.4, 1.6 Hz, 1H), 7.42 (s, 1H), 7.04 (m, 2H), 6.69 (s, 1H), 5.90 (dd, J=10.4, 2.4 Hz, 1H), 4.23 (m, 1H), 3.85 (m, 1H), 3.02 (s, 3H), 2.73 (s, 3H), 2.26-1.71 (m, 6H).

Step 11: Preparation of N-(3-(3-(9H-purin-6-yl)pyridin-2-ylamino)-2,4-difluorophenyl)-2,5-dimethylfuran-3-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-2,5-다이 methylfuran-3-sulfonamide (12 mg, 0.020 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 9 mg of the target compound, N-(3-(3-(9H-purin-6-yl)pyridin-2-ylamino)-2,4-difluorophenyl)-2,5-다이 methylfuran-3-sulfonamide (percentage yield: 89%), was obtained.

$^1$H NMR (400 MHz, DMSO-d$_6$): δ 11.50 (bs, 1H), 9.64 (m, 1H), 9.02 (s, 1H), 8.73 (s, 1H), 8.18 (m, 1H), 7.87 (s, 1H), 7.15 (m, 3H), 7.03 (m, 1H), 3.11 (s, 3H), 2.84 (s, 3H).

Example 26

Preparation of Preparation of N-(3-(3-(9H-purin-6-yl)pyridin-2-ylamino)-2,4-difluorophenyl)-5-methyl-2-(trifluoromethyl)furan-3-sulfonamide

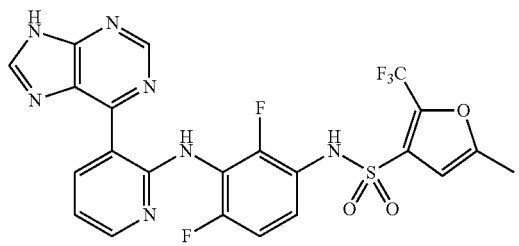 [SMILES: Cc1cc(S(=O)(=O)Nc2ccc(F)c(Nc3ncccc3-c3ncnc4[nH]cnc34)c2F)c(C(F)(F)F)o1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-5-methyl-2-(trifluoromethyl)furan-3-sulfonamide The 2,6-difluoro-N$^1$-(3-(9-(tetrahydro-2H-pyran-2-yl)-9H-purin-6-yl)pyridin-2-yl)benzene-1,3-diamine (50 mg, 0.120 mmol) prepared at Step 9 was added and dissolved into dichloromethane solvent. 5-methyl-2-(trifluoromethyl)furan-3-sulfonyl chloride (24 mg, 0.130 mmol) and pyridine (11 uL, 0.130 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that 72 mg of the target compound, N-(2,4-difluoro-3-(3-(9-(tetrahydro-2H-pyran-2-yl)-9H-purin-6-yl)pyridin-2-ylamino)phenyl)-5-methyl-2-(trifluoromethyl)furan-3-sulfonamide (percentage yield: 94%), was obtained.

$^1$H NMR (400 MHz, CDCl$_3$): δ 11.59 (s, 1H), 9.66 (dd, J=8.0, 1.6 Hz, 1H), 9.10 (s, 1H), 8.41 (s, 1H), 8.31 (dd, J=4.4, 1.6 Hz, 1H), 7.56 (s, 1H), 6.96 (m, 2H), 6.78 (s, 1H), 5.98 (dd, J=10.4, 2.4 Hz, 1H), 4.30 (m, 1H), 3.91 (m, 1H), 3.15 (s, 3H), 2.26-1.71 (m, 6H).

Step 11: Preparation of N-(3-(3-(9H-purin-6-yl)pyridin-2-ylamino)-2,4-difluorophenyl)-5-methyl-2-(trifluoromethyl)furan-3-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-5-methyl-2-(trifluoromethyl)furan-3-sulfonamide (12 mg, 0.020 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that 9 mg of the target compound, N-(3-(3-(9H-purin-6-yl)pyridin-2-ylamino)-2,4-difluorophenyl)-5-methyl-2-(trifluoromethyl)furan-3-sulfonamide (percentage yield: 85%), was obtained.

$^1$H NMR (400 MHz, DMSO-d$_6$): δ 11.66 (bs, 1H), 9.61 (m, 1H), 8.99 (s, 1H), 8.71 (s, 1H), 8.21 (m, 1H), 7.76 (s, 1H), 7.12 (m, 3H), 6.87 (m, 1H), 3.21 (s, 3H).

Example 27

Preparation of N-(3-(3-(9H-purin-6-yl)pyridin-2-ylamino)-2,4-difluorophenyl)-2-chloro-6-methylbenzenesulfonamide

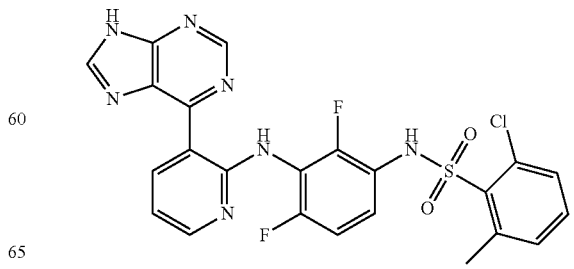

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl) benzene-1,3-diamine, was obtained.

Step 10: Preparation of 2-chloro-N-(2,4-difluoro-3-(3-(9-(tetrahydro-2H-pyran-2-yl)-9H-purin-6-yl) pyridin-2-ylamino)phenyl)-6-methylbenzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2-chloro-6-methylbenzene-1-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.51 (s, 1H), 9.62 (dd, J=7.6, 1.6 Hz, 1H), 8.98 (s, 1H), 8.38 (s, 1H), 8.18 (dd, J=4.8, 2.0 Hz, 1H), 7.58 (s, 1H), 7.38 (m, 3H), 7.17 (d, J=7.2 Hz, 1H), 6.93 (m, 2H), 5.89 (dd, J=8, 2.4 Hz, 1H), 4.22 (m, 1H), 3.84 (m, 1H), 2.63 (s, 3H), 2.21-1.70 (m, 6H).

Step 11: Preparation of N-(3-(3-(9H-purin-6-yl)pyridin-2-ylamino)-2,4-difluorophenyl)-2-chloro-6-methylbenzenesulfonamide 1M aqueous hydrochloric acid solution was added into the 2-chloro-N-(2,4-difluoro-3-(3-(9-(tetrahydro-2H-pyran-2-yl)-9H-purin-6-yl)pyridin-2-ylamino)phenyl)-6-methylbenzenesulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 12.17 (bs, 1H), 11.53 (s, 1H), 10.74 (s, 1H), 9.78 (d, J=7.6 Hz, 1H), 9.21 (s, 1H), 8.35 (s, 1H), 8.32 (d, J=2.8 Hz, 1H), 8.10 (d, J=8.0 Hz, 1H), 7.71 (d, J=8.0 Hz, 1H), 7.50 (m, 1H), 7.38 (t, J=8.0 Hz, 1H), 7.01 (m, 2H), 2.64 (s, 3H).

Example 28

Preparation of N-(3-(3-(9H-purin-6-yl)pyridin-2-ylamino)-2,4-difluorophenyl)-3-chloro-4-fluorobenzenesulfonamide

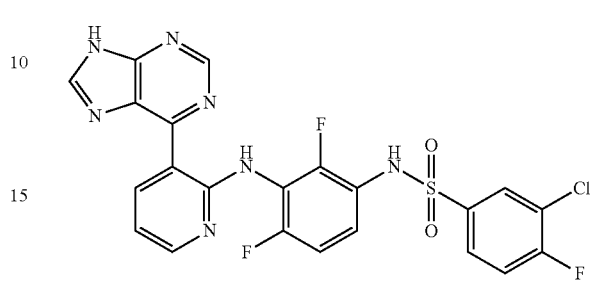

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl) benzene-1,3-diamine, was obtained.

Step 10: Preparation of 3-chloro-N-(2,4-difluoro-3-(3-(9-(tetrahydro-2H-pyran-2-yl)-9H-purin-6-yl) pyridin-2-ylamino)phenyl)-4-fluorobenzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-chloro-4-fluorobenzene-1-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.55 (s, 1H), 9.62 (dd, J=6.0, 1.6 Hz, 1H), 8.99 (s, 1H), 8.39 (s, 1H), 8.18 (dd, J=2.8, 2.0 Hz, 1H), 7.88 (dd, J=4.8, 2.0 Hz, 1H), 7.66 (m, 1H), 7.38 (m, 1H), 7.24 (m, 1H), 7.02 (m, 2H), 5.91 (d, J=2.0 Hz, 1H), 4.24 (m, 1H), 3.86 (m, 1H), 2.20-1.65 (m, 6H).

Step 11: Preparation of N-(3-(3-(9H-purin-6-yl)pyridin-2-ylamino)-2,4-difluorophenyl)-3-chloro-4-fluorobenzenesulfonamide 1M aqueous hydrochloric acid solution was added into the 3-chloro-N-(2,4-difluoro-3-(3-(9-(tetrahydro-2H-pyran-2-yl)-9H-purin-6-yl)pyridin-2-ylamino)phenyl)-4-fluorobenzenesulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

¹H NMR (400 MHz, DMSO-d₆): δ 12.15 (bs, 1H), 11.42 (s, 1H), 10.28 (s, 1H), 9.77 (dd, J=6.4, 1.6 Hz, 1H), 9.19 (s, 1H), 8.35 (s, 1H), 8.30 (dd, J=2.8, 1.6 Hz, 1H), 8.16 (dd, J=6.4, 1.6 Hz, 1H), 7.50 (m, 3H), 7.01 (m, 2H).

Example 29

Preparation of N-(3-(3-(9H-purin-6-yl)pyridin-2-ylamino)-2,4-difluorophenyl)-3-chloro-2-fluorobenzenesulfonamide

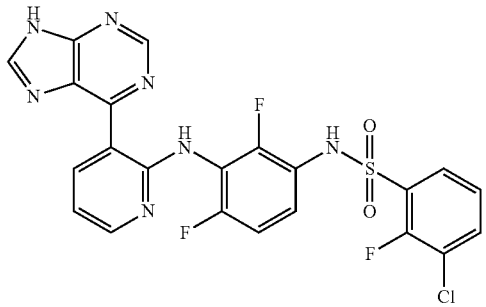 [SMILES: O=S(=O)(Nc1ccc(F)c(Nc2ncccc2-c2ncnc3[nH]cnc23)c1F)c1cccc(Cl)c1F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of 3-chloro-N-(2,4-difluoro-3-(3-(9-(tetrahydro-2H-pyran-2-yl)-9H-purin-6-yl)pyridin-2-ylamino)phenyl)-2-fluorobenzenesulfonamide The 2,6-difluoro-N¹-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-chloro-2-fluorobenzene-1-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

¹H NMR (400 MHz, CDCl₃): δ 11.55 (s, 1H), 9.63 (m, 1H), 8.99 (d, J=6.0 Hz, 1H), 8.39 (d, J=6.0 Hz, 1H), 8.20 (s, 1H), 7.72 (m, 1H), 7.61 (m, 1H), 7.30 (m, 1H), 7.18 (m, 1H), 6.94 (m, 2H), 5.91 (m, 1H), 4.23 (d, J=11.2 Hz, 1H), 3.85 (m, 1H), 2.19-1.72 (m, 6H).

Step 11: Preparation of N-(3-(3-(9H-purin-6-yl)pyridin-2-ylamino)-2,4-difluorophenyl)-3-chloro-4-fluorobenzenesulfonamide 1M aqueous hydrochloric acid solution was added into the 3-chloro-N-(2,4-difluoro-3-(3-(9-(tetrahydro-2H-pyran-2-yl)-9H-purin-6-yl)pyridin-2-ylamino)phenyl)-2-fluorobenzenesulfonamide (20 mg, 0.032 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

¹H NMR (400 MHz, DMSO-d₆): δ 11.47 (brs, 1H), 9.63 (brs, 1H), 9.00 (s, 1H), 8.73 (s, 1H), 8.15 (m, 1H), 7.72 (m, 1H), 7.65 (m, 1H), 7.35 (m, 1H), 7.08 (m, 1H), 6.92 (m, 2H).

Example 30

Preparation of N-(3-(3-(9H-purin-6-yl)pyridin-2-ylamino)-2,4-difluorophenyl)pyridin-3-sulfonamide

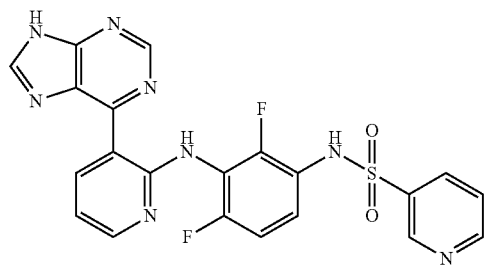 [SMILES: O=S(=O)(Nc1ccc(F)c(Nc2ncccc2-c2ncnc3[nH]cnc23)c1F)c1cccnc1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N¹-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)pyridin-3-sulfonamide The 2,6-difluoro-N¹-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. pyridin-3-sulfonyl chloride (12 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

¹H NMR (400 MHz, CDCl₃): δ 9.43 (s, 1H), 8.89 (m, 2H), 8.63 (s, 1H), 8.34 (m, 1H), 8.04 (s, 2H), 7.36 (m, 1H), 6.91 (m, 2H), 5.79 (m, 1H), 4.13 (m, 1H), 3.50 (m, 1H), 2.10-1.54 (m, 6H).

Step 11: Preparation of N-(3-(3-(9H-purin-6-yl)pyridin-2-ylamino)-2,4-difluorophenyl)pyridin-3-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)pyridin-3-sulfonamide (19 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 11.41 (s, 1H), 9.44 (s, 1H), 9.09 (s, 1H), 8.91 (s, 1H), 8.57 (s, 1H), 8.42 (m, 2H), 8.03 (m, 1H), 7.65 (m, 2H), 7.36 (m, 2H), 6.91 (m, 1H).

Example 31

Preparation of N-(3-(3-(9H-purin-6-yl)pyridin-2-ylamino)-2,4-difluorophenyl)-2-methylbenzenesulfonamide

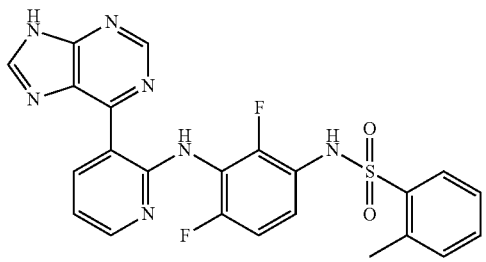 [SMILES: Cc1ccccc1S(=O)(=O)Nc1ccc(F)c(Nc2ncccc2-c2ncnc3[nH]cnc23)c1F]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-2-methylbenzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2-methylbenzene-1-sulfonyl chloride (13 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.51 (s, 1H), 9.63 (dd, J=6.0, 2.0 Hz, 1H), 8.99 (s, 1H), 8.39 (s, 1H), 8.21 (dd, J=3.2, 1.6 Hz, 1H), 7.94 (d, J=8.0 Hz, 1H), 7.46 (m, 1H), 7.31 (m, 4H), 7.03 (s, 1H), 6.95 (m, 3H), 5.89 (dd, J=8.4, 2.0 Hz, 1H), 4.22 (m, 1H), 3.85 (m, 1H), 2.69 (s, 3H), 2.19-1.70 (m, 6H).

Step 11: Preparation of N-(3-(3-(9H-purin-6-yl)pyridin-2-ylamino)-2,4-difluorophenyl)-2-methylbenzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-2-methylbenzenesulfonamide (19 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 11.42 (s, 1H), 10.31 (s, 1H), 9.75 (m, 1H), 8.97 (s, 1H), 8.59 (s, 1H), 8.17 (m, 1H), 7.75 (m, 2H), 7.43 (m, 3H), 7.03 (m, 1H), 6.91 (m, 1H), 5.91 (m, 1H), 2.65 (s, 3H).

Example 32

Preparation of N-(3-(3-(9H-purin-6-yl)pyridin-2-ylamino)-2,4-difluorophenyl)-2-chloro benzenesulfonamide

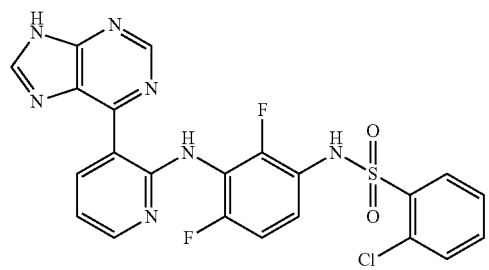 [SMILES: O=S(=O)(Nc1ccc(F)c(Nc2ncccc2-c2ncnc3[nH]cnc23)c1F)c1ccccc1Cl]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 2-chloro-N-(2,4-difluoro-3-(3-(9-(tetrahydro-2H-pyran-2-yl)-9H-purin-6-yl)pyridin-2-ylamino)phenyl)benzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2-chloro benzene-1-sulfonyl chloride (15 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.51 (s, 1H), 9.62 (dd, J=6.4, 1.6 Hz, 1H), 8.98 (s, 1H), 8.39 (s, 1H), 8.19 (dd, J=3.2, 1.6 Hz, 1H), 8.04 (m, 1H), 7.52 (m, 2H), 7.38 (m, 3H), 6.94 (m, 2H), 5.89 (dd, J=8.0, 2.4 Hz, 1H), 4.23 (m, 1H), 3.85 (m, 1H), 2.19-1.70 (m, 6H).

Step 11: Preparation of N-(3-(3-(9H-purin-6-yl)pyridin-2-ylamino)-2,4-difluorophenyl)-2-chloro benzenesulfonamide 1M aqueous hydrochloric acid solution was added into the 2-chloro-N-(2,4-difluoro-3-(3-(9-(tetrahydro-2H-pyran-2-yl)-9H-purin-6-yl)pyridin-2-ylamino)phenyl)benzenesulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.10 (s, 1H), 11.42 (s, 1H), 10.28 (s, 1H), 9.77 (dd, J=6.4, 2.0 Hz, 1H), 9.19 (s, 1H), 8.35 (s, 1H), 8.30 (dd, J=2.8, 1.6 Hz, 1H), 8.16 (dd, J=6.4, 1.6 Hz, 1H), 7.54 (m, 3H), 7.42 (m, 1H), 7.01 (m, 1H), 6.94 (m, 1H).

Example 33

Preparation of N-(3-(3-(9H-purin-6-yl)pyridin-2-ylamino)-2,4-difluorophenyl)-3-chloro benzenesulfonamide

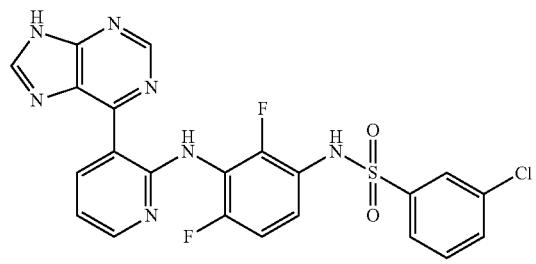 [SMILES: O=S(=O)(Nc1ccc(F)c(Nc2ncccc2-c2ncnc3[nH]cnc23)c1F)c1cccc(Cl)c1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 3-chloro-N-(2,4-difluoro-3-(3-(9-(tetrahydro-2H-pyran-2-yl)-9H-purin-6-yl)pyridin-2-ylamino)phenyl)benzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 3-chloro benzene-1-sulfonyl chloride (15 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.54 (s, 1H), 9.64 (dd, J=6.0, 2.0 Hz, 1H), 8.99 (s, 1H), 8.39 (s, 1H), 8.20 (dd, J=3.2, 1.6 Hz, 1H), 7.80 (t, J=2.0 Hz, 1H), 7.65 (m, 1H), 7.55 (m, 1H), 7.53 (m, 3H), 7.40 (m, 2H), 7.01 (m, 3H), 5.90 (dd, J=8.4, 2.0 Hz, 1H), 4.23 (m, 1H), 3.85 (m, 1H), 2.23-1.77 (m, 6H).

Step 11: Preparation of N-(3-(3-(9H-purin-6-yl)pyridin-2-ylamino)-2,4-difluorophenyl)-3-chlorobenzenesulfonamide 1M aqueous hydrochloric acid solution was added into the 3-chloro-N-(2,4-difluoro-3-(3-(9-(tetrahydro-2H-pyran-2-yl)-9H-purin-6-yl)pyridin-2-ylamino)phenyl)benzenesulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.04 (s, 1H), 9.78 (dd, J=6.0, 1.6 Hz, 1H), 9.16 (s, 1H), 8.37 (s, 1H), 8.33 (dd, J=2.8, 2.0 Hz, 1H), 7.89 (t, J=2.0 Hz, 1H), 7.76 (m, 1H), 7.52 (m, 2H), 7.40 (t, J=8.0 Hz, 1H), 7.04 (m, 2H).

Example 34

Preparation of N-(3-(3-(9H-purin-6-yl)pyridin-2-ylamino)-2,4-difluorophenyl)-2,3-chlorobenzenesulfonamide

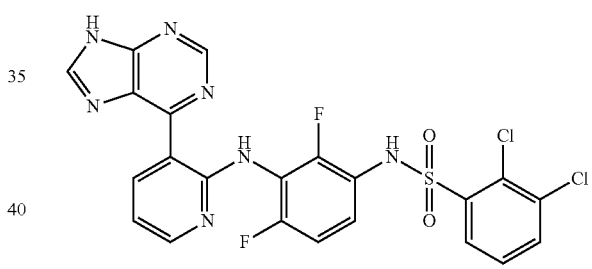

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 2,3-chloro-N-(2,4-difluoro-3-(3-(9-(tetrahydro-2H-pyran-2-yl)-9H-purin-6-yl)pyridin-2-ylamino)phenyl)benzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2,3-chlorobenzene-1-sulfonyl chloride (17 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.55 (s, 1H), 9.63 (t, J=6.0 Hz, 1H), 8.99 (d, J=6.0 Hz, 1H), 8.20 (s, 1H), 7.97 (t, J=5.6 Hz, 1H), 7.68 (t, J=6.0 Hz, 1H), 7.48 (m, 1H), 7.30 (m, 2H), 6.93 (m, 2H), 5.89 (m, 1H), 4.22 (m, 1H), 3.84 (m, 1H), 2.19-1.72 (m, 6H).

Step 11: Preparation of N-(3-(3-(9H-purin-6-yl)pyridin-2-ylamino)-2,4-difluorophenyl)-2,3-chlorobenzenesulfonamide 1M aqueous hydrochloric acid solution was added into the 2,3-chloro-N-(2,4-difluoro-3-(3-(9-(tetrahydro-2H-pyran-2-yl)-9H-purin-6-yl)pyridin-2-ylamino)phenyl)benzenesulfonamide (21 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.17 (s, 1H), 11.53 (s, 1H), 10.74 (s, 1H), 9.76 (d, J=7.6 Hz, 1H), 9.21 (s, 1H), 8.35 (s, 1H), 8.32 (d, J=2.8 Hz, 1H), 8.10 (d, J=8.0 Hz, 1H), 7.71 (d, J=8.0 Hz, 1H), 7.51 (d, J=4.8 Hz, 1H), 7.37 (t, J=8.0 Hz, 1H), 7.00 (m, 2H).

Example 35

Preparation of N-(3-(3-(9H-purin-6-yl)pyridin-2-ylamino)-2,4-difluorophenyl)benzenesulfonamide

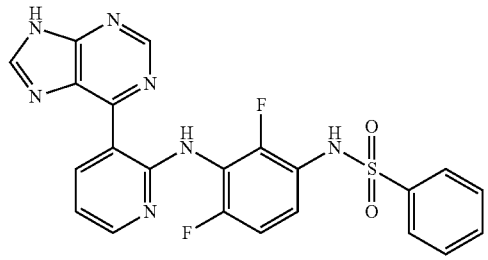 [SMILES: O=S(=O)(Nc1ccc(F)c(Nc2ncccc2-c2ncnc3[nH]cnc23)c1F)c1ccccc1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)benzenesulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. benzenesulfonyl chloride (12 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.49 (s, 1H), 9.62 (d, J=7.6 Hz, 1H), 8.98 (s, 1H), 8.39 (s, 1H), 8.19 (m, 1H), 7.80 (d, J=7.6 Hz, 1H), 7.58 (m, 1H), 7.48 (m, 2H), 7.37 (m, 1H), 7.28 (m, 1H), 6.97 (m, 2H), 6.87 (s, 1H), 5.89 (d, J=10.4 Hz, 1H), 4.23 (m, 1H), 3.85 (m, 1H), 2.23-1.73 (m, 6H).

Step 11: Preparation of N-(3-(3-(9H-purin-6-yl)pyridin-2-ylamino)-2,4-difluorophenyl)benzenesulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)benzenesulfonamide (19 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 13.19 (s, 1H), 11.39 (s, 1H), 9.51 (d, J=8.0 Hz, 1H), 9.10 (s, 1H), 8.78 (s, 1H), 8.11 (s, 1H), 7.98 (dd, J=2.8, 1.6 Hz, 1H), 7.67 (d, J=8.0 Hz, 2H), 7.41 (m, 1H), 7.32 (m, 2H), 7.11 (m, 1H), 6.76 (m, 2H).

Example 36

Preparation of N-(3-(3-(9H-purin-6-yl)pyridin-2-ylamino)-2,4-difluorophenyl)-2,3-dihydrobenzofuran-7-sulfonamide

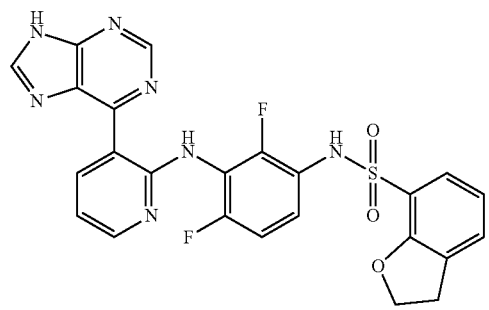 [SMILES: O=S(=O)(Nc1ccc(F)c(Nc2ncccc2-c2ncnc3[nH]cnc23)c1F)c1cccc2c1OCC2]

Step 1 to step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-2,3-dihydrobenzofuran-7-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2,3-dihydrobenzofuran-7-sulfonyl chloride (15 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.47 (s, 1H), 9.62 (dd, J=6.0, 2.0 Hz, 1H), 8.99 (s, 1H), 8.39 (s, 1H), 8.17 (dd, J=2.8, 1.6 Hz, 1H), 7.55 (dd, J=7.2, 0.8 Hz, 1H), 7.41 (m, 2H), 7.15 (d, J=2.4 Hz, 1H), 6.39 (m, 2H), 5.90 (dd, J=8.0, 2.4 Hz, 1H), 4.76 (t, J=8.8 Hz, 2H), 4.23 (m, 1H), 3.85 (m, 1H), 3.24 (t, J=8.8 Hz, 2H), 2.23-1.71 (m, 6H).

Step 11: Preparation of N-(3-(3-(9H-purin-6-yl)pyridin-2-ylamino)-2,4-difluorophenyl)-2,3-dihydrobenzofuran-7-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-2,3-dihydrobenzofuran-7-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 11.47 (brs, 1H), 9.63 (brs, 1H), 9.00 (s, 1H), 8.73 (s, 1H), 8.15 (dd, J=2.8, 2.0 Hz, 1H), 7.48 (dd, J=6.0, 1.2 Hz, 1H), 7.37 (d, J=6.8 Hz, 1H), 7.08 (m, 2H), 7.02 (m, 1H), 6.91 (t, J=7.6 Hz, 1H), 4.63 (t, J=8.8 Hz, 2H), 3.22 (t, J=8.8 Hz, 2H).

Example 37

Preparation of N-(3-(3-(9H-purin-6-yl)pyridin-2-ylamino)-2,4-difluorophenyl)benzofuran-7-sulfonamide Step 10: Preparation of N-(2,4-difluoro-3-(3-(9-(tetrahydro-2H-pyran-2-yl)-9H-purin-6-yl)pyridin-2-ylamino)phenyl)benzofuran-7-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. benzofuran-7-sulfonyl chloride (15 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.41 (s, 1H), 9.59 (dd, J=6.0, 2.0 Hz, 1H), 8.94 (s, 1H), 8.37 (s, 1H), 8.14 (dd, J=2.8, 2.0 Hz, 1H), 7.83 (dd, J=6.8, 1.2 Hz, 1H), 7.78 (m, 2H), 7.37 (m, 1H), 7.31 (m, 2H), 5.88 (dd, J=8.0, 2.4 Hz, 1H), 4.23 (m, 1H), 3.84 (m, 1H), 2.19-1.72 (m, 6H).

Step 11: Preparation of N-(3-(3-(9H-purin-6-yl)pyridin-2-ylamino)-2,4-difluorophenyl)benzofuran-7-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)benzofuran-7-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 13.87 (s, 1H), 11.55 (s, 1H), 10.51 (s, 1H), 9.74 (d, J=14.8 Hz, 1H), 9.02 (s, 1H), 8.71 (s, 1H), 8.20 (d, J=2.8 Hz, 1H), 7.98 (d, J=6.8 Hz, 1H), 7.63 (d, J=7.6 Hz, 1H), 7.37 (m, 1H), 7.11 (m, 3H), 7.01 (m, 1H).

Example 38

Preparation of N-(3-(3-(9H-purin-6-yl)pyridin-2-ylamino)-2,4-difluorophenyl)chromane-8-sulfonamide

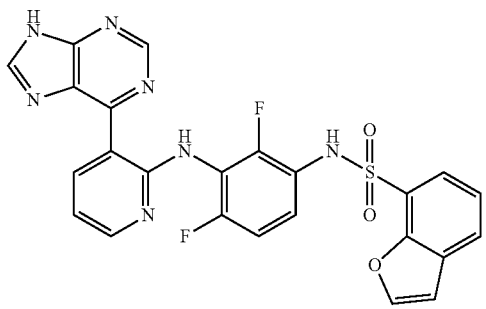 [SMILES: O=S(=O)(Nc1ccc(F)c(Nc2ncccc2-c2ncnc3[nH]cnc23)c1F)c1cccc2ccoc12]

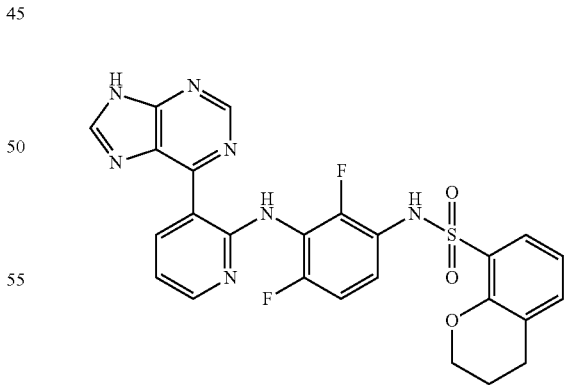

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-

(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)chromane-8-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. chromane-8-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.47 (s, 1H), 9.62 (dd, J=6.0, 1.6 Hz, 1H), 8.99 (s, 1H), 8.39 (s, 1H), 8.16 (dd, J=2.8, 1.6 Hz, 1H), 7.67 (m, 1H), 7.46 (m, 1H), 7.33 (d, J=2.8 Hz, 1H), 7.24 (dd, J=6.0, 1.6 Hz, 1H), 6.90 (m, 3H), 5.89 (m, 1H), 4.37 (t, J=5.2 Hz, 2H), 4.24 (m, 1H), 3.85 (m, 1H), 2.80 (t, J=6.4 Hz, 2H), 2.23-1.73 (m, 6H).

Step 11: Preparation of N-(3-(3-(9H-purin-6-yl)pyridin-2-ylamino)-2,4-difluorophenyl)chromane-8-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)chromane-8-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 12.08 (s, 1H), 9.91 (brs, 1H), 9.78 (dd, J=6.4, 1.6 Hz, 1H), 9.18 (s, 1H), 8.34 (s, 1H), 8.30 (dd, J=2.8, 2.0 Hz, 1H), 7.74 (dd, J=6.4, 1.6 Hz, 1H), 7.51 (m, 1H), 7.23 (d, J=2.8 Hz, 1H), 7.00 (m, 1H), 6.96 (m, 2H), 3.97 (t, J=4.8 Hz, 2H), 2.75 (t, J=6.4 Hz, 2H), 1.09 (m, 2H).

Example 39

Preparation of N-(3-(3-(9H-purin-6-yl)pyridin-2-ylamino)-2,4-difluorophenyl)-2-methylbenzo[d]thiazole-6-sulfonamide

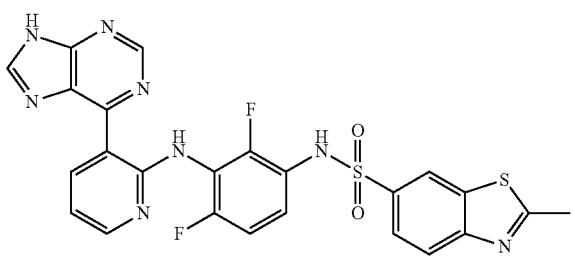 [SMILES: Cc1nc2ccc(S(=O)(=O)Nc3ccc(F)c(Nc4ncccc4-c4ncnc5[nH]cnc45)c3F)cc2s1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-2-methylbenzo[d]thiazole-6-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 2-methylbenzo[d]thiazole-6-sulfonyl chloride (17 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.46 (s, 1H), 9.59 (dd, J=6.0, 1.6 Hz, 1H), 8.59 (s, 1H), 8.37 (s, 1H), 8.33 (d, J=1.6 Hz, 1H), 8.10 (dd, J=3.2, 1.6 Hz, 1H), 8.00 (d, J=8.4 Hz, 1H), 7.83 (dd, J=6.8, 2.0 Hz, 1H), 7.43 (m, 1H), 7.00 (m, 1H), 6.92 (m, 1H), 6.74 (d, J=1.6 Hz, 1H), 5.89 (dd, J=8.0, 2.4 Hz, 1H), 4.24 (m, 1H), 3.84 (m, 1H), 2.88 (s, 3H), 2.22-1.80 (m, 6H).

Step 11: Preparation of N-(3-(3-(9H-purin-6-yl)pyridin-2-ylamino)-2,4-difluorophenyl)-2-methylbenzo[d]thiazole-6-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-2-methylbenzo[d]thiazole-6-sulfonamide (21 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, DMSO-d$_6$): δ 11.42 (brs, 1H), 9.62 (brs, 1H), 8.95 (s, 1H), 8.71 (s, 1H), 8.50 (d, J=1.6 Hz, 1H), 8.05 (m, 2H), 7.81 (dd, J=6.8, 1.6 Hz, 1H), 7.10 (m, 2H), 6.99 (m, 1H), 2.84 (s, 3H).

Example 40

Preparation of N-(3-(3-(9H-purin-6-yl)pyridin-2-ylamino)-2,4-difluorophenyl)-1-methyl-1H-indole-5-sulfonamide

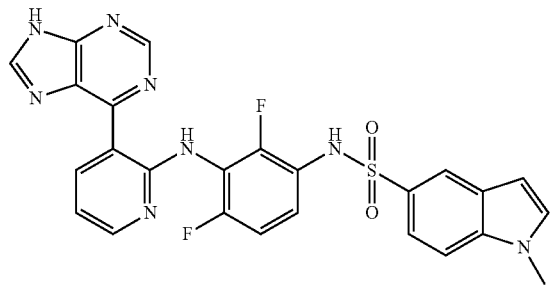 [SMILES: Cn1ccc2cc(S(=O)(=O)Nc3ccc(F)c(Nc4ncccc4-c4ncnc5[nH]cnc45)c3F)ccc21]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-$N^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-1-methyl-1H-indole-5-sulfonamide The 2,6-difluoro-$N^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 1-methyl-1H-indole-5-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.29 (s, 1H), 9.99 (s, 1H), 9.57 (dd, J=6.0, 1.6 Hz, 1H), 9.02 (s, 1H), 8.96 (s, 1H), 8.07 (dd, J=2.8, 2.0 Hz, 1H), 8.00 (d, J=1.6 Hz, 1H), 7.61 (d, J=8.8 Hz, 1H), 7.55 (dd, J=6.8, 1.6 Hz, 1H), 7.51 (d, J=3.2 Hz, 1H), 7.08 (m, 2H), 6.99 (m, 1H), 6.62 (d, J=2.4 Hz, 1H), 5.86 (dd, J=8.8, 2.0 Hz, 1H), 4.05 (m, 1H), 3.83 (s, 3H), 3.75 (m, 1H), 2.41-1.65 (m, 6H).

Step 11: Preparation of N-(3-(3-(9H-purin-6-yl)pyridin-2-ylamino)-2,4-difluorophenyl)-1-methyl-1H-indole-5-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-methyl-1H-indole-5-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.04 (s, 1H), 11.59 (brs, 1H), 9.86 (s, 1H), 9.76 (dd, J=6.0, 2.0 Hz, 1H), 9.16 (s, 1H), 8.35 (s, 1H), 8.26 (m, 2H), 7.72 (m, 1H), 7.53 (m, 1H), 7.33 (m, 1H), 7.14 (d, J=3.2 Hz, 1H), 6.97 (m, 2H), 6.57 (dd, J=2.4, 0.8 Hz, 1H), 3.77 (s, 3H).

Example 41

Preparation of N-(3-(3-(9H-purin-6-yl)pyridin-2-ylamino)-2,4-difluorophenyl)-1-methyl-1H-indole-4-sulfonamide

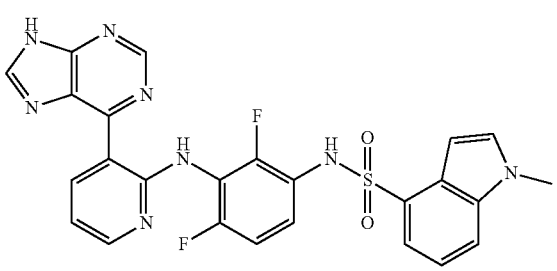 [SMILES: Cn1ccc2c(S(=O)(=O)Nc3ccc(F)c(Nc4ncccc4-c4ncnc5[nH]cnc45)c3F)cccc21]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-$N^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-1-methyl-1H-indole-4-sulfonamide The 2,6-difluoro-$N^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 1-methyl-1H-indole-5-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.27 (s, 1H), 10.18 (s, 1H), 9.57 (dd, J=5.6, 2.0 Hz, 1H), 9.05 (s, 1H), 8.96 (s, 1H), 8.15 (dd, J=2.8, 2.0 Hz, 1H), 7.76 (d, J=7.2 Hz, 1H), 7.51 (m, 1H), 7.25 (m, 1H), 7.01 (m, 3H), 6.82 (d, J=2.8 Hz, 1H), 5.87 (dd, J=8.8, 2.0 Hz, 1H), 4.08 (m, 1H), 3.83 (s, 3H), 3.76 (m, 1H), 2.35-1.63 (m, 6H).

Step 11: Preparation of N-(3-(3-(9H-purin-6-yl)pyridin-2-ylamino)-2,4-difluorophenyl)-1-methyl-1H-indole-4-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-methyl-1H-indole-4-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.12 (s, 1H), 11.89 (brs, 1H), 10.50 (s, 1H), 9.77 (d, J=6.8 Hz, 1H), 9.22 (s, 1H), 8.33 (s, 1H), 8.28 (dd, J=2.8, 2.0 Hz, 1H), 7.80 (dd, J=6.8, 0.8 Hz, 1H), 7.53 (m, 1H), 7.25 (m, 1H), 7.11 (d, J=3.2 Hz, 1H), 6.97 (m, 2H), 6.88 (m, 1H), 3.73 (s, 3H).

Example 42

Preparation of N-(3-(3-(9H-purin-6-yl)pyridin-2-ylamino)-2,4-difluorophenyl)-1-methyl-1H-indole-7-sulfonamide

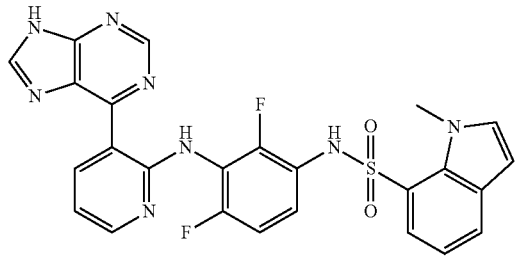 [SMILES: Cn1ccc2cccc(S(=O)(=O)Nc3ccc(F)c(Nc4ncccc4-c4ncnc5[nH]cnc45)c3F)c21]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-1-methyl-1H-indole-7-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 1-methyl-1H-indole-7-sulfonyl chloride (16 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.59 (s, 1H), 9.65 (dd, J=6.0, 2.0 Hz, 1H), 9.01 (s, 1H), 8.39 (s, 1H), 8.26 (dd, J=2.8, 2.0 Hz, 1H), 7.84 (m, 2H), 7.16 (m, 3H), 7.06 (brs, 1H), 6.97 (m, 1H), 6.87 (m, 1H), 6.63 (d, J=3.2 Hz, 1H), 5.90 (dd, J=8.0, 2.4 Hz, 1H), 4.29 (s, 3H), 4.25 (m, 1H), 3.85 (m, 1H), 2.23-1.70 (m, 6H).

Step 11: Preparation of N-(3-(3-(9H-purin-6-yl)pyridin-2-ylamino)-2,4-difluorophenyl)-1-methyl-1H-indole-7-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-methyl-1H-indole-7-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 12.13 (s, 1H), 11.64 (brs, 1H), 10.34 (brs, 1H), 9.77 (dd, J=6.4, 1.2 Hz, 1H), 9.25 (s, 1H), 8.32 (s, 1H), 7.92 (dd, J=7.2, 0.8 Hz, 1H), 7.85 (dd, J=7.2, 0.8 Hz, 1H), 7.39 (m, 1H), 7.12 (m, 2H), 7.00 (m, 1H), 6.93 (m, 1H), 6.62 (d, J=3.2 Hz, 1H), 4.35 (s, 3H).

Example 43

Preparation of N-(3-(3-(9H-purin-6-yl)pyridin-2-ylamino)-2,4-difluorophenyl)-1-methyl-1H-pyrazole-4-sulfonamide

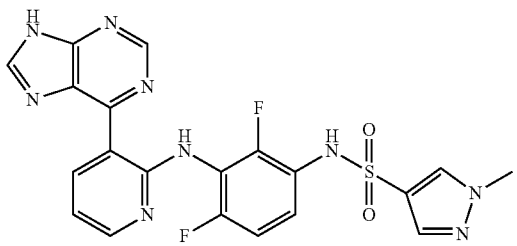 [SMILES: Cn1cc(S(=O)(=O)Nc2ccc(F)c(Nc3ncccc3-c3ncnc4[nH]cnc34)c2F)cn1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of N-(2,4-difluoro-3-(3-(9-(tetrahydro-2H-pyran-2-yl)-9H-purin-6-yl)pyridin-2-ylamino)phenyl)-1-methyl-1H-pyrazole-4-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 1-methyl-1H-pyrazole-4-sulfonyl chloride (13 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.54 (s, 1H), 9.63 (dd, J=6.0, 2.0 Hz, 1H), 9.00 (s, 1H), 8.63 (m, 1H), 8.39 (s, 1H), 8.24 (dd, J=2.8, 2.0 Hz, 1H), 7.69 (m, 2H), 7.40 (m, 1H), 7.30 (m, 1H), 7.20 (brs, 1H), 6.98 (m, 2H), 5.89 (dd, J=8.0, 2.4 Hz, 1H), 4.22 (m, 1H), 3.87 (m, 3H), 3.83 (m, 1H), 2.22-1.72 (m, 6H).

Step 11: Preparation of N-(3-(3-(9H-purin-6-yl)pyridin-2-ylamino)-2,4-difluorophenyl)-1-methyl-1H-pyrazole-4-sulfonamide 1M aqueous hydrochloric acid solution was added into the N-(2,4-difluoro-3-(3-(9-(tetrahydro-2H-pyran-2-yl)-9H-purin-6-yl)pyridin-2-ylamino)phenyl)-1-methyl-1H-pyrazole-4-sulfonamide (19 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 9.60 (s, 1H), 8.97 (s, 1H), 8.28 (s, 1H), 8.20 (dd, J=3.2, 1.6 Hz, 1H), 7.71 (d, J=10.4 Hz, 2H), 7.41 (m, 1H), 6.98 (m, 2H), 3.86 (s, 3H).

Example 44

Preparation of N-(3-(3-(9H-purin-6-yl)pyridin-2-ylamino)-2,4-difluorophenyl)-5-chlorothiophene-4-sulfonamide

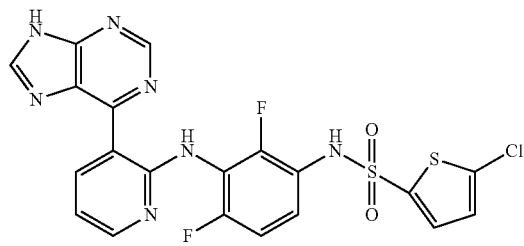 [SMILES: O=S(=O)(Nc1ccc(F)c(Nc2ncccc2-c2ncnc3[nH]cnc23)c1F)c1ccc(Cl)s1]

Step 1 to Step 9: Preparation of 2,6-difluoro-N1-(3-(9-(tetrahydro-2H-pyran-2-yl)-9H-purin-6-yl)pyridin-2-yl)benzene-1,3-diamine The same method as stated at Steps 1 to 9 of Example 2 was performed and the target compound, 2,6-difluoro-N$^1$-(3-(9-(tetrahydro-2H-pyran-2-yl)-9H-purin-6-yl)pyridin-2-yl)benzene-1,3-diamine, was obtained.

Step 10: Preparation of 5-chloro-N-(2,4-difluoro-3-(3-(9-(tetrahydro-2H-pyran-2-yl)-9H-purin-6-yl)pyridin-2-ylamino)phenyl)thiophene-2-sulfonamide The 2,6-difluoro-N$^1$-(3-(9-(tetrahydro-2H-pyran-2-yl)-9H-purin-6-yl)pyridin-2-yl)benzene-1,3-diamine (20 mg, 0.047 mmol) prepared at Step 9 was added and dissolved into dichloromethane solvent. 5-chlorothiophene-2-sulfonyl chloride (15 mg, 0.07 mmol) and pyridine (8 uL, 0.094 mmol) were added into the reaction solution and stirred at 50° C. for 2 hours. After the reaction, the reactant was washed with 1N aqueous hydrochloric acid solution and salt water. After extraction with dichloromethane, the organic layer was dried with sulfuric anhydride magnesium and vacuum concentrated, and then refined by means of column chromatography, so that the target compound was obtained.

$^1$H NMR (400 MHz, CDCl$_3$): δ 11.58 (s, 1H), 9.64 (dd, J=6.0, 2.0 Hz, 1H), 8.99 (s, 1H), 8.39 (m, 1H), 8.25 (dd, J=2.8, 2.0 Hz, 1H), 7.70 (s, 1H), 7.36 (m, 1H), 7.27 (d, J=4.0 Hz, 1H), 6.99 (m, 2H), 6.86 (d, J=4.4 Hz, 1H), 5.89 (dd, J=8.4, 2.4 Hz, 1H), 4.24 (m, 1H), 3.84 (s, 1H), 2.22-1.72 (m, 6H).

Step 11: Preparation of N-(3-(3-(9H-purin-6-yl)pyridin-2-ylamino)-2,4-difluorophenyl)-5-chlorothiophene-2-sulfonamide 1M aqueous hydrochloric acid solution was added into the 5-chloro-N-(2,4-difluoro-3-(3-(9-(tetrahydro-2H-pyran-2-yl)-9H-purin-6-yl)pyridin-2-ylamino)phenyl)thiophene-2-sulfonamide (20 mg, 0.033 mmol) prepared at Step 10 and stirred for 2 hours. After the reaction, the reactant was washed with an aqueous solution of sodium hydrogen carbonate and salt water. After extraction with ethylacetate, the organic layer was dried with sulfuric anhydride magnesium and vacuum concentrated, and then refined by means of column chromatography, so that the target compound was obtained.

$^1$H NMR (400 MHz, CDCl$_3$): δ 13.88 (s, 1H), 11.52 (s, 1H), 10.56 (s, 1H), 9.68 (d, J=7.8 Hz, 1H), 9.02 (s, 1H), 8.73 (s, 1H), 8.19 (dd, J=2.8, 1.6 Hz, 1H), 7.37 (d, J=3.6 Hz, 1H), 7.24 (d, J=3.6 Hz, 1H), 7.16 (d, J=6.0 Hz, 1H), 7.03 (m, 1H).

Experimental Example 1

Experiment of B-Raf Kinase Activity Effects

To check the B-Raf kinase inhibitory activity of the compounds of the present invention, the following experiments were conducted.

(1) Serial Signaling

20 μl of diluting solvent (20 mM MOPS, pH 7.2, 25 mM β-glycerol phosphate, 5 mM EGTA, 1 mM sodium orthovanadate, 1 mM dithiothreitol) and 10 μl of Mg/ATP mixed solution (500 μM ATP, 75 mM magnesium chloride) were added into a centrifuge tube, the derivative compound of Formula 1 was added or the compounds of the Examples were not added as a control group, and then 1 ng of activated B-Raf, 0.4 ng of inactivated MEK1, and 1 μg of inactivated MAPK2 were added. The solutions in the tube were collected on the bottom via centrifugation and were reacted at 30° C. for 30 minutes. After taking 4 μl of the mixed solution, the test proceeded to the next step.

(2) Phosphorylation of Matrix Protein MBP by MAPK2

10 μl of diluting solvent, 20 μg of MBP used as a matrix, and 10 μl of diluted [γ-32P]ATP (1 μCi/μL) were added into the 4 μl of the mixed solution obtained from (1). The solutions in the tube were collected on the bottom via centrifugation and were reacted at 30° C. for 30 minutes. And 25 μl of the reacted solution was put carefully on the center of a filter paper (2 cm×2 cm P81) for 30 seconds. Afterwards, the filter paper was cleaned with 0.75% phosphoric acid for 10 minutes three times and with acetone for 5 minutes one time. The filter paper was then moved to a scintillation vial and 5 ml of scintillation cocktail was added thereto. The inhibition rate (IC$_{50}$) over B-Raf activity was measured by reading radioactivity through a scintillation counter while comparing to the control group. The results of the measurement are provided in Table 2 below.

TABLE 2

| Compound in Example | B-Raf Enzyme Activity; IC$_{50}$ (μM) |
| --- | --- |
| Example 1 | 0.017 |
| Example 2 | 0.0088 |
| Example 3 | 0.030 |

TABLE 2-continued

| Compound in Example | B-Raf Enzyme Activity; IC$_{50}$ (μM) |
|---|---|
| Example 4 | 0.012 |
| Example 5 | 0.023 |
| Example 6 | 0.72 |
| Example 7 | 0.832 |
| Example 8 | 0.0337 |
| Example 9 | 1.5 |
| Example 10 | 1.2 |
| Example 11 | 0.206 |
| Example 12 | 0.610 |
| Example 13 | 0.42 |
| Example 14 | 0.002 |
| Example 15 | 0.001 |
| Example 16 | 1.5 |
| Example 17 | 0.007 |
| Example 18 | 0.001 |
| Example 19 | 0.05 |
| Example 20 | 0.16 |
| Example 21 | 1.3 |
| Example 22 | 1.8 |
| Example 23 | 0.015 |
| Example 24 | 0.22 |
| Example 25 | 0.015 |
| Example 26 | 0.03 |
| Example 27 | 0.08 |
| Example 28 | 0.3 |
| Example 29 | 0.08 |
| Example 30 | 0.004 |
| Example 31 | 0.05 |
| Example 32 | 0.03 |
| Example 33 | 0.08 |
| Example 34 | 0.04 |
| Example 35 | 0.02 |
| Example 36 | 1.02 |
| Example 37 | 0.09 |
| Example 38 | 0.9 |
| Example 39 | 0.4 |
| Example 40 | >10 |
| Example 41 | 0.55 |
| Example 42 | 0.8 |
| Example 43 | 0.12 |
| Example 44 | 0.02 |

As shown in Table 2 above, the compounds according to the present invention were confirmed to have a desirable B-Raf activity inhibiting effect, presenting the inhibition rate over B-Raf activity at 0.001~1.8 μM. It was confirmed that most of the compounds had a desirable B-Raf inhibitory activity, with the inhibition rate at less than 1 μM.

Experimental Example 2

Experiment of B-Raf Cell Activity Inhibition

To check the B-Raf cell activity inhibitory capability of the compounds of the present invention, the following experiments were conducted in A375P cell line (ATCC). The A375P cell line (ATCC) was derived from a patient with human melanoma, and had V600E mutant of B-Raf gene. A375 cell was maintained in DMEM supplemented with 10% fetal bovine serum, glutamine (2 mM), penicillin (100 U/mL), and streptomycin (100 μg/mL). The cell was maintained at 37° C., and in 5% CO$_2$ and 100% humidity. To conduct the growth inhibition test, the cell was plated by using a white 384-well microplate, with 1000 cells/20 μl plated per 1 well. After 24 hours, 5 μl of 5× stock solution of drug was added. All the drugs were initially prepared with 200× stock solution in DMSO, and the final concentration of DMSO was 0.5%. The cell was incubated at 37° C. for 72 hours. For MTT assay, 'CellTiter 96 (R) Non-Radioactive Cell Proliferation Assay (G4100)' kit by Promega Corp. was used. 15 μl of dye solution of the Promega kit was put into each well and was cultured in the incubator for 4 hours. And 100 μl of each Solubilization/Stop Solution substance of the kit was added and fixed in the incubator for 24 hours again. And then, absorbance was measured by using a 96-well plate reader with 570 nm of absorbance. Based on the negative control, the measured absorbance was converted into relative cell toxicity by concentration and EC$_{50}$ (half maximal effective concentration) was calculated. The results thereof are provided in Table 3 below.

TABLE 3

B-Raf Cell Inhibitory Activity

| Compound in Example | Cell Activity (A375P), IC$_{50}$ (μM) |
|---|---|
| Example 1 | 0.12 |
| Example 2 | 0.23 |
| Example 3 | 5.2 |
| Example 4 | 0.03 |
| Example 5 | 0.31 |
| Example 6 | 2.8 |
| Example 7 | 4.3 |
| Example 8 | 0.7 |
| Example 9 | 11.2 |
| Example 10 | 10.2 |
| Example 11 | 0.34 |
| Example 12 | 0.6 |
| Example 13 | 0.15 |
| Example 14 | 0.006 |
| Example 15 | 11.0 |
| Example 16 | 9.6 |
| Example 17 | 0.04 |
| Example 18 | 0.002 |
| Example 19 | 0.25 |
| Example 20 | 0.7 |
| Example 21 | 0.36 |
| Example 22 | 1.0 |
| Example 23 | 0.06 |
| Example 24 | 0.8 |
| Example 25 | 0.1 |
| Example 26 | 0.33 |
| Example 27 | 0.76 |
| Example 28 | 1.93 |
| Example 29 | 0.72 |
| Example 30 | 0.07 |
| Example 31 | 0.67 |
| Example 32 | 0.44 |
| Example 33 | 0.77 |
| Example 34 | 0.5 |
| Example 35 | 0.16 |
| Example 36 | 8.37 |
| Example 37 | 0.81 |
| Example 38 | 7.19 |
| Example 39 | 2.93 |
| Example 40 | >15 |
| Example 41 | 4.20 |
| Example 42 | 5.87 |
| Example 43 | 1.37 |
| Example 44 | 0.2 |

As shown in Table 3 above, the compounds according to the present invention were confirmed to have a desirable A375P cell activity inhibiting effect, presenting the inhibition rate over A375P cell activity at 0.006~11.2 μM. It was confirmed that most of the compounds had a desirable anticancer, inhibitory activity, with the inhibition rate at less than 1 μM.

Therefore, the compounds presented in Examples of the present invention can be used helpfully as a medicine for the diseases associated with abnormal B-Raf activity—cancers including melanoma, colorectal cancer, renal cancer, prostate cancer, thyroid cancer, ovarian cancer, in particular.

In the meantime, the purinylpyridinylamino-2,4-difluorophenyl sulfonamide derivatives can be formulated in various forms according to purpose. Several formulation methods of containing the compounds represented by Formula 1 are exemplified hereinafter. However, the present invention is not limited thereto.

Manufacturing Example 1

Preparation of Powders

| | |
|---|---|
| Compound of Formula 1 | 2 g |
| Lactose | 1 g |

Powders were prepared by mixing the components above and filled in airtight packs.

Manufacturing Example 2

Preparation of Tablets

| | |
|---|---|
| Compound of Formula 1 | 100 mg |
| Corn starch | 100 mg |
| Lactose | 100 mg |
| Magnesium stearate | 2 mg |

Tablets were prepared by mixing the components above by the conventional method for preparing tablets

Manufacturing Example 3

Preparation of Capsules

| | |
|---|---|
| Compound of Formula 1 | 100 mg |
| Corn starch | 100 mg |
| Lactose | 100 mg |
| Magnesium stearate | 2 mg |

Capsules were prepared by mixing the components above by the conventional method for preparing capsules and filled in gelatin capsules.

Manufacturing Example 4

Preparation of Injections

| | |
|---|---|
| Compound of Formula 1 | 100 mg |
| Mannitol | 180 mg |
| $Na_2HPO_4 \cdot 2H_2O$ | 26 mg |
| Distilled water | 2974 mg |

Injections were prepared using the presented contents of each component by the conventional method for preparing injections.

Manufacturing Example 5

Preparation of Health Food

| | |
|---|---|
| Compound of Formula 1 | 1000 mg |
| Vitamin complex | proper amount |
| Vitamin A acetate | 70 μg |
| Vitamin E | 1.0 mg |
| Vitamin | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 mg |
| Calcium pantothenate | 0.5 mg |
| Minerals | proper amount |
| Ferrous sulphate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

The vitamins and minerals above were mixed according to the preferable composition ratio for health food, but can be mixed according to adjusted composition ratio. According to the conventional method for preparing health food, the constituents were mixed and granulated.

Manufacturing Example 6

Preparation of Health Beverage

| | |
|---|---|
| Compound of Formula 1 | 1000 mg |
| Citric acid | 1000 mg |
| Oligosaccharide | 100 g |
| Maesil (*prunus mume*) extract | 2 g |
| Taurine | 1 g |
| Purified water | up to 900 ml |

According to the conventional method for preparing health beverages, the constituents above were mixed and stirred/heated at 85° C. for 1 hour. And then the mixture was filtered and loaded in sterilized 2 L containers, and then sealed and sterilized again and stored in a refrigerator until used as a composition for health beverages.

The constituents above were mixed at a desirable ratio for favorite beverages, but can be mixed at an adjusted and modified ratio according to regional and national preferences including consuming class of people, consuming country, use, etc.

Manufacturing Example 7

Preparation of Other Health Foods

7-1. Preparation of Beverages

| | |
|---|---|
| Honey | 522 mg |
| Thioctic acid amide | 5 mg |
| Nicotinic acid amide | 10 mg |
| Riboflavin sodium hydrochloride | 3 mg |
| Pyridoxine hydrochloride | 2 mg |
| Inositol | 30 mg |
| Orotic acid | 50 mg |
| Compound of Formula 1 | 0.48~1.28 mg |
| Water | 200 ml |

Beverages were prepared with the composition and contents presented above, by the conventional method for preparing beverages.

7-2. Preparation of Chewing Gums

| Gum base | 20% |
|---|---|
| Sugar | 76.36~76.76% |
| Compound of Formula 1 | 0.24~0.64% |
| Fruit flavor | 1% |
| Water | 2% |

Chewing gums were prepared with the composition and contents presented above, by the conventional method for preparing chewing gums.

7-3. Preparation of Candies

| Sugar | 50~60% |
|---|---|
| Starch syrup | 39.26~49.66% |
| Compound of Formula 1 | 0.24~0.64% |
| Orange flavor | 0.1% |

Candies were prepared with the composition and contents presented above, by the conventional method for preparing candies.

7-4. Preparation of Wheat Flour Foods

Health boosting foods were prepared by adding 0.5 to 5 PBW (parts by weight) of the purinylpyridinylamino-2,4-difluorophenyl sulfonamide derivative of Formula 1 to 100 PBW of flour and using the mixture to make breads, cakes, cookies, crackers, and noodles.

7-5. Preparation of Dairy Products

Various dairy products such as butter and ice cream were prepared by adding 5 to 10 PBW of the purinylpyridinylamino-2,4-difluorophenyl sulfonamide derivative of Formula 1 to 100 PBW of milk and using the milk.

7-6. Preparation of Sunsik (Natural Powdered Food)

Unpolished rice, barley, glutinous rice, and adlay were pre-gelatinized, dried, supplied with electric power, and pulverized by a crusher to the grain size of 60 mesh. Black bean, black sesame seeds, and perilla seeds were steamed, dried, supplied with electric power, and pulverized by a crusher to the grain size of 60 mesh. The prepared grains, seeds, and nuts, and the purinylpyridinylamino-2,4-difluorophenyl sulfonamide derivative of Formula 1 were mixed together at the following ratio to make sunsik (natural powdered food).

| Unpolished rice | 30% |
|---|---|
| Adlay | 15% |
| Barley | 20% |
| *Perilla* | 7% |
| Black bean | 7% |
| Black sesame | 7% |
| Compound of Formula 1 | 3% |
| Lingshi mushroom | 0.5% |
| *Rehmannia* root | 0.5% |

What is claimed is:

1. A purinylpyridinylamino-2,4-difluorophenyl sulfonamide derivative represented by Formula 1 below or a pharmaceutically acceptable salt thereof:

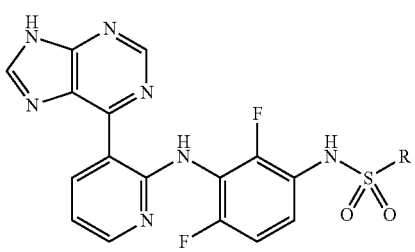

wherein R is methyl; ethyl; propyl; isopropyl; butyl; isobutyl;
$C_3$-$C_6$ cycloalkyl non-substitutable or substituted with one or more selected from the group consisting of halogen and $C_1$-$C_6$ straight or branched alkyl;
$C_5$-$C_6$ aryl substituted with one or more selected from the group consisting of halogen, $C_1$-$C_5$ straight or branched alkyl, and $C_1$-$C_6$ straight or branched alkoxy substituted with $C_1$-$C_6$ straight or branched alkoxy and halogen;
$C_5$-$C_6$ single or double ring heteroaryl non-substitutable or substituted with one or more selected from the group consisting of $C_1$-$C_6$ straight or branched alkyl substituted with halogen, $C_1$-$C_6$ straight or branched alkyl, $C_1$-$C_6$ straight or branched alkyloxycarbonyl, and $C_5$-$C_6$ heterocycloalkyl containing one or more oxygen (O) in the ring;
$C_5$-$C_6$ heterocycloalkyl non-substitutable or substituted with one or more selected from the group consisting of halogen and $C_1$-$C_6$ straight or branched alkyl; or
$C_5$-$C_6$ aryl $C_1$-$C_6$ straight or branched alkyl non-substitutable or substituted with halogen, nitro, and $C_1$-$C_6$ straight or branched alkyl,
wherein the heteroaryl and heterocycloalkyl contain one or more heteroatom selected from the group consisting of N, O, and S in the ring.

2. The purinylpyridinylamino-2,4-difluorophenyl sulfonamide derivative or the pharmaceutically acceptable salt thereof according to claim 1, wherein the R is methyl; ethyl; propyl; isopropyl; butyl; isobutyl; cyclopropyl; cyclobutyl; cyclopentyl; cyclohexyl;
$C_5$-$C_6$ aryl non-substitutable or substituted with one or more selected from the group consisting of chloro, fluoro, bromo, methyl, ethyl, propyl, isopropyl, butyl, isobutyl, methoxy, ethoxy, propoxy, butoxy, trifluoromethoxy, fluoromethoxy, difluoromethoxy, and trifluoroethoxy;
$C_5$-$C_6$ single or double ring heteroaryl non-substitutable or substituted with one or more selected from the group consisting of methyl, ethyl, propyl, isopropyl, butyl, isobutyl, methyloxycarbonyl, ethyloxycarbonyl, propyloxycarbonyl, butyloxycarbonyl, t-butyloxycarbonyl, and dioxolanyl;
$C_5$-$C_6$ heterocycloalkyl non-substitutable or substituted with one or more selected from the group consisting of chloro, fluoro, bromo, methyl, ethyl, propyl, isopropyl, butyl, and isobutyl; or
$C_5$-$C_6$ aryl $C_1$-$C_6$ straight or branched alkyl non-substitutable or substituted with one or more selected from the group consisting of chloro, fluoro, bromo, nitro, methyl, ethyl, propyl, isopropyl, butyl, and isobutyl,
wherein the heteroaryl and heterocycloalkyl contain one or more heteroatom selected from the group consisting of N, O, and S in the ring.

3. The purinylpyridinylamino-2,4-difluorophenyl sulfonamide derivative or the pharmaceutically acceptable salt thereof according to claim 1, wherein the R is methyl; ethyl; propyl; isopropyl; cyclopropyl; cyclohexyl;

phenyl non-substitutable or substituted with one or more selected from the group consisting of chloro, fluoro, methyl, methoxy, and trifluoromethoxy;

thiophene, thiazole, furan, imidazole, pyridine, dihydrobenzofuran, benzofuran, chroman, benzothiazole, indole, or pyrazole non-substitutable or substituted with one or more selected from the group consisting of methyl, methyloxycarbonyl(methylester), and dioxolanyl;

morpholine; or phenylmethyl substituted with nitro.

4. The purinylpyridinylamino-2,4-difluorophenyl sulfonamide derivative or the pharmaceutically acceptable salt thereof according to claim 1, wherein compounds represented by the Formula 1 consist of:

(1) N-(3-(3-(9H-purin-6-yl)pyridin-2-ylamino)-2,4-difluorophenyl)propane-2-sulfonamide;

(2) N-(3-(3-(9H-purin-6-yl)pyridin-2-yl amino)-2,4-difluorophenyl)-3-(trifluoromethyl) benzene sulfonamide;

(3) N-(3-(3-(9H-purin-6-yl)pyridin-2-yl amino)-2,4-difluorophenyl)-4-(trifluoromethyl)benzene sulfonamide;

(4) N-(3-(3-(9H-purin-6-yl)pyridin-2-yl amino)-2,4-difluorophenyl)thiophene-2-sulfonamide;

(5) N-(3-(3-(9H-purin-6-yl)pyridin-2-yl amino)-2,4-difluorophenyl)propane-1-sulfonamide;

(6) N-(3-(3-H-purin-6-yl)pyridin-2-yl amino)-2,4-difluorophenyl)-3,4-dichloro benzene sulfonamide;

(7) N-(3-(3-(9H-purin-6-yl)pyridin-2-yl amino)-2,4-difluorophenyl)benzofuran-2-sulfonamide;

(8) N-(3-(3-(9H-purin-6-yl)pyridin-2-yl amino)-2,4-difluorophenyl)-4-chloro-2-fluoro benzene sulfonamide;

(9) N-(3-(3-(9H-purin-6-yl)pyridin-2-yl amino)-2,4-difluorophenyl)-1-(2-nitrophenyl) methane sulfonamide;

(10) N-(3-(3-(9H-purin-6-yl)pyridin-2-yl amino)-2,4-difluorophenyl)-3,4-dimethoxy benzene sulfonamide;

(11) N-(3-(3-(9H-purin-6-yl)pyridin-2-yl amino)-2,4-difluorophenyl)cyclohexane sulfonamide;

(12) N-(3-(3-(9H-purin-6-yl)pyridin-2-yl amino)-2,4-difluorophenyl)-4-(trifluoromethoxy)benzene sulfonamide;

(13) N-(3-(3-(9H-purin-6-yl)pyridin-2-yl amino)-2,4-difluorophenyl)-4-fluoro-2-(trifluoromethyl)benzene sulfonamide;

(14) N-(3-(3-(9H-purin-6-yl)pyridin-2-yl amino)-2,4-difluorophenyl)-3-chloro-2-methyl benzene sulfonamide;

(15) N-(3-(3-(9H-purin-6-yl)pyridin-2-yl amino)-2,4-difluorophenyl)furan-2-sulfonamide;

(16) methyl-3-(N-(3-(3-(9H-purin-6-yl)pyridin-2-yl amino)-2,4-difluorophenyl)sulfamoyl)thiophene-2-carboxylate;

(17) N-(3-(3-(9H-purin-yl)pyridin-2-yl amino)-2,4-difluorophenyl)thiophene-3-sulfonamide;

(18) N-(3-(3-(9H-purin-6-yl)pyridin-2-yl amino)-2,4-difluorophenyl)furan-3-sulfonamide;

(19) N-(3-(3-(9H-purin-yl)pyridin-2-yl amino)-2,4-difluorophenyl)cyclopropane sulfonamide;

(20) N-(3-(3-(9H-purin-yl)pyridin-2-yl amino)-2,4-difluorophenyl)-2,4-dimethylthiazole-5-sulfonamide;

(21) N-(3-(3-(9H-purin-6-yl)pyridin-2-yl amino)-2,4-difluorophenyl)morpholine-4-sulfonamide;

(22) N-(3-(3-(9H-purin-6-yl)pyridin-2-yl amino)-2,4-difluorophenyl)-1-methyl-1H-imidazole-4-sulfonamide;

(23) N-(3-(3-(9H-purin-6-yl)pyridin-2-yl amino)-2,4-difluorophenyl)-5-methyl furan-2-sulfonamide;

(24) N-(3-(3-(9H-purin-6-yl)pyridin-2-yl amino)-2,4-difluorophenyl)-5-(1,3-dioxolane-2-yl)furan-2-sulfonamide;

(25) N-(3-(3-(9H-purin-6-yl)pyridin-2-yl amino)-2,4-difluorophenyl)-2,5-dimethylfuran-3-sulfonamide;

(26) N-(3-(3-(9H-purin-6-yl)pyridin-2-yl amino)-2,4-difluorophenyl)-5-methyl-2-(trifluoromethyl)furan-3-sulfonamide;

(27) N-(3-(3-(9H-purin-6-yl)pyridin-2-yl amino)-2,4-difluorophenyl)-2-chloro-6-methyl benzene sulfonamide;

(28) N-(3-(3-(9H-purin-6-yl)pyridin-2-yl amino)-2,4-difluorophenyl)-3-chloro-4-fluoro benzene sulfonamide;

(29) N-(3-(3-(9H-purin-6-yl)pyridin-2-yl amino)-2,4-difluorophenyl)-3-chloro-2-fluoro benzene sulfonamide;

(30) N-(3-(3-(9H-purin-6-yl)pyridin-2-yl amino)-2,4-difluorophenyl)pyridin-3-sulfonamide;

(31) N-(3-(3-(9H-purin-6-yl)pyridin-2-yl amino)-2,4-difluorophenyl)-2-methyl benzene sulfonamide;

(32) N-(3-(3-(9H-purin-6-yl)pyridin-2-yl amino)-2,4-difluorophenyl)-2-chloro benzene sulfonamide;

(33) N-(3-(3-(9H-purin-6-yl)pyridin-2-yl amino)-2,4-difluorophenyl)-3-chloro benzene sulfonamide;

(34) N-(3-(3-(9H-purin-6-yl)pyridin-2-yl amino)-2,4-difluorophenyl)-2,3-chloro benzene sulfonamide;

(36) N-(3-(3-(9H-purin-6-yl)pyridin-2-yl amino)-2,4-difluorophenyl)-2,3-dihydrobenzofuran-7-sulfonamide;

(37) N-(3-(3-(9H-purin-6-yl)pyridin-2-yl amino)-2,4-difluorophenyl)benzofuran-7-sulfonamide;

(38) N-(3-(3-(9H-purin-6-yl)pyridin-2-yl amino)-2,4-difluorophenyl)chroman-8-sulfonamide;

(39) N-(3-(3-(9H-purin-6-yl)pyridin-2-yl amino)-2,4-difluorophenyl)-2-methylbenzo[d]thiazole-6-sulfonamide;

(40) N-(3-(3-(9H-purin-6-yl)pyridin-2-yl amino)-2,4-difluorophenyl)-1-methyl-1H-indole-5-sulfonamide;
(41) N-(3-(3-(9H-purin-6-yl)pyridin-2-yl amino)-2,4-difluorophenyl)-1-methyl-1H-indole-4-sulfonamide;
(42) N-(3-(3-(9H-purin-6-yl)pyridin-2-yl at no 2,4-difluorophenyl)-1-methyl-1H-indole-7-sulfonamide;
(43) N-(3-(3-(9H-purin-6-yl)pyridin-2-yl amino)-2,4-difluorophenyl)-1-methyl-1H-pyrazole-4-sulfonamide; and
(44) N-(3-(3-(9H-purin-6-yl)pyridin-2-yl amino)-2,4-difluorophenyl)-5-chlorothiophene-4-sulfonamide.

5. A method for preparing the purinylpyridinylamino-2,4-difluorophenyl sulfonamide derivative of claim 1, comprising a step of reacting a compound of Formula 2 with a compound of Formula 3 in a base and a solvent to obtain a compound of Formula 1 as shown in Reaction Formula 1 below:

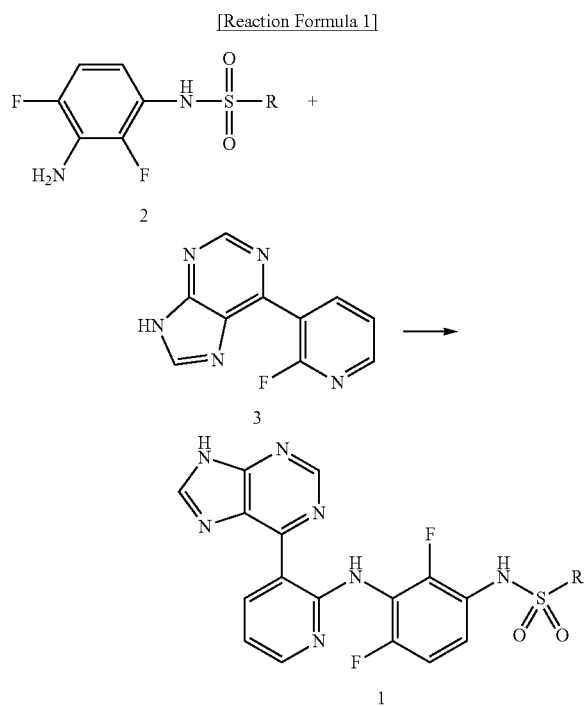

wherein R is the same as defined in the Formula 1 of claim 1.

6. The method for preparing the purinylpyridinylamino-2,4-difluorophenyl sulfonamide derivative according to claim 5, wherein the base is lithium (bistrimethylsilyl) amide and the solvent is tetrahydrofuran.

7. A method for preparing the purinylpyridinylamino-2,4-difluorophenyl sulfonamide derivative of claim 1, comprising a step of reacting a compound of Formula 4 with a compound of Formula 5 in a base and a solvent to obtain a compound of Formula 1 as shown in Reaction Formula 2 below:

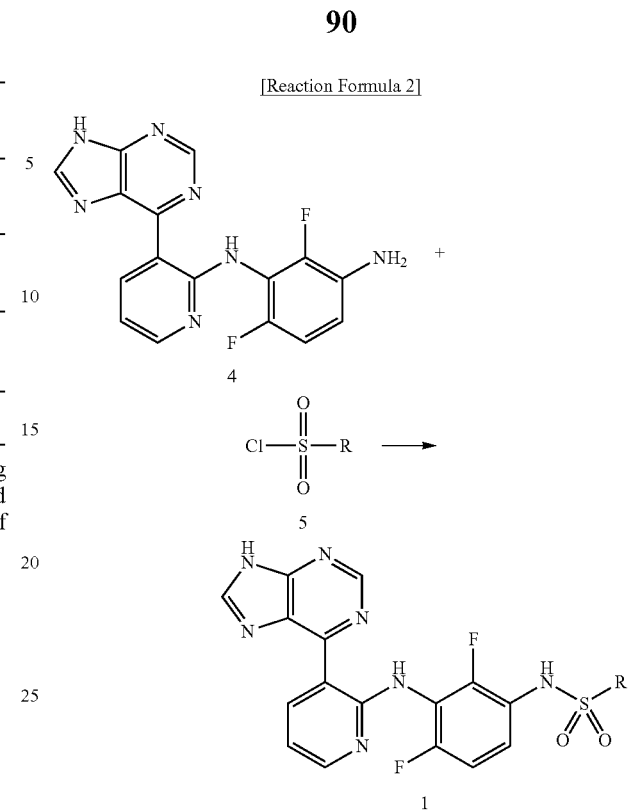

wherein R is the same as defined in the Formula 1 of claim 1.

8. The method for preparing the purinylpyridinylamino-2,4-difluorophenyl sulfonamide derivative according to claim 7, wherein the base is pyridine and the solvent is dichloromethane.

9. A pharmaceutical composition containing the purinylpyridinylamino-2,4-difluorophenyl sulfonamide derivative or the pharmaceutically acceptable salt thereof of claim 1.

10. A method for treating a disease induced by over-activity of Raf kinase comprising administering to a patient in need thereof the composition according to claim 9, wherein the disease induced by the over-activity of the Raf kinase is melanoma, colorectal cancer, prostate cancer, thyroid cancer, or ovarian cancer.

11. A health food composition containing the purinylpyridinylamino-2,4-difluorophenyl sulfonamide derivative or the pharmaceutically acceptable salt thereof of claim 1 and further comprising at least one component selected from the group consisting of a vitamin, a mineral, prunus mume extract, honey, fruit flavor, sugar, wheat flour, dairy products and natural powdered food.

12. A method for improving a disease induced by over-activity of Raf kinase comprising administering to a patient in need thereof the composition according to claim 11, wherein the disease induced by the over-activity of the Raf kinase melanoma, colorectal cancer, prostate cancer, thyroid cancer, or ovarian cancer.

* * * * *

UNITED STATES PATENT AND TRADEMARK OFFICE
CERTIFICATE OF CORRECTION

PATENT NO. : 9,216,981 B2  
APPLICATION NO. : 13/990910  
DATED : December 22, 2015  
INVENTOR(S) : Eun Kyong Shim et al.

Page 1 of 1

It is certified that error appears in the above-identified patent and that said Letters Patent is hereby corrected as shown below:

In the Claims:

In claim 4 column 87, lines 36-37, please delete "N-(3-(3-H-purin-6-yl)pyridin-2-yl amino)-2,4-difluo-rophenyl)-3,4-dichloro benezene sulfonamide" and insert --N-(3-(3-9H-purin-6-yl) pyridin-2-yl amino)-2,4-difluorophenyl)-3,4-dichloro benezene sulfonamide--

In claim 4 column 88, lines 8-9, please delete "N-(3-(3-(9H-purin-yl)pyridin-2-yl amino)-2,4-difluo-rophenyl) cyclopropane sulfonamide" and insert --N-(3-(3-(9H-purin-6-yl)pyridin-2-yl amino)-2,4-difluorophenyl) cyclopropane sulfonamide--

In claim 4 column 88, lines 11-12, please delete "N-(3-(3-(9H-purin-yl)pyridin-2-yl amino)-2,4-difluo-rophenyl)-2,4-dimethylthiazole-5-sulfonamide" and insert --N-(3-(3-(9H-purin-6-yl)pyridin-2-yl amino)-2,4-difluorophenyl)-2,4-dimethylthiazole-5-sulfonamide--

In claim 4 column 89, lines 8-9, please delete "N-(3-(3-(9H-purin-6-yl)pyridin-2-yl at no 2,4-difluo-rophenyl)-1-methyl-1H-indole-7-sulfonamide" and insert --N-(3-(3-(9H-purin-6-yl)pyridin-2-yl amino 2,4-difluorophenyl)-1-methyl-1H-indole-7-sulfonamide--

Signed and Sealed this  
Fifth Day of April, 2016

Michelle K. Lee  
*Director of the United States Patent and Trademark Office*